(12) United States Patent
Miller et al.

(10) Patent No.: US 7,230,238 B2
(45) Date of Patent: Jun. 12, 2007

(54) METHOD AND APPARATUS FOR CONTROL OF MOBILITY-BASED ION SPECIES IDENTIFICATION

(75) Inventors: Raanan A. Miller, Chestnut Hill, MA (US); Erkinjon G. Nazarov, Lexington, MA (US); Evgeny Krylov, Las Cruces, NM (US); Gary A. Eiceman, Las Cruces, NM (US)

(73) Assignee: Sionex Corporation, Bedford, MA (US)

( * ) Notice: Subject to any disclaimer, the term of this patent is extended or adjusted under 35 U.S.C. 154(b) by 0 days.

(21) Appl. No.: 11/011,949

(22) Filed: Dec. 13, 2004

(65) Prior Publication Data

US 2005/0156107 A1    Jul. 21, 2005

Related U.S. Application Data

(63) Continuation of application No. 10/462,206, filed on Jun. 13, 2003, now Pat. No. 7,005,632, which is a continuation-in-part of application No. 10/321,822, filed on Dec. 16, 2002, now Pat. No. 6,806,463, and a continuation-in-part of application No. 10/187,464, filed on Jun. 28, 2002, now Pat. No. 7,045,776, and a continuation-in-part of application No. 10/123,030, filed on Apr. 12, 2002, now Pat. No. 6,690,004.

(60) Provisional application No. 60/468,306, filed on May 6, 2003, provisional application No. 60/453,287, filed on Mar. 10, 2003, provisional application No. 60/418,671, filed on Oct. 15, 2002, provisional application No. 60/398,616, filed on Jul. 25, 2002, provisional application No. 60/389,400, filed on Jun. 15, 2002.

(51) Int. Cl.
*H01J 49/00* (2006.01)
*H01J 49/40* (2006.01)
*B01D 59/44* (2006.01)

(52) U.S. Cl. ............ 250/293; 250/281; 250/282; 250/286; 250/287

(58) Field of Classification Search ............ None
See application file for complete search history.

(56) References Cited

U.S. PATENT DOCUMENTS 2,615,135 A    10/1952    Glenn (Continued)

FOREIGN PATENT DOCUMENTS

RU    1412447 A1    6/1998

(Continued)

OTHER PUBLICATIONS

Buryakov et al., "Drift Spectrometer for the Control of Amine Traces in the Atmosphere," J. Anal. Chem., vol. 48, No. 1, pp. 112-121 (1993).

(Continued)

*Primary Examiner*—Nikita Wells
*Assistant Examiner*—Bernard E. Souw
(74) *Attorney, Agent, or Firm*—Fish & Neave IP Group, Ropes & Gray LLP

(57) ABSTRACT

System for control of ion species behavior in a time-varying filter field of an ion mobility-based spectrometer to improve species identification, based on control of electrical and environmental aspects of sample analysis.

18 Claims, 44 Drawing Sheets

U.S. PATENT DOCUMENTS

| | | | |
|---|---|---|---|
| 2,818,507 A | 12/1957 | Britten | |
| 2,919,348 A | 12/1959 | Bierman | |
| 3,511,986 A | 5/1970 | Llewellyn | |
| 3,619,605 A | 11/1971 | Cook et al. | |
| 3,621,240 A | 11/1971 | Cohen et al. | |
| 3,931,589 A | 1/1976 | Aisenberg et al. | |
| 4,019,989 A | 4/1977 | Hazewindus et al. | |
| 4,025,818 A | 5/1977 | Giguere et al. | |
| 4,136,280 A | 1/1979 | Hunt et al. | |
| 4,163,151 A | 7/1979 | Bayless et al. | |
| 4,201,921 A | 5/1980 | McCorkle | |
| 4,315,153 A | 2/1982 | Vahrenkamp | |
| 4,517,462 A | 5/1985 | Boyer et al. | |
| 4,761,545 A | 8/1988 | Marshall et al. | |
| 5,144,127 A | 9/1992 | Williams et al. | |
| 5,218,203 A | 6/1993 | Eisele et al. | |
| 5,298,745 A | 3/1994 | Kernan et al. | |
| 5,420,424 A | 5/1995 | Carnahan et al. | |
| 5,455,417 A | 10/1995 | Sacristan | |
| 5,479,815 A | 1/1996 | White et al. | |
| 5,492,867 A | 2/1996 | Kotvas et al. | |
| 5,508,204 A | 4/1996 | Norman | |
| 5,536,939 A | 7/1996 | Freidhoff et al. | |
| 5,541,408 A | 7/1996 | Sittler | |
| 5,654,544 A | 8/1997 | Dresch | |
| 5,723,861 A | 3/1998 | Carnahan et al. | |
| 5,736,739 A | 4/1998 | Uber et al. | |
| 5,763,876 A | 6/1998 | Pertinarides et al. | |
| 5,789,745 A | 8/1998 | Martin et al. | |
| 5,801,379 A | 9/1998 | Kouznetsov | |
| 5,811,059 A | 9/1998 | Genovese et al. | |
| 5,834,771 A | 11/1998 | Yoon et al. | |
| 5,838,003 A | 11/1998 | Bertsch et al. | |
| 5,869,344 A | 2/1999 | Linforth et al. | |
| 5,965,882 A | 10/1999 | Megerle et al. | |
| 5,985,536 A * | 11/1999 | De Keyzer et al. | 430/605 |
| 5,998,788 A | 12/1999 | Breit | |
| 6,051,832 A | 4/2000 | Bradshaw | |
| 6,055,151 A | 4/2000 | Tormey et al. | |
| 6,066,848 A | 5/2000 | Kassel et al. | |
| 6,107,624 A | 8/2000 | Doring et al. | |
| 6,107,628 A | 8/2000 | Smith et al. | |
| 6,124,592 A | 9/2000 | Spangler | |
| 6,180,414 B1 | 1/2001 | Katzman | |
| 6,188,067 B1 | 2/2001 | Chutjian et al. | |
| 6,200,539 B1 | 3/2001 | Sherman et al. | |
| 6,239,428 B1 | 5/2001 | Kunz | |
| 6,262,416 B1 | 7/2001 | Chutjian et al. | |
| 6,281,494 B1 | 8/2001 | Chutjian et al. | |
| 6,323,482 B1 | 11/2001 | Clemmer et al. | |
| 6,479,815 B1 | 11/2002 | Goebel et al. | |
| 6,495,823 B1 * | 12/2002 | Miller et al. | 250/286 |
| 6,498,342 B1 | 12/2002 | Clemmer et al. | |
| 6,504,149 B2 | 1/2003 | Guevremont et al. | |
| 6,509,562 B1 | 1/2003 | Yang et al. | |
| 6,512,224 B1 * | 1/2003 | Miller et al. | 250/286 |
| 6,540,691 B1 | 4/2003 | Philips | |
| 6,618,712 B1 | 9/2003 | Parker et al. | |
| 6,621,077 B1 | 9/2003 | Guevremont et al. | |
| 6,639,212 B1 | 10/2003 | Guevremont | |
| 6,653,627 B2 | 11/2003 | Guevremont | |
| 6,690,004 B2 * | 2/2004 | Miller et al. | 250/286 |
| 6,703,609 B2 | 3/2004 | Guevremont | |
| 6,713,758 B2 | 3/2004 | Guevremont | |
| 6,727,496 B2 | 4/2004 | Miller et al. | |
| 6,744,043 B2 | 6/2004 | Loboda | |
| 6,753,522 B2 | 6/2004 | Guevremont | |
| 6,770,875 B1 | 8/2004 | Guevremont | |
| 6,774,360 B2 | 8/2004 | Guevremont | |
| 6,787,765 B2 | 9/2004 | Guevremont | |
| 6,799,355 B2 | 10/2004 | Guevremont | |
| 6,806,463 B2 * | 10/2004 | Miller et al. | 250/286 |
| 6,806,466 B2 | 10/2004 | Guevremont | |
| 6,815,668 B2 | 11/2004 | Miller et al. | |
| 6,815,669 B1 * | 11/2004 | Miller et al. | 250/286 |
| 6,822,224 B2 | 11/2004 | Guevremont et al. | |
| 6,825,461 B2 | 11/2004 | Guevremont et al. | |
| 7,005,632 B2 * | 2/2006 | Miller et al. | 250/287 |
| 2001/0030285 A1 | 10/2001 | Miller et al. | |
| 2002/0070338 A1 | 6/2002 | Lododa | |
| 2002/0134932 A1 | 9/2002 | Guevremont et al. | |
| 2003/0020012 A1 | 1/2003 | Guevremont | |
| 2003/0038235 A1 | 2/2003 | Guevremont et al. | |
| 2003/0052263 A1 * | 3/2003 | Kaufman et al. | 250/281 |
| 2003/0070913 A1 | 4/2003 | Miller et al. | |
| 2003/0089847 A1 | 5/2003 | Guevremont et al. | |
| 2003/0132380 A1 * | 7/2003 | Miller et al. | 250/286 |
| 2004/0094704 A1 * | 5/2004 | Miller et al. | 250/287 |
| 2004/0136872 A1 * | 7/2004 | Miller et al. | 422/83 |
| 2004/0232326 A1 | 11/2004 | Guevremont et al. | |
| 2005/0029449 A1 * | 2/2005 | Miller et al. | 250/293 |
| 2005/0040330 A1 * | 2/2005 | Kaufman et al. | 250/293 |
| 2005/0051719 A1 * | 3/2005 | Miller et al. | 250/287 |
| 2005/0092914 A1 * | 5/2005 | Miller et al. | 250/287 |
| 2005/0109930 A1 * | 5/2005 | Hill et al. | 250/286 |
| 2005/0121607 A1 | 6/2005 | Miller et al. | |
| 2005/0133716 A1 * | 6/2005 | Miller et al. | 250/293 |
| 2005/0139762 A1 * | 6/2005 | Miller et al. | 250/282 |
| 2005/0145789 A1 * | 7/2005 | Miller et al. | 250/290 |
| 2005/0156107 A1 * | 7/2005 | Miller et al. | 250/293 |
| 2005/0167583 A1 | 8/2005 | Miller et al. | |
| 2005/0173629 A1 | 8/2005 | Miller et al. | |
| 2005/0194527 A1 | 9/2005 | Guevremont et al. | |
| 2005/0194532 A1 | 9/2005 | Guevremont et al. | |
| 2005/0253061 A1 * | 11/2005 | Cameron et al. | 250/287 |

FOREIGN PATENT DOCUMENTS

| | | |
|---|---|---|
| RU | 1485808 A1 | 6/1998 |
| SU | 966583 A | 10/1982 |
| SU | 1337934 A2 | 9/1987 |
| SU | 1627984 A2 | 2/1991 |
| WO | WO-96/19822 A1 | 6/1996 |
| WO | WO-00/08454 | 2/2000 |
| WO | WO-00/08455 | 2/2000 |
| WO | WO-00/08456 | 2/2000 |
| WO | WO-00/08457 | 2/2000 |
| WO | WO-01/08197 A1 | 2/2001 |
| WO | WO-01/22049 A2 | 3/2001 |
| WO | WO-01/35441 A1 | 5/2001 |
| WO | WO-01/69217 A2 | 9/2001 |
| WO | WO-01/69220 A2 | 9/2001 |
| WO | WO 01/69220 A2 | 9/2001 |
| WO | WO-01/69647 A2 | 9/2001 |
| WO | WO-02/071053 A2 | 9/2002 |
| WO | WO-02/083276 | 10/2002 |
| WO | WO-03/005016 | 1/2003 |
| WO | WO-2003/015120 | 2/2003 |
| WO | WO-03/067237 A2 | 8/2003 |
| WO | WO-03/067242 A1 | 8/2003 |
| WO | WO-03/067243 A1 | 8/2003 |
| WO | WO-03/067625 A1 | 8/2003 |
| WO | WO-2004/029603 A2 | 4/2004 |
| WO | WO-2004/029614 A1 | 4/2004 |
| WO | WO-2004/030022 A2 | 4/2004 |
| WO | WO-2004/030023 A2 | 4/2004 |
| WO | WO-2004/030129 A2 | 4/2004 |

OTHER PUBLICATIONS

Buryakov et al., "Separation of Ions According to Mobility in a Strong AC Electric Field," Letters to Journal of Technical Physics, vol. 17, pp. 11-12 (1991).

Riegner et al., "Qualitative Evaluation of Field Ion Spectrometry for Chemical Warfare Agent Detection," Proceedings of the ASMS Conference on Mass Spectrometry and Allied Topics, pp. 473A-473B (1997).

Carnahan et al., "Field Ion Spectrometry—A New Technology for Cocaine and Heroin Detection," SPIE, vol. 2937, pp. 106-119 (1997).

Miller et al., "A Novel Micromachined High-Field Asymmetric Waveform-Ion Mobility Spectrometer," Sensors and Actuators B, vol. B67, No. 3, pp. 300-306 (2000).

Guevremont et al., "Calculation of Ion Mobilities from Electrospray Ionization High-Field Asymmetric Waveform Ion Mobility Spectrometry Mass Spectrometry," Journal of Chemical Physics, vol. 114, No. 23, pp. 10270-10277 (2001).

Krylov, "Pulses of Special Shapes Formed on a Capacitive Load," Instruments and Experimental Techniques, vol. 40, No. 5, (1997???). Also cited in Database Nauka/Interperiodika Online!, International Academic Publishing Company (IAPC), Russia, E. Krylov.

"A Micromachined Field Driven Radio Frequency-Ion Mobility Spectrometer for Trace Level Chemical Detection," A Draper Laboratory Proposal Against the "Advanced Cross-Enterprise Technology Development for NASA Missions," Solicitation, NASA NRA 99-OSS-05.

Miller et al., "A MEMS Radio-Frequency Ion Mobility Spectrometer for Chemical Agent Detection," Proceedings of the 2000 SolidState Sensors and Actuators Workshop (Hilton Head, SC, Jun. 2000).

Miller et al., "A MEMS radio-frequency ion mobility spectrometer for chemical vapor detection," Sensors and Actuators, vol. 91, pp. 301-312 (2001).

Eiceman et al., "Miniature radio-frequency mobility analyzer as a gas chromatogrphic detector for oxygen-containing volatile organic compounds, pheromones and other insect attractants," Journal of Chromatography, vol. 917, pp. 205-217 (2001).

Schneider et al., "High Sensitivity GC-FIS for Simultaneous Detection of Chemical Warfare Agents," Journal of Process Analytical Chemistry, vol. 5, Nos. 3, 4, pp. 124-136 (2000).

Burykov et al., "Device and Method for Gas Electrophoresis, Chemical Analysis of Environment," ed. Prof. V.V. Malakhov, Novosibirsk: Nauka, pp. 113-127 (1991).

Pilzecker et al., "On-Site Investigations of Gas Insulated Substations Using Ion Mobility Spectrometry for Remote Sensing of SF6 Decomposition," IEEE, pp. 400-403 (2000).

Barnett et al., "Isotope Separation Using High-Field Asymmetric Waveform Ion Mobility Spectrometry," Nuclear Instruments & Methods in Physics Research, vol. 450, No. 1, pp. 179-185 (2000).

Buryakov et al., "A New Method of Separation of Multi-Atomic Ions by Mobility at Atmospheric Pressure Using a High-Frequency Amplitude-Asymmetric Strong Electric Field," International Journal of Mass Spectrometry and Ion Processes, vol. 128, pp. 143-148 (1993).

Carnahan et al., "Field Ion Spectrometry—A New Analytical Technology for Trace Gas Analysis," ISA, vol. 51, No. 1, pp. 87-96 (1996).

Guevremont et al., "High Field Asymmetric Waveform Ion Mobility Spectrometry-Mass Spectrometry: An Investigation of Leucine Enkephalin Ions Produced by Electrospray Ionization," J. Am. Soc. Mass. Spectrom., vol. 10, pp. 492-501 (1999).

Handy et al., "Determination of Nanomolar Levels of Perchlorate in Water by ESI-FAIMS-MS," J. Anal. At. Spectrometry, vol. 15, pp. 907-911 (2000).

Krylov, "A Method of Reducing Diffusion Losses in a Drift Spectrometer," Technical Physics, vol. 4d, No. 1, pp. 113-116 (1999).

Guevremont et al., "Atmospheric Pressure Ion Focusing in a High-Field Asymmetric Waveform Ion Mobility Spectrometer," Review of Scientific Instruments, vol. 70, No. 2, pp. 1370-1383 (1999).

Javahery et al., "A segmented radiofrequency-only quadrupole collision cell for measurements of ion collision cross section on a triple quadrupole mass spectrometer," J. Am. Soc. Mass. Spectrom. 8:697-702 (1997).

Verenchikov et al., "Analysis ions in solutes by gaseous ion analyzer—chemical analysis of the environmental objects," red. Malakhov. Novosibirsk, Nauka pp. 127-134 (1991).

Phillips, M., "Method for the Collection and Assay of Volatile Organic Compounds in Breath," Analytical Biochemistry, 247:272-278 (1997).

Shute et al., "Curie-point Pyrolysis Mass Spectrometry Applied to Characterization and Identification of Selected *Bacillus* Species," J. Gen. Microbiology, 130:343-355 (1984).

Krylov, E.V., "Comparison of the Planar and Coaxial Field Asymmetrical Waveform Ion Mobility Spectrometer (FAIMS)," International Journal of Mass Spectrometry, 225, (2003) pp. 39-51.

* cited by examiner

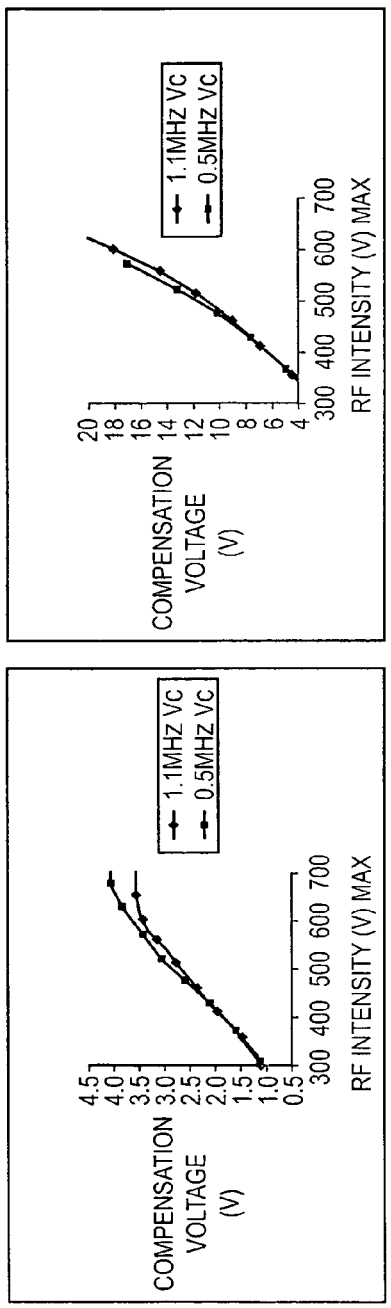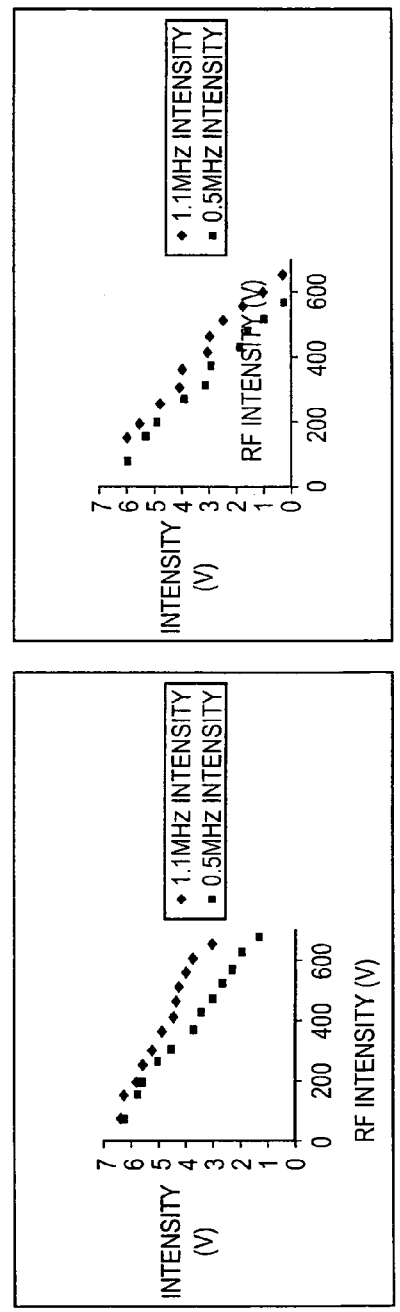
FIG. 6A
FIG. 6B
FIG. 6C
FIG. 6D

Intentionally left blank

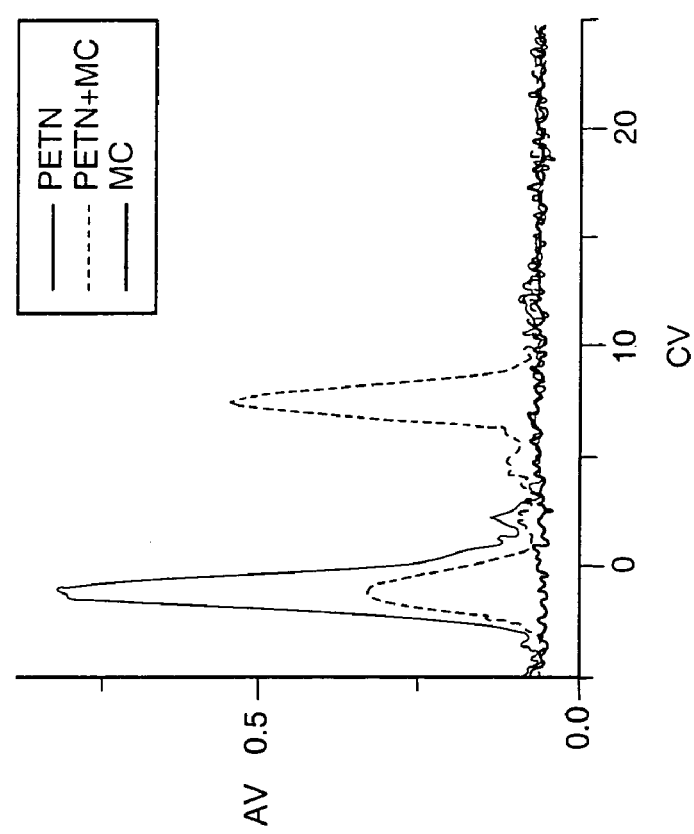

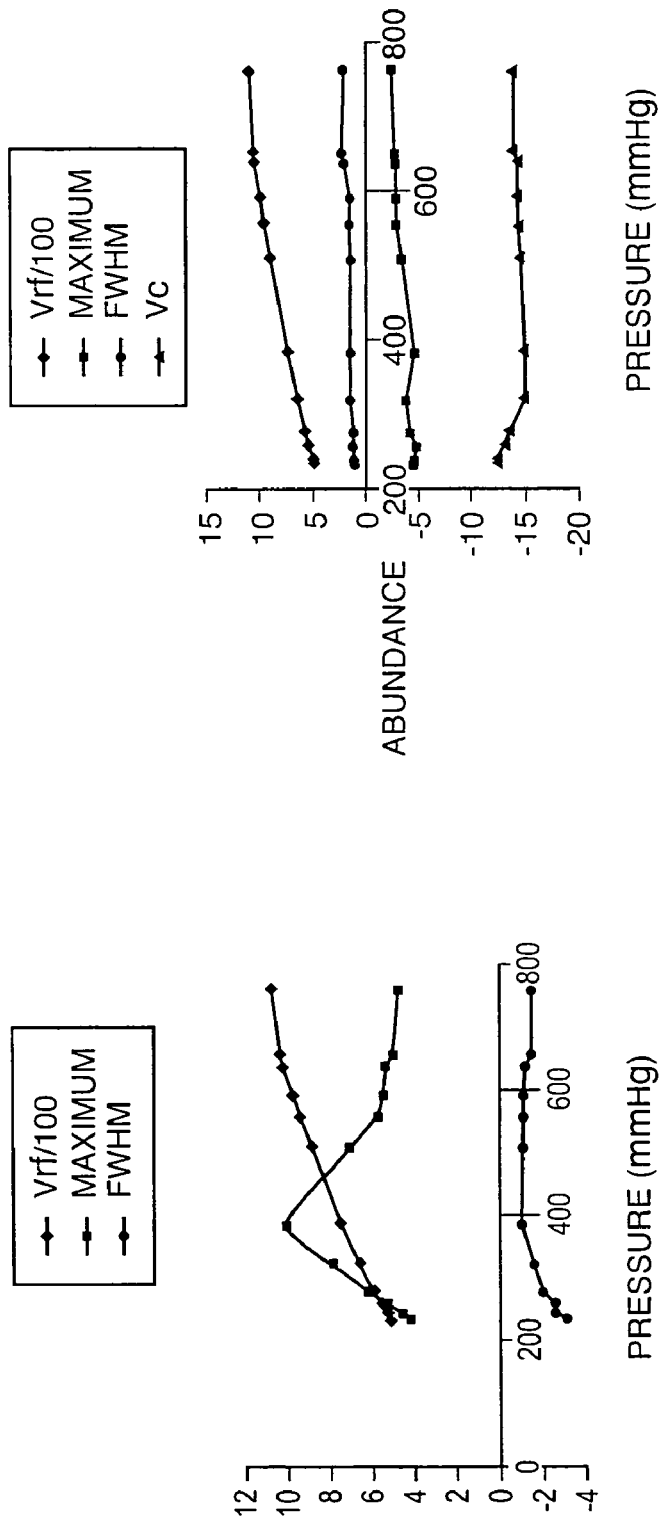

COMPENSATION VOLTAGE

COMPENSATION VOLTAGE

METHOD AND APPARATUS FOR CONTROL OF MOBILITY-BASED ION SPECIES IDENTIFICATION

RELATED APPLICATIONS

This patent application is a continuation of U.S. patent application Ser. No. 10/462,206 filed on Jun. 13, 2003, now U.S. Pat. No. 7,005,632, which is a continuation-in-part of U.S. patent application Ser. No. 10/321,822 filed Dec. 16, 2002, now U.S. Pat. No. 6,806,463, a continuation-in-part of U.S. patent application Ser. No. 10/123,030 filed Apr. 12, 2002, now U.S. Pat. No. 6,690,004, and a continuation-in-part of U.S. patent application Ser. No. 10/187,464 filed Jun. 28, 2002, now U.S. Pat. No. 7,045,776, and which claims the benefit of U.S. Provisional Application No. 60/389,400 filed Jun. 15, 2002, claims the benefit of U.S. Provisional Application No. 60/398,616 filed Jul. 25, 2002, claims the benefit of U.S. Provisional Application No. 60/418,671 filed Oct. 15, 2002, claims the benefit of U.S. Provisional Application No. 60/453,287 filed Mar. 10, 2003, and claims the benefit of U.S. Provisional Application No. 60/468,306 filed May 6, 2003. The entire teachings of the above-identified applications are incorporated herein by reference.

FIELD OF THE INVENTION

This invention relates to methods and apparatus for detection and identification of substances in general, and more particularly to methods and apparaturs for analysis of ions by ion mobility.

BACKGROUND OF THE INVENTION

There are many situations where it is desired to identify chemical compounds in a sample. Such samples may be taken directly from the environment or they may be provided by front end specialized devices to separate or prepare compounds before analysis. Furthermore, recent events have seen members of the general public exposed to dangerous chemicals in situations where previously no thought was given to such exposure. There exists, therefore, a demand for low cost, accurate, easy to deploy and use, reliable devices capable of identifying the chemical content of a sample.

One class of known chemical analysis instruments is referred to as mass spectrometers. Mass spectrometers are generally recognized as being the most accurate type of detectors for compound identification, given that they can generate a fingerprint pattern for even fragment ions. However, mass spectrometers are quite expensive and large and are relatively difficult to deploy in the field. Mass spectrometers also suffer from other shortcomings such as the need to operate at low pressures, resulting in complex support systems. These systems also require a highly trained user to tend to operations and interpret results.

Another class of known chemical analysis instruments enable used of atmospheric-pressure chemical ionization. Ion analysis is based on the recognition that ion species have different ion mobility characteristics under different electric field conditions at elevated pressure conditions including atmospheric pressure. Practices of the concept include time-of-flight Ion Mobility Spectrometry (IMS) and differential mobility spectrometry (DMS), the latter also sometimes referred to as field asymmetric ion mobility spectrometry (FAIMS). These systems enable chemical species identification at atmospheric pressure, preferably based on dry and clean gas samples.

In a conventional time-of-flight IMS device (sometimes referred to as TOF-IMS), a propelling DC field gradient and a counter gas flow are set and an ionized sample is released into the field which flows to a collector electrode. Ion species are identified based on the DC field strength and time of flight of the ions to the collector. The electric field is weak where ion mobility is constant.

DMS systems identify ion species by mobility behavior in a high asymmetric RF field, where ions flow in a carrier gas and are shifted in their path by an electric field. The conventional DMS operates with at a selected RF field at Vmax and species detections are correlated with a pre-set, or scanned, DC compensation voltage (Vc). Species are identified based upon correlation of Vmax and Vc with historical detect data. It is well-known that for a given ion species in a sample, as the amplitude of the asymmetric RF voltage (at Vmax) changes, the amplitude of the DC compensation voltage (Vc) required for passage of that species through the filter field will also change. The amount of compensation depends upon species characteristics.

A typical DMS device includes a pair of opposed filter electrodes defining an analytical gap between them in a flow path (also known as a drift tube). Ions flow into the analytical gap. An asymmetric RF field (sometimes referred to as a filter field, a dispersion field or a separation field) is generated between the electrodes transverse to the carrier gas/ion flow in the gap. Field strength, E, varies as the applied RF voltage (sometimes referred to as dispersion or separation voltage, or Vrf) and size of the gap between the electrodes. Such systems operate at atmospheric pressure.

Ions are displaced transversely by the RF field, with a given species being displaced a characteristic amount toward the electrodes per cycle. DC compensation (Vc) is applied to the electrodes along with Vrf to compensate the displacement of a particular species. Now the applied compensation will offset transverse displacement generated by the applied Vrf for that particular ion species. The result is zero or near-zero net transverse displacement of that species, which enables that species to pass through the filter for detection. All other ions undergo a net displacement toward the filter electrodes and will eventually undergo collisional neutralization on one of the electrodes.

If the compensation voltage is scanned for a given RF field, a complete spectrum of ion species in the sample can be produced. The recorded image of this spectral scan is sometimes referred to as a "mobility scan", as an "ionogram", or as "DMS spectra". The time required to complete a scan is system dependent. Relatively speaking, a prior art IMS scan might take on the order of a second to complete while and a prior art DMS might take on the order of 10 seconds to complete.

DMS operates based on the fact that an ion species will have an identifying property of high and low field mobility in the analytical RF field. Thus DMS detects differences in an ion's mobility between high and low field conditions and classifies the ions according to these differences. These differences reflect ion properties such as charge, size, and mass as well as the collision frequency and energy obtained by ions between collisions and therefore enable identification of ions by species.

Illustrative examples of mobility scans based on the output from a DMS device are shown in FIG. 1A and FIG. 1B. As shown in FIG. 1A, a single compound, acetone, was submitted to the DMS analyzer. The illustrated plot is typical of the observed response of the DMS device, with detected acetone ions in this example forming a peak intensity at a compensation voltage of about −1.5 volts. This is useful information, such that future detections of a peak at this compensation in this device is indicative of detection of acetone.

In FIG. 1B, the analyzed sample consisted of acetone and an isomer of xylene (o-xylene). The acetone peak appears at about −2.5 volts while o-xylene appears at about −4 volts. Data representing these detection peaks can be compared against stored data for known compounds for this device and the applied RF field and compensation, and identification is made based upon a data match. FIG. 1B demonstrates unique detection peaks according to ion mobility characteristics for different ion species in the sample under test, i.e., o-xylene and acetone.

Various chemical species in a sample can be identified according to the conventional DMS process. However, accurate identification of several species in a sample whose detection spectra overlap is difficult. This is in part due to the fact that DMS detection peaks are relatively broad compared to a mass spectrometer, so overlap is more likely than with a mass spectrometer. In fact, where several ion species exhibit similar behavior in the DMS filter field their associated DC compensation will be very close, and so their detection spectra (detection peaks) will present as overlapped.

This "overlap" of detection peaks interferes with species identification. But discrimination between overlapping spectra is not easily achieved and similar species are not so easily separated.

Furthermore, false negative detections are dangerous when dangerous compounds are at issue, while false positives can reduce trust in a detection system. Therefore improved spectrometer performance is an important goal of the present invention.

It is therefore an object of the present invention to provide a fast and simple system, whether method or apparatus, capable of a high degree of species discrimination and accurate species identification for chemical analysis.

SUMMARY OF THE INVENTION

A system of the invention, whether as method or apparatus, provides for control of ion species behavior in a time-varying filter field of an ion mobility-based spectrometer. In practice of the invention, the filter field has both electrical and environmental aspects that are manipulated to improve system performance and to fine tune sample analysis.

One illustrative system of the present invention has several aspects, including: detecting and provisionally identifying at least one ion species, typically one out of several ion species with overlapping spectra, at a first set of filter operating conditions; selectively changing these operating conditions based upon the first detection and predicting the effect of such change upon the behavior of such provisionally identified species; and then confirming the provisional species identification based upon detection of the predicted behavior. Furthermore, additional detections can be made to further assure accuracy of detection. It is noted that after species are separated, they are passed for downstream use or further processing, such as for species detection and identification.

In a further embodiment of the present invention, a sample is analyzed in a DMS filter of the invention at a first set of filter operating conditions and one or several ion species that pass through the filter are detected. The first set of operating conditions is selected based upon interest in monitoring for a chosen species or range of species or based upon interest in generating a spectral scan for a chemical sample. Next, especially in the case where presence of overlapping detection peaks is suspected, a provisional prediction of the identity of at least one detected ion species is made based on knowledge of the parameters of the first set of operating conditions and by reference to a lookup table of behavior data that includes such species.

This process continues wherein the parameters of a second set of operating conditions is selected according to their expected impact upon the expected travel behavior in the filter of the provisionally identified ion species, again by reference to a lookup table of relevant species behavior data. A second detection is made, premised on causing and detecting the predicted behavior of the provisionally identified species at the second set of operating conditions. Under such circumstances, an affirmative detection of such predicted behavior enables confirmation of the first provisional identification of the detected species. This confirmation increases the reliability of the species identification process.

The second set of operating conditions is selected based on knowledge of the first set of operating conditions and with the intention of confirming the first detection rather than merely making an independent second detection. In practical effect, the second set of operating conditions is selected to cause differential shifting of spectra, and in some cases to eliminate or reduce the spectral overlap when the second detection is made and spectra are evaluated.

Thus, it will now be understood that it is the combination of the first and second detection that enables a high degree of reliability in species identification made according to the invention. While the first detection and species identification is provisional, once a confirming detection of the predicted behavior of the provisionally identified species at the second set of operating conditions is answered in the affirmative, then the provisional identification of species is relied upon as accurate. Meanwhile, if the confirming detection answers in the negative, then a redetection under changed operating conditions is called for.

However, the invention also contemplates an alternative identification process in which confirmation is based upon absence of detection of the provisionally identified ion species at the second set of operating conditions (i.e., if no detection, then it must be x; or, if a detection, then it must y), again based upon stored knowledge of species behavior under known operating conditions.

It will now be understood that the confirming second set of operating conditions is selected based upon knowledge of characteristic behavior of the predicted detected ion species at that second set of operating conditions. The particular parametric changes to be made are dictated by what is known about the behavior of the provisionally identified species in the DMS field. These parametric differences must cause predictable and characteristic changes in the travel behavior of the provisionally identified ion species. Reference to a lookup table of associated behavior data, or to artificial intelligence that utilizes ion behavior knowledge, can be used to set the second set of operating conditions.

Both the first and the second set of operating conditions are defined in terms of RF field, RF waveform characteristics, applied field compensation, and environmental factors (e.g., content and flow). However, we have found that to assure a high level of accurate species prediction, the changes in the parameters of the first set of operating conditions include changes to the RF waveform characteristics and/or changes to the environmental aspects of the operating conditions. These changes are aside from possible changes to the RF field and DC compensation. However it is further noted that field strength changes alone are not reliable or sufficient in these overlap situations.

In practice of the present invention, we improve DMS species detection and identification by improving species separation. Thus, in practice of the present invention, an ion species is identified by making a first detection at a first set of filter operating conditions and then followed by a second detection at a second related set of selected operating conditions. This process includes noting of operating conditions and then noting changes in ion behavior after adjusting these conditions.

It will thus be appreciated that species identification is based on obtaining related data points for a detected species. Creating and using multiple data points increases accuracy and wisely selecting these data points both increases accuracy and reduces the data processing workload. The method of making, generating and using such data points is part of the present invention.

In one process of the invention, we make a first ion species detection at a first set of operating conditions. This first set of conditions is expressed as a first parameter set of mobility-influencing variables, i.e., RF frequency, field strength, duty cycle, compensation level, pressure, humidity, flow rate, gas composition, etc. We provisionally identify the detected species based on historical data. We then establish a second parameter set of field variables to make a second (or confirming) detection at a second (or confirming) set of operating conditions. This second parameter set of variables is selected in view of the first detection, and this detection of expected detection data confirms accuracy of the provisional identification. In a further practice of the invention, a third parameter set of field variables is used to make a third detection at a third set of operating conditions to further confirm species identification.

In a special embodiment of the invention, a device is dedicated to detection of a prescribed analyte and detection is made at a prescribed set of operating conditions. Then positive and negative detection mode data, and/or data from detection at a second set of prescribed operating conditions, is used for species identification.

Thus it will be appreciated that in practice of the present invention we improve species identification by improving separation between analytes. We do this by controlling mobility-impacting aspects of the filter field, which includes a process we generally refer to as "waveform control". We decide which parameters of the field to adjust based on known species behavior. We set the spectrometer to detect a given species or class of species and then refine the filter field and detection process to improve species separation. Adjustments to the filter field are selectively made in terms of field, DC compensation, frequency, duty cycle, and/or asymmetry and in terms of pressure, flow rate, gas composition, moisture, ionization process, and/or presence and level of doping. The result is improved species separation and improved species identification.

It will be appreciated that we can optimize ion species analysis in practice of the illustrative apparatus discussed below by making any one of several adjustments to the filter operating conditions and making multiple detections. Specifically, we identify and control electrical and environmental aspects of the spectrometer filter field. We make adjustments to these electrical and environmental aspects as if they were "knobs" to improve species analysis. We have identified species-specific adjustments and therefore we teach their use as aids in species discrimination. The result is improved specificity and sensitivity in atmospheric pressure chemical species analysis.

Generally speaking, we divide adjustment to the filter field conditions into two categories: electrical and environmental. These adjustments are made for specific purposes to achieve prescribed results for detected conditions and are made based upon knowledge of the affect these parametric adjustments will have on system performance and analyte behavior. With such assurance and the fact that we identify an ion species with multiple data points, our species identifications are highly accurate with minimized false detections.

It is known that in DMS prior art, a particular ion species can be detected by setting certain combinations of RF characteristics and strength and DC compensation for the ion filter field. If the values of the RF and DC are fixed, then the system is dedicated to detection of a particular ion species of interest, but if the DC compensation voltage is scanned through a range of voltages, then a complete mobility scan can be generated for the sample under test. This scan is based on the conventional practice of establishing an RF filter field at a given field strength and given frequency and then scanning the DC compensation. Different species are compensated at different DC compensation levels. Therefore theoretically a scan of DC compensation will provide a scan of the chemical sample under test.

It will be appreciated that mobility of ion species in the filter field may change responsively and characteristically as parameters of the filter operating conditions are changed, and that these responses are different from just scanning the DC compensation. Thus, in order to improve species discrimination, especially in complex samples, we have found that in addition to or combined with DC compensation, we can set and/or scan field parameters, which can be set at a fixed value or can be scanned through a range of values, to affect ions in the field and to tune the field to pass a particular limited set of ions or ion species. This scanning may include stepping or sweeping through a range of values. The particular parameters are selected based on predicted impact on behavior of species of interest.

We can mix various combinations of these adjustments in a species-specific manner to improve species discrimination. As a result, we provide better separated ion species to a detector for improve sample analysis. This detector may be on-board or otherwise. In one embodiment the present invention provides a mobility-based pre-filter for a mass spectrometer.

It will be further appreciated that the present invention does not need to follow the conventional wisdom of IMS and DMS of analyzing the chemical sample at or about atmospheric pressure and at reduced or zero humidity. In fact, we come to recognize that pressure and humidity are parameters that can be favorably adjusted and quite unexpectedly that benefits can be derived from operation of an atmospheric pressure ion mobility detection system at other than atmospheric pressure and/or at elevated humidity to achieve improved ion species separation.

Therefore, in several embodiments of the invention, we provide and regulate pressure and/or humidity to favorably and differentially affect and control ion species separation in the electric field. In such embodiments, the operating pressure need not be at the conventional atmospheric level, and the humidity need not be at the conventional trace level, wherein we can choose to optimize these parameters to compensate ion mobility and to favorably control the analytical process and consequent species identification.

This invention has practical applications. For example, we can accurately separate, detect and identify chemical species, even though it may be a difficult chemical to isolate in an air sample. In one practice of the invention, we select an RF intensity and adjust pressure and humidity to desired values, based on known species data, and then we perform a mobility scan by scanning the DC compensation voltage to detect acetone and sulfur hexafluoride (SF6) in a sample containing air, acetone and SF6. The air, acetone and SF6 are easily separated, detected and identified in this illustrative practice of the invention.

It will now be appreciated that the concept of applying compensation to the analytical filter field is broader than the conventional concept of varying the DC compensation voltage. In short, we have recognized that there are numerous "controls" or "knobs" which may be adjusted in a manner that predictably affects ion mobility for the purpose of compensating (or tuning) the electric field to pass ion species to the detector. The result is improved specificity in species discrimination and detection, especially in complex samples. The benefit is increased accuracy in species identification with reduced false positives and reduced false negatives.

In a method of the invention, we control and adjust operating conditions by several techniques. For example, we can adjust the electric field frequency in a DMS system, which affects the 'selectivity' (width) of the scanned peaks in the detector output or filter. WE can also selections, such as light versus heavy ions for separation.

The process can be implemented by changing the value of a fixed operating frequency or by dynamic frequency modulation where a range of frequencies could be scanned, for example. As well, the waveform (i.e., square, triangular, sinusoidal, ramp, etc.) may be adjusted, wherein pulse shape is used to affect response of the ion in the field in a known manner. This control may be augmented by adjusting the analytical gap environmental parameters (such as by changing the pressure and/or concentration of water, other polar molecules, or other dopants) to positively affect response of ion species in the field.

In yet another embodiment of the present invention, a DMS device operates simultaneously in both positive ion detection mode ("positive mode" or "positive ion mode") and negative ion detection mode ("negative mode" or "negative ion mode") for a more complete real-time sample analysis. Therefore another practice of the invention detects and separates multiple species simultaneously based on both ion mobility and ion polarity.

We broadly define doping as the process of adding an analyte to a sample flow for the purpose of affecting ion species behavior. We can use this doping to assist in identifying analytes of interest. We define several forms of doping.

Doping may include the step of use of a dopant additive to improve ionization efficiency. Doping may include the step of addition of an analyte in the ionization process whose ionization releases free electrons which enables formation of negative ions for species with high electron affinity. Doping may include the step of addition of an analyte that affects species behavior and causes peak shift.

We can combine data from these doping-assisted detections with detections made without the benefit of dopant. The characteristics of a given chemical sample will dictate its ionization in these conditions, i.e., a signature. Thus it will be appreciated that in an embodiment of the invention multiple detect data are compared against stored detection data so as to be able to make positive and reliable species signature identification.

In an illustrative practice of the invention, we note detection peak characteristics (ion polarity, number of peaks, peak location, intensity, width, etc.) at a first set of operating conditions (noting ionization source, dopant level if any, and other electric and environmental field parameters, including Vmax, Vmin, Vc, RF frequency, duty cycle, etc.). We then change at least one mobility-effecting parameter in the operating conditions (such as adjusting dopant level, Vmax (and/or the ratio of Vmax/Vmin), Vc, RF frequency, waveshape and/or duty cycle) and note changes in peak characteristics (such as location, intensity, width, etc.) at the second set of operating conditions. This collected data is compared to a lookup table of detection data for known compounds in such conditions. Upon data match, a species identification is made with a high degree of reliability. Furthermore, in preferred practice of the invention, we make the second detection at a second set of operating conditions that is selected guided by knowledge of the first set of operating conditions and the first detection results, with at least one change being in made in parameters of the operating conditions, preferably one that includes other than merely changing field strength and adjusting DC compensation. In one example, the second detection amounts to a measurement of peak shift associated with the change in operating conditions.

In another illustrative embodiment of the invention, a DMS method for identifying chemical species in a sample includes several steps. The system provides a DMS filter field which is adjustable to a plurality of DMS filter operating conditions. The DMS filter operating conditions are characterized as influencing mobility behavior of ions in the filter. Behavior of the ionized sample is analyzed in the filter at a first set of operating conditions, with the sample including at least one ion species and the analysis being based upon aspects of mobility behavior of the at least one ion species in the first set of operating conditions. This is followed by detecting a spectral peak associated with the at least one ion species and the first set of operating conditions. The next step includes provisionally identifying the at least one ion species based upon that species detection and the associated operating condition parameters. Based upon the provisional identification, a change is made to parameter(s) of the operating conditions at least in terms of waveform characteristics, RF frequency, duty cycle, gas composition, pressure, presence of dopant, or flow rate, and predicting the effect of such change upon the provisionally identified at least one ion species measured in terms of change in at least one characteristic of the spectral peak. A change in the spectral is expected. A detection is made of the spectral peak associated with the at least one ion species at the second set of operating conditions to confirm the predicted change. Based on the first detection and the confirmation, which verifies the provisional identification of the at least one ion species, an announcement is made identifying the at least one ion species. This identification is made with a high degree of reliability.

The present invention may be practiced in ion mobility-based systems, including IMS and DMS, and may have various cylindrical, planar, radial and other structural configurations. It will be further appreciated that methods of the invention include one or all of the following actions: separation, detection and/or identification of ion species according to aspects and/or changes in mobility behavior in a controlled filter field. These terms may be generally referred to as ion species "analysis".

BRIEF DESCRIPTION OF THE DRAWINGS

The foregoing and other objects, features and advantages of the invention will be apparent from the following more particular description of illustrative and preferred embodiments of the invention, as illustrated in the accompanying drawings in which like reference characters refer to the same parts throughout the different views. The drawings are not necessarily to scale, emphasis instead being placed upon illustrating the principles of the invention, wherein:

FIG. 6 shows the effect of electric field strength on negative and positive RIP peak parameters for two frequencies, in practice of the invention.

FIG. 25A–E shows effect of polar doping on DNT with different concentrations of water, in practice of the invention.

FIG. 32A–B shows quantified effect of electric field compensation for pressure decrease for positive (A) and negative (B) background spectra, in practice of the invention.

DETAILED DESCRIPTION OF PREFERRED EMBODIMENTS

Figure 1A:
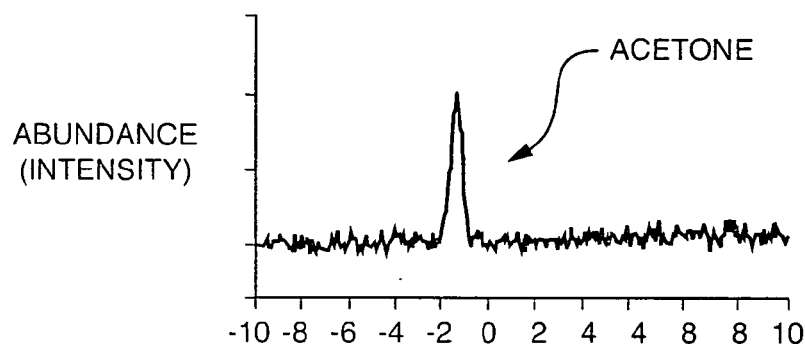
FIG. 1A and FIG. 1B are a prior art mobility scans plotting detection intensity versus compensation voltage for a given field strength in a field asymmetric ion mobility spectrometer, for acetone alone (1A) and for a combination of o-xylene and acetone (1B).
Figure 1B:
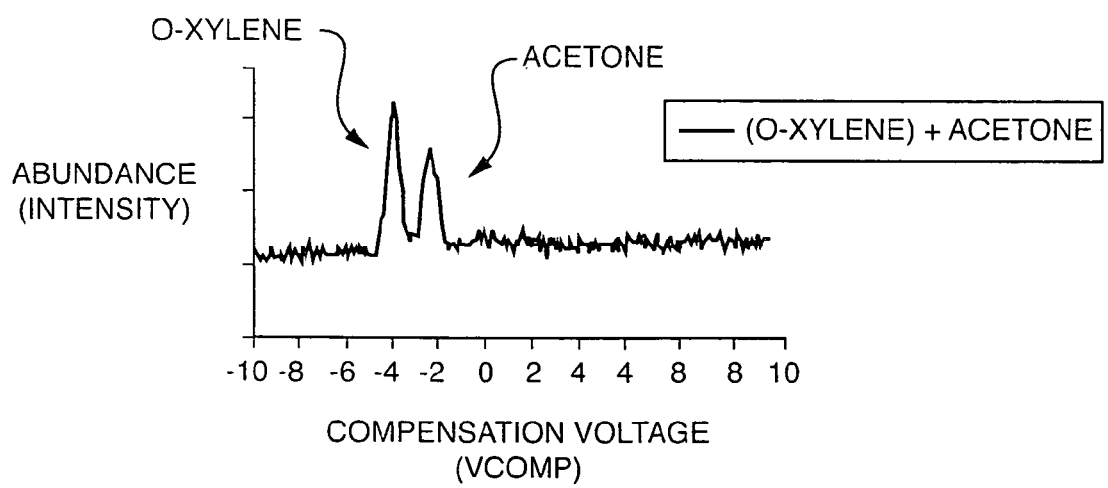
Figures 2A, 2B:
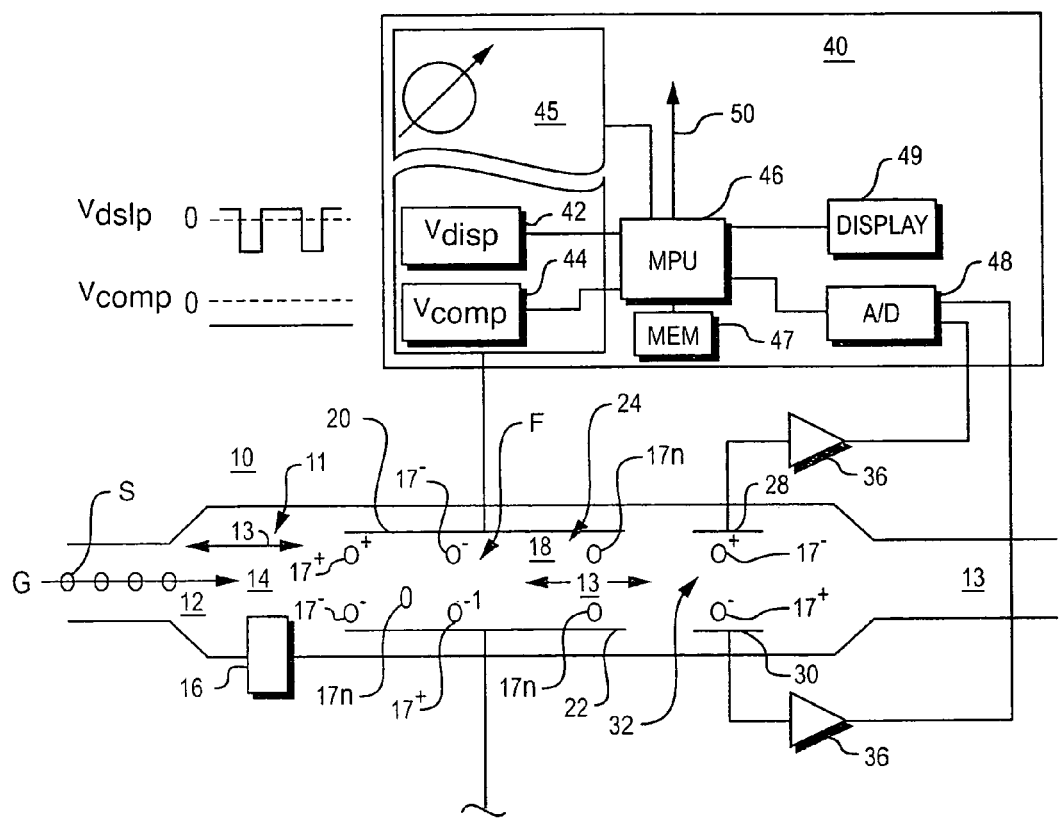
FIG. 2A is a schematic of a differential ion mobility spectrometer in accordance with an embodiment of the present invention.
FIG. 2B shows a curved filter electrode embodiment of the present invention.
Figure 2C:
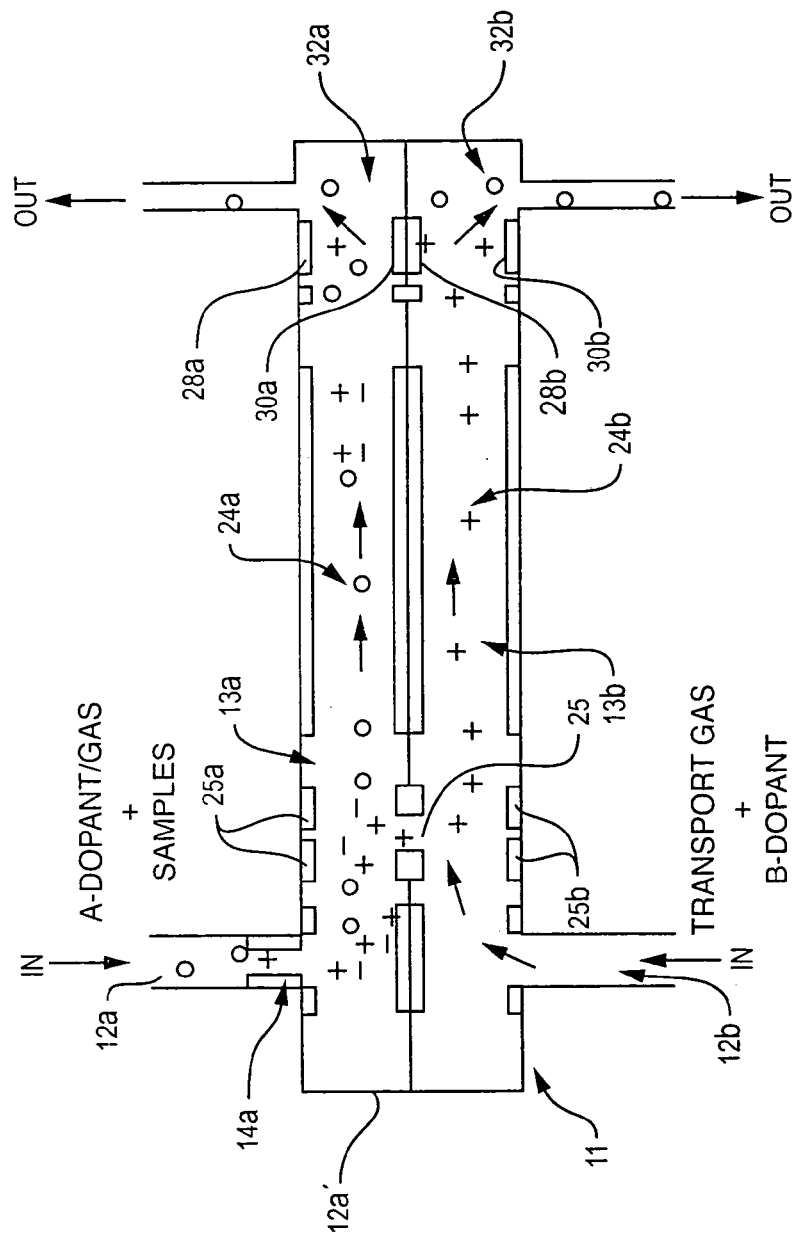
FIG. 2C is a multi-channel differential ion mobility spectrometer in accordance with an embodiment of the present invention.

Illustrative DMS embodiments of the present invention are shown in FIGS. 2A, 2B, and 2C. In the embodiment of FIG. 2A, apparatus 10 has an inlet 12 that accommodates the flow of a carrier gas G carrying sample S into the device and then along flow channel 13. The sample is drawn from the environment or received from a front end device, such as a gas chromatograph, and flows from inlet 12 to ionization region 14 along the flow path.

Compounds in the sample are ionized by an ionization source 16 as the sample flows through ionization region 14, creating a set of ionized molecules 17+, 17−, accompanied by some neutral molecules 17n of various chemical species. Ionized monomers and/or dimers are created during such ionization. Also clusters of ions may be created when a monomer combines with water molecules or other background molecules, in an ionized combination.

The ions are carried by a gas stream (sometimes referred to as a carrier gas) through stages of the system (e.g., into filter 24 and to detector 32), such as taught in U.S. Pat. No. 6,495,823, incorporated herein by reference. Alternatively, the sample may be conveyed via electric field, with or without carrier gas, as taught in U.S. Pat. No. 6,512,224, incorporated herein by reference.

In the embodiment of FIG. 2A, carrier gas G carries the ions into analytical gap 18 between filter electrodes 20, 22 of ion filter 24. A compensated asymmetric RF filter field F is developed between the ion filter electrodes in the analytical gap between the electrodes (e.g., 0.5 mm). The strength of the field varies according to the applied RF voltage (Vrf) in the gap.

In the embodiment of FIG. 2A, a detector 32 is on-board system 10 and takes the form of at least one electrode, and preferably includes a plurality of electrodes, such as opposed electrodes 28 and 30, associated with the flow path downstream of filter 24. The detector may be of various kinds, whether as complex as a mass spectrometer or as simple as opposed electrodes as shown in FIG. 2A. As well, in another embodiment, the detector is ccd-based which provides improved ion detection sensitivity. In yet another embodiment, the invention improves species separation as a front end to other processes, and does not require a detector.

Control unit 40 preferably performs a number of important actions in accordance with the present invention, and may incorporate various devices or functions for this purpose. These may include RF voltage generator 42, compensation voltage generator 44, a microprocessor unit (MPU) 46, memory 47, an analog-to-digital converter 48, and display 49.

Microprocessor 46 provides digital control signals to the RF voltage generator 42 and optional compensation voltage generator 44 to generate the desired compensated drive voltages for filter 24. These devices may also include digital-to-analog converters and the like, although not shown in detail.

In the embodiment of FIG. 2A, control unit 40 biases and monitors the electrodes 28, 30 of detector 32. Microprocessor 46 correlates applied compensation and RF voltages with observed responses at detector 32, via analog-to-digital converters 48. By comparing an observed response of, for example, peak detection intensity for a particular ion species at least two data points selected according to principles of the invention, the microprocessor 46 can identify particular compounds by comparison with a library of data stored in its memory 47. The result of the comparison may then be announced at an appropriate output device such as a display 49, or may be provided by electrical signals through an interface 50 to other computer equipment.

Apparatus of the invention are very stable and test results are repeatable. Therefore, in a preferred practice of the invention, we use the history table (lookup table) for species of ions that have been detected as correlated with compensation, RF and other field conditions, which enables use of the device for identification of detected chemicals. It is also within the scope of the invention to calibrate the system using the reactant ion peak (RIP) or a dopant peak, for example, among other techniques.

It will be appreciated that ions are separated based on differential mobility in the filter field F in the analytical gap 18 according to existing field conditions. Field F can be held at a fixed value, wherein the system is dedicated to detection of a particular ion species at a single data point, or the field conditions can be varied for generation of a plurality of data points. As well, a particular field parameter can be scanned to generate a mobility scan, wherein field conditions are set to a particular value except for at least one mobility-affecting parameter that is swept through a range so as to generate a mobility spectrum for the sample under test. This is performed under direction and control of control unit 40.

The embodiment of FIG. 2A has a flow path with generally flat contour. This is shown by way of illustration and not limitation. The present invention is not limited to flat plate configurations and may be practiced in other configurations, including, among others, radial, coaxial and cylindrical DMS devices. For example, an illustrative DMS having curved flow path 13' between curved filter electrodes 20', 22' (which may include curved plate electrodes or concentric cylindrical electrodes, among others) is shown in FIG. 2B, and an illustrative multi-channel embodiment 11 is shown in FIG. 2C (discussed below regarding use of dopants).

Simultaneous Analysis Modes

Another feature of the apparatus of FIG. 2A is that both positive and negative ion species can be analyzed simultaneously. Normally, a single channel APCI spectrometer detects ions of either positive or negative ion species in any one operating period, but not both simultaneously. If a single sample supplies both positive and negative ions, then multiple detections must be run seriatim for a complete analysis in a single channel system. Obviously multiple systems can be run simultaneously but this is both expensive and impractical.

Embodiments of the present invention overcome this limitation with various strategies based on ion flow design. For example, spectrometer 10 of FIG. 2A can generate, filter and detect both positive and negative ions simultaneously. These positive and negative ions can be related to the same or different chemicals in the sample. This simultaneous functionality is set forth in copending U.S. patent application Ser. No. 10/187464, filed Jun. 28, 2002, which is a continuation-in-part of U.S. patent application Ser. No. 09/896,536, filed Jun. 30, 2001, entitled "Apparatus For Simultaneous Identification Of Multiple Chemical Compounds," both of which are incorporated herein by reference.

We refer to detection of ions as detection modes: i.e., as positive detection mode (or positive ion mode, or, simply, positive mode), when positive ions pass through the filter and are attracted and detected by a negatively biased detector electrode, and negative detection mode (or negative ion mode, or, simply, negative mode), when negative ions pass through the filter and are attracted and detected by a positively biased detector electrode. Having both electrodes 28, 30 in detector 32 enables simultaneous detection of positive and negative ion species simultaneously passed by filter 24.

More particularly, as shown in FIG. 2A, positive and negative ions 17+, 17− are generated in ionization region 14 and are introduced into filter 24 (within analytical gap 18). If these ions have different mobility under a given set of compensated RF field conditions, then just the 17+ or 17− ions will be passed by the filter while all other ions will be neutralized, as in conventional DMS. This passage defines the passed ions as a single-polarity ion species.

Detection will proceed at a detector electrode. In this embodiment, if electrode 28 is positively biased, then it will attract ions 17− which will be detected upon their contact with the electrode. If electrode 28 is negatively biased, then it attracts ions 17+ which will be detected upon their contact with the electrode. Electrode 30 may be used in a like manner. The charge deposits at electrodes 28 or 30 are amplified by respective amplifiers 36 and 38, to provide detection data for use in control unit 40 for identification of the detected ion species. We call this a single mode detection.

However embodiments of the present invention are also capable of dual mode detections, having dual detector electrodes. In fact, when performing a mobility scan on a sample we can detect negative and positive ions passing through the filter within a single mobility scan. We refer to this process as "dual" or "simultaneous" detection because both positive and negative ions can be detected in one scan. The two detection modes include: positive detection mode where peak intensity associated with detection of positive ions passing through the filter is detected and negative detection mode where peak intensity associated with detection of negative ions passing through the filter is detected; these detections may be simultaneously displayed. In practice, it is the output of each detector electrode that is monitored to generate the positive and negative mode mobility peaks (i.e., spectra).

Furthermore, this simultaneous detection within one scan also includes the case where positive and negative ions are of such similar mobility under the same set of compensated field conditions that both are passed simultaneously through filter 24 as one "mobility species". Nevertheless, these ions do not interfere and their peaks do not overlap in the practice present invention because an additional separation step occurs at the detector. This additional separation step takes the form of having biased detector electrodes that separate the ions by polarity.

Thus preferred embodiments of the invention incorporate a dual mode, simultaneous detection capability. The embodiment of FIG. 2A is configured to distinguish between and to detect dual ion modes. For example, if electrode 28 is positively biased, then it attracts ions 17− and repels ions 17+ toward electrode 30. If electrode 30 is negatively biased, then it attracts ions 17+ while repelling ions 17− toward electrode 28. Thus this final stage of separation separates ions by depositing their charges on the appropriately biased detector electrodes 28 or 30, which may occur simultaneously. These charge deposits at electrodes 28 and 30 are amplified by respective amplifiers 36 and 38, which may be operated simultaneously, to provide detection data for use in control unit 40 for identification of both modes of the detected ion species, simultaneously from a single compensation scan.

It is further noted that some single chemical species may form both positive and negative ions. For example a complex molecule may fragment under test conditions. The negative mode spectra may be the same or different from the positive mode spectra depending upon mobility, on positive and negative ions and fragmentation. Thus we can use the data from both modes in a single detection scan to better identify the totality of detected chemical(s). This is beneficial even where species ions only are detected in one or the other mode, since the fact of presence and absence of data assists in species specific identifications.

It will therefore be appreciated that detection of both polarity modes in a sample analysis yields additional information in ion detection and identification. Furthermore, simultaneous detection makes this process faster and simpler than running multiple detections. This increased data can result in reduced false positives, leading to a higher level of confidence in compound identification.

Figure 3:
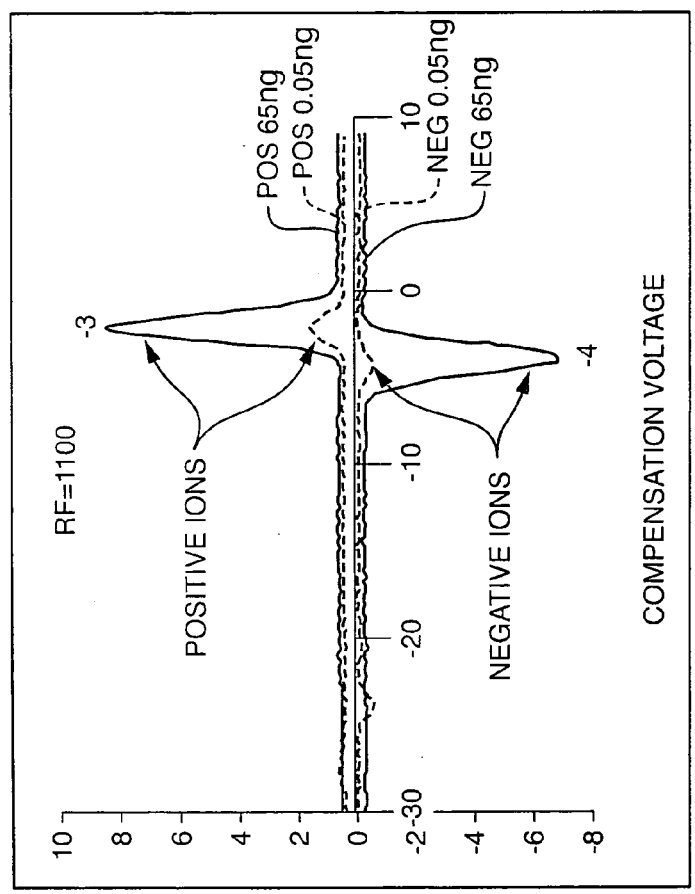
FIG. 3 shows positive and negative mode detections for methyl salycilate in an RF field operating at Vmax of 1100 v, in practice of the invention.

As an example, in FIG. 3, we show positive and negative mode detections for methyl salycilate in an RF field operating at Vmax of 1100 v. Ionization of methyl salycilate produces negative and positive ions, but conventional spectrometers on detect only one or the other mode at one time. In the present invention, both modes can be detected and displayed simultaneously, enabling faster an more reliable detection based on these multiple data detections. Detection of either mode may be the basis of identification of the ionized methyl salycilate based on resort to a lookup table (library) that includes relevant detection data. But a more reliable identification is made by comparing the detection data for both positive and negative mode detections. In a preferred practice of the invention, this occurs simultaneously. This dual mode aspect of the invention enables improved species identification based on multiple detection data.

Enhanced Species Discrimination By Control of Waveform Parameters of Filter Operating Conditions:

In practice of the present invention, we can optimize ion species analysis by making any one of several adjustments to operating conditions and making multiple detections. Making of these adjustments may be described in operational terms as making adjustment to "knobs" 45, FIG. 2A, associated with such properties. Nevertheless, we divide these parametric adjustments into two categories: electrical and environmental.

Electrical adjustments include adjustment to waveform characteristics such as field strength, DC compensation, frequency, duty cycle, and/or asymmetry, for example. Environmental adjustments include adjustments to pressure, flow rate and gas composition, including use of additives or dopants that enhance ionization efficiency (such as for UV ionization) or to produce free electrons for production of negative spectra, and also includes use of dopants for peak shifting.

These system adjustments are made for specific purposes to achieve prescribed results, based upon knowledge of the affect these parametric adjustments will have on system performance and analyte behavior. With such knowledge and the fact that we identify an ion species with multiple data points, our species identifications are highly accurate with minimized false detections.

In the prior art, ion species have been identified by selecting Vmax and Vc and detecting species passing through the filter field, or selecting Vmax and scanning Vc to obtain a mobility scan of the sample. Compounds can be identified according to this process. However, species whose spectra overlap can defy accurate identification. Peak shifting techniques of the invention enable separation of such hidden or overlapping peak information.

For a given ion species in a sample, as the amplitude (Vmax & Vmin) of the asymmetric RF voltage changes, the amplitude of the DC compensation voltage (Vc) required for passage of that species through the filter field will also change. The amount of change depends upon the species involved. However, there is still the problem of separation and identification of several overlapping spectra. Furthermore, making a first detection and changing one field parameter alone is inadequate for improving species discrimination, as such single change would retune the field for detection of a different species rather than improving separation between detected species and being able to isolate and redetect the same species.

Thus, in practice of the present invention, an ion species is identified by making a provisional detection and causing and observing predicted behavioral changes of ion species under selected operating conditions. This process benefits from "adjusting the knobs" and creating and using multiple data points to support a species identification.

In an illustrative embodiment of the present invention we improve accuracy of species identification by detecting and provisionally identifying at least one ion species, typically one out of several ion species with overlapping spectra, at a first set of filter operating conditions. We then selectively change these operating conditions based upon knowledge of the first detection and upon predicting the affect such change will have upon the behavior of such provisionally identified species. Then we confirm the provisional species identification by detection of the predicted species behavior. With this plurality of purposefully related data points we access our stored detection data and make a species identification. (The techniques of data storage and access are well-known.)

In a special embodiment of the invention, a device is dedicated to detection of a prescribed analyte and detection is made at a prescribed set of operating conditions. Then positive and negative detection mode data, and/or data from detection at a second set of prescribed operating conditions, is used for species identification according to the invention.

Thus it will be appreciated that in a preferred practice of the present invention we improve species identification by improving separation between analyte peaks. We do this by controlling or manipulating aspects of the filter operating space. We decide which parameters to adjust based on known species behavior. The spectrometer can scan a spectrum and once a species is detected and provisionally identified then a second detection is made to verify such provisional identification. We can also set the spectrometer to detect a given species or class of species in this multi-step process of the invention.

In an illustrative practice of the invention, we note detection peak characteristics (such as polarity, peak, location, intensity, width, etc.) at a first set of operating conditions (noting ionization source, dopant level if any, and other electric and environmental field parameters, including Vmax, Vmin, Vc, RF frequency, and duty cycle). We then change at least one mobility-affecting parameter in the operating conditions (such as adjusting dopant level, Vmax, Vmin, Vc, RF frequency, duty cycle, etc.) and note changes in peak characteristics (such as location, intensity, width, etc.) at the second set of operating conditions. This collected data is compared to a lookup table of detection data for known compounds in such conditions. Upon data match, a species identification is made with a high degree of reliability. In the preferred practice of the invention, we make the second detection at a second set of operating conditions that is selected according to knowledge of the first set of operating conditions and the first detection results.

As will now be understood, we selectively make adjustments to the filter. These adjustments are made in terms of waveshape, Vmax, the ratio of Vmax/Vmin, DC compensation, frequency, duty cycle, and/or aspect of asymmetry, and in terms of other environment variables like pressure, flow rate, gas composition, moisture, ionization process, and/or presence and level of doping. The result is improved species separation and improved species identification.

Waveform Adjustments—Background Spectra

In any sample, there may be several spectra generated, including those based on low level background impurities in background spectra), components of the carrier gas (oxygen, nitrogen, etc., generally referred to as RIP), and analyte spectra.

Figure 4:
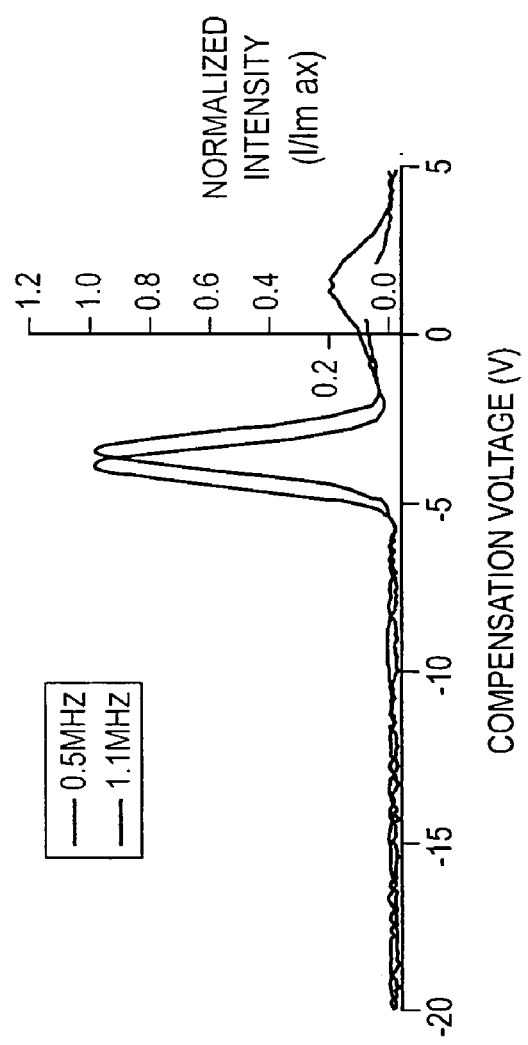
FIG. 4 shows the effect of frequency on positive mode background spectra, in practice of the invention.
Figure 5:
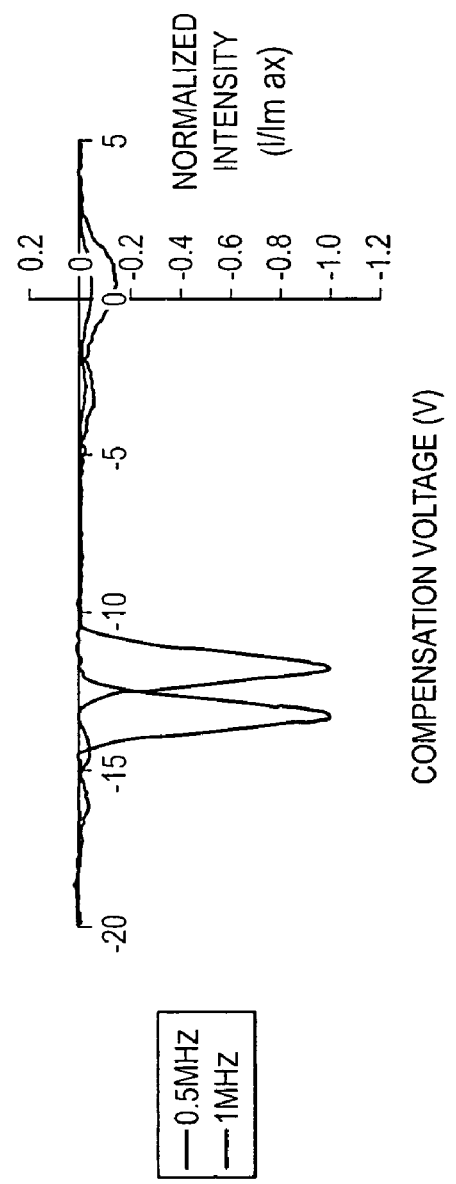
FIG. 5 shows the effect of frequency on negative mode background spectra, in practice of the invention.

FIG. 4 and FIG. 5 show a comparison of effect upon detected background spectra, sometimes referred to as RIP, upon switching between two RF frequencies 0.5 and 1.1 MHz. The effect of variation in frequency on background spectra shows that for lower frequency (0.5 MHz) the RIP peaks for both positive (FIG. 4) and negative (FIG. 5) ions are located on the higher absolute values of compensation voltage (|−Vc|). This demonstrates that changes in frequency correlate with changes in RIP, which may be applied for example when attempting to separate peaks located near the RIP. This also demonstrates that without changing other parameters, a characteristic spectra shift ($\Delta Vc$) can be attributed to the RIP when switching frequencies. This can be used to confirm detection of the RIP peak(s).

Thus in one illustrative method of the invention, such as shown in FIG. 4, a scan is performed with RF at a first frequency, such as at 1.1 MHz at a Vmax such as at 660V. A positive mode peak is detected at a first Vc (such as at −4.0). We then redetect the peak at a second frequency, such as at 0.5 MHz, and note peak location, such as at a second Vc of about −4.5, also in the positive mode. The change of Vc, between the first and second Vc indicate shift of an RIP peak, since analyte ions will respond differently. This detection process identifies the RIP and will enable separation of background spectra from analyte spectra during analysis of a chemical sample.

It will be appreciated that this detected data must be correlated with stored data for identification of the detected species. In this example, the background spectra can be identified based on stored data representative of background spectra in that device and can now be separated from analyte data to be collected and identified in that device.

In the identification process of the invention, use of positive mode data of FIG. 4 can be augmented with use of negative mode data (FIG. 5 shows negative mode data, i.e., data representing detection of negative ion species for samples of FIG. 4). These data can be detected simultaneously in practice of the apparatus of the invention, however, they can also be performed in sequence. In this case, the data set of FIG. 4 was gathered in a field having a Vmax of 660 v, while in the second data set, FIG. 5, the background spectra was detected in a field set with a Vmax of 520 v.

Choice of multiple Vmax values illustrates that more than one variable can be adjusted in practice of the invention, for example, with changes in both frequency and in field values. This follows because we predict a second data point based on first provisional identification without requiring linearity or other limits on changing parameters as long as a second definitive set of data (e.g., characteristic peak shift) can be generated to verify the first species detection.

Turning to FIG. 6A & FIG. 6B one can see that there are no differences in peak position at the low RF voltages (low field strength) for the RIP for the two frequencies shown. Peak shift due to frequency change is discernable at the voltages higher than about 500V, evidencing higher field strengths.

Peak intensity is sensitive to frequency change. In FIG. 6C and FIG. 6D one can see that there are differences in peak intensity even at low RF voltages. This likely results from having a small gap between the filter electrodes (e.g., gap width of 0.5 mm in one practice of the invention). With a small gap, with decreasing frequency and increasing excursion time, more ions can reach the channel walls and be neutralized. This effect increases as the RF increases. According to FIG. 6D, in these conditions the intensity of lighter negative RIP ions (mostly oxygen) decreased more, faster and disappeared at 600V for the lower frequency and 650V for the higher 1 MHz. The heavier positive ions ($H_2O/nH^+$) can survive at higher voltages, e.g., 650V (FIG.

6C), but again peak intensity was less for the lower frequency than for the higher 1 MHz.

These findings are important as they can be applied to improved detection of analyte ions in a chemical sample, by further enabling knowledgeable separation of RIP and background spectra from analyte spectra according to responses to applied changes. Collection of data for background and analyte spectra enables creation of a table of data for use in species identification.

Figure 7A:
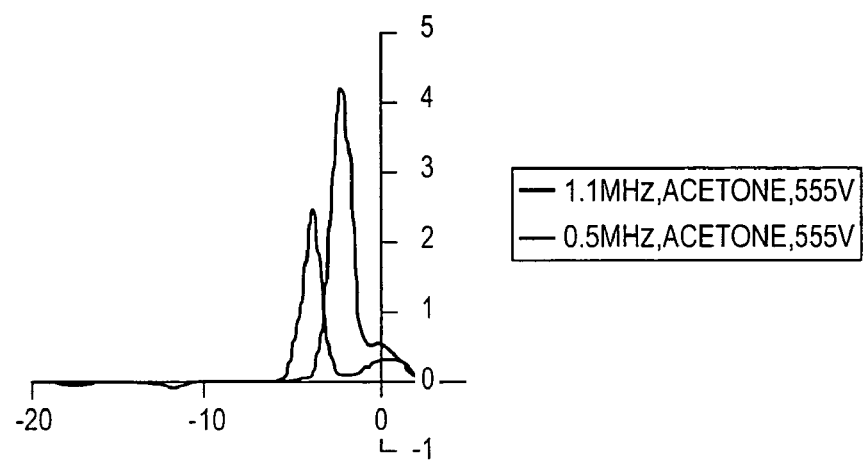
FIGS. 7–8 show the effect of frequency and of electric field strength on positive (A) and negative (B) acetone ion peaks, in practice of the invention.
Figure 7B:
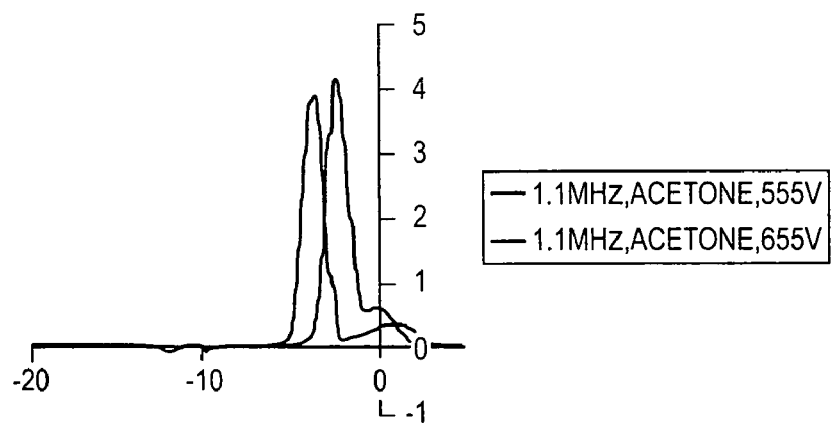

FIG. 7A shows the effect of changes in frequency on the positive detection peak position for acetone at two frequencies 0.5 and 1.1 MHz for a field having a Vmax of 555 v. Note that as the frequency decreases so does the required compensation. FIG. 7B shows the effect of changes in electric field strength (Vmax of 555 v and Vmax of 655 v) for a DMS filter operated at 1.1 MHz for acetone positive mode peaks in practice of the invention. Note that as the RF field increases so does the required compensation. It will be appreciated that these are characteristic detection data which can be stored for later use in identification of detected ion species in the apparatus of the invention.

Figure 8A:
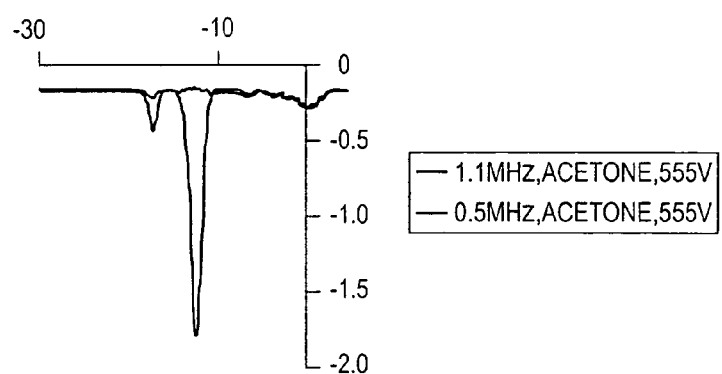
Figure 8B:
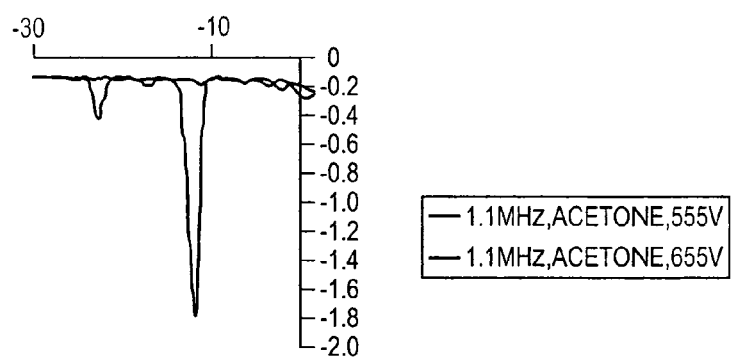

It will be further appreciated that ionization of acetone not only produces positive ions but also releases free electrons. These free electrons are expected to be captured by species with high electron affinity. FIG. 8A shows the effect of changes in frequency on the negative detection peak position for negative spectra having received free electrons from ionization of acetone at two frequencies, 0.5 and 1.1 MHz, for an RF field having a Vmax of 555 v. FIG. 8B shows the effect of changes in electric field (Vmax of 555 v and Vmax of 655 v) at 1.1 MHz for the negative spectra. Comparing peaks teaches that, for the higher field, the required compensation is increased significantly. This increased peak separation, measured as changes in Vc, significantly assists in species identification in practice of the invention.

Thus it is clear that controlled changes in frequency generate controlled and predicted changes in known analyte behavior and can be applied in a species separation and identification process of the invention. In the case of any ionized analyte, these known responses in mobility behavior, such as changes in field strength or frequency, are the basis for assembling stored data which is then used in identifying detection spectra. Additional stored data can be assembled for additional characteristics and additional analytes.

Figure 9A:
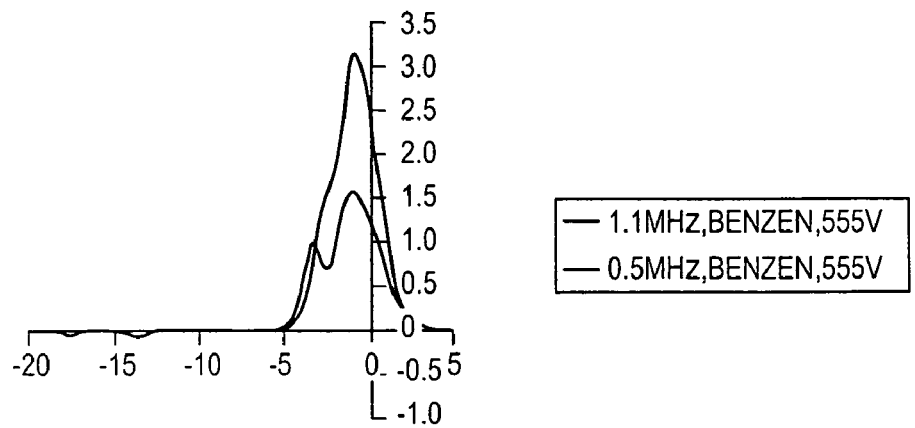
FIGS. 9–10 show the effect of frequency and of electric field strength on positive (A) and negative (B) benzene ion peaks, in practice of the invention.
Figure 9B:
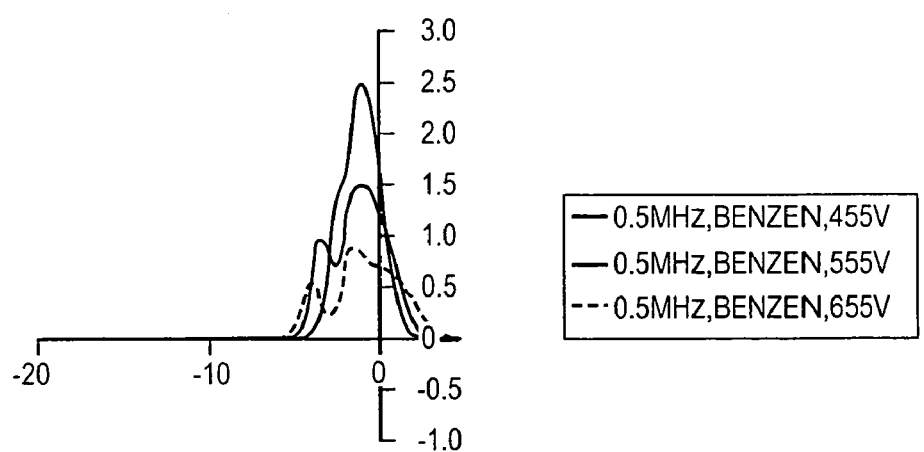

It will be appreciated that various analytes can be characterized in this manner. For example, FIG. 9A shows the effect of changes in frequency on the positive detection peaks for benzene at two frequencies, 0.5 and 1.1 MHz, in an RF field having a Vmax of 555 v; note that the lower frequency peak now has revealed additional information as a second peak. In FIG. 9B, effect in changes in field strength shows that the higher field at 555 v reveals a second peak as against the single peak of the lower field at 455 v.

Figure 10A:
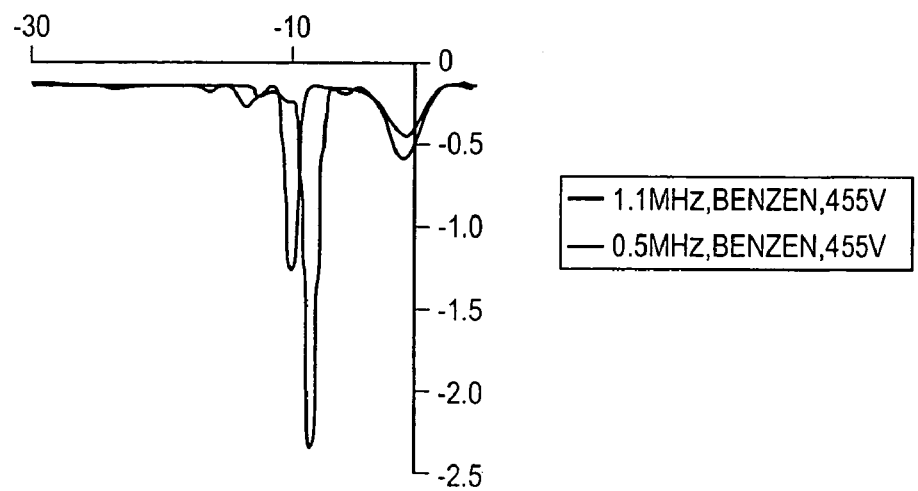

FIG. 10A shows the effect of changes in frequency on spectra for negative species related to ionization of benzene (i.e., species which have received free electrons released from ionization of benzene) at two frequencies 0.5 and 1.1 MHz for an RF field having a Vmax of 455 v. A substantial peak is detected at the higher frequency while the peak is attenuated at the lower frequency at higher compensation Vc. This additional compensation represents increased peak shift. Knowing this effect, peak shift, when properly induced, enables separation of species and improved species identification.

Figure 10B:
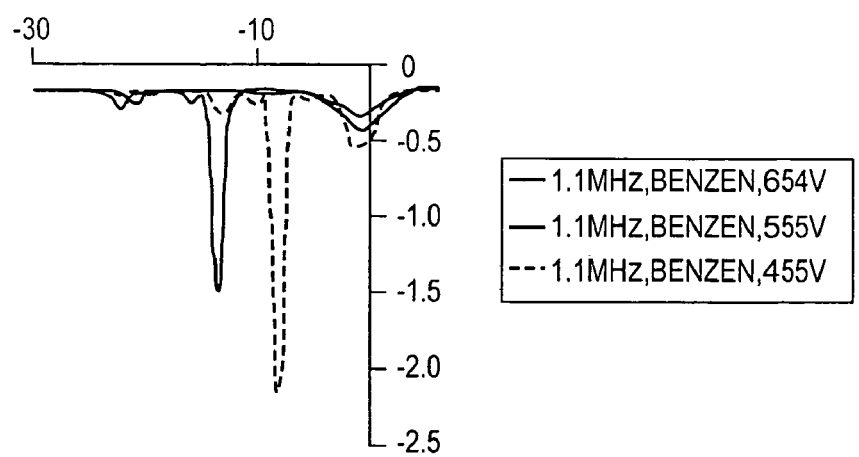

FIG. 10B shows the effect of changes in electric field strength upon negative detection peaks related to ionization of benzene (i.e., species which have received free electrons released from ionization of benzene) in RF fields having Vmax of 455 v and 555 v at 1.1 MHz. There is a first peak at 455 v and a lower peak shifted in compensation at 555 v.

Figure 11A:
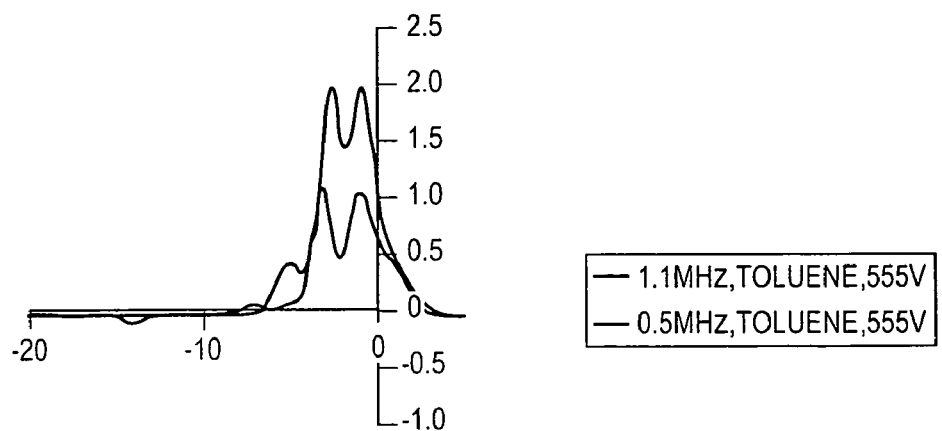
FIGS. 11–12 show the effect of frequency and of electric field strength on positive (A) and negative (B) toluene ion peaks, in practice of the invention.
Figure 11B:
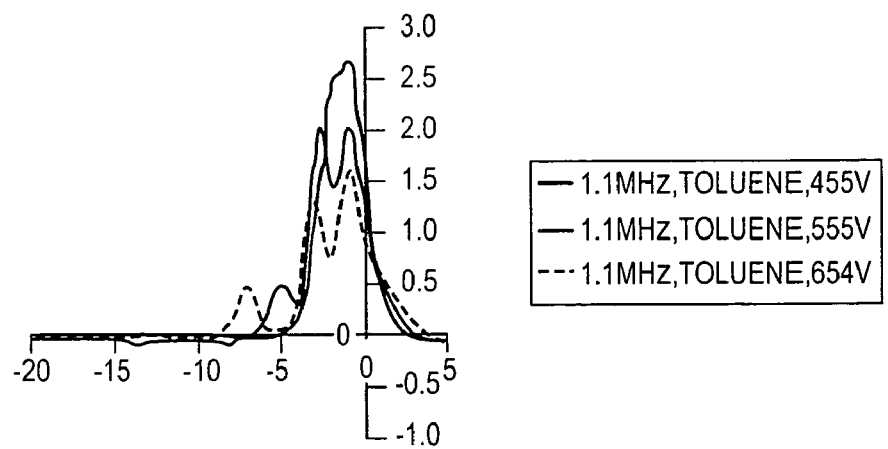

As a further example of peak shift, FIG. 11A shows the effect of changes in frequency on the positive detection peaks for toluene at two frequencies, 0.5 and 1.1 MHz, in an RF field at Vmax of 555 v; note that the lower frequency peak is of lower intensity and is split into double peaks while the higher frequency peak has a more intense double and a small third peak at different compensations. FIG. 11B shows the effect of changes in electric field strength between Vmax at 555 v and at 655 v) at 1.1 MHz for toluene positive mode peaks in practice of the invention.

Figure 12A:
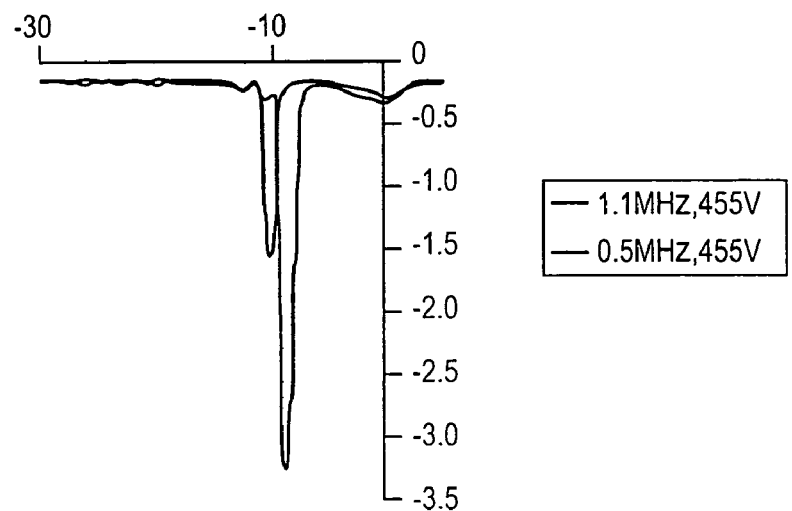
Figure 12B:
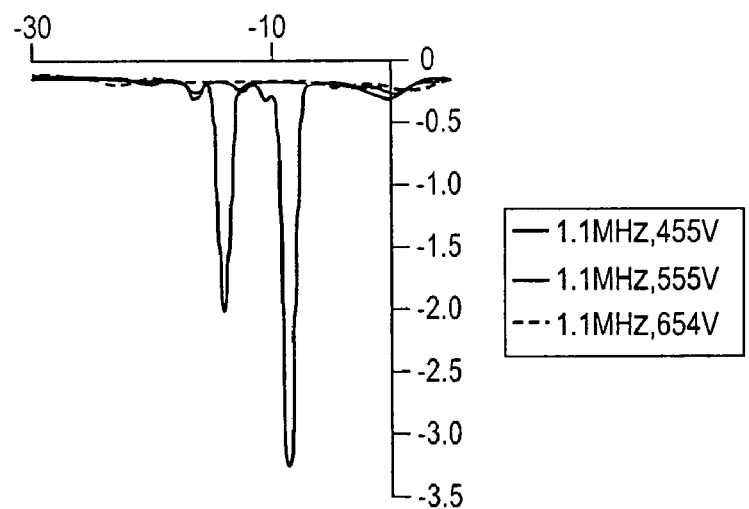

FIG. 12A shows the effect of changes in frequency on negative species related to ionization of toluene at two frequencies 0.5 and 1.1 MHz for an RF having a Vmax of 455 v. A substantial peak is detected at the higher frequency while the peak is attenuated at the lower frequency at higher compensation. FIG. 12B shows the effect of changes in electric field upon negative detection peak position at Vmax at 455 v and 555 v for an RF field at 1.1 MHz. There is a substantial shift in peaks with the lower field peak having a higher compensation.

Once, again, it will be appreciated by a person skilled in the art that controlled changes generate controlled and predicted changes in analyte behavior and can be applied to replicate such behavior in a species separation and identification process of the invention. Thus simple and complex samples can be analyzed in practice of the invention. These tools enable manipulation of ion species to improve species analysis (separation, detection and identification). This is based on the fact that the level of change in $V_c$ and peak shape or intensity differ for different ion species for different field conditions and changes.

In practice of the invention, parameters of waveform characteristics, such as frequency, can be adjusted for discrimination of ion species. We can use the effect, such as varying RF frequency, as an alternative to or in combination with varying of field strength. Variation of frequency for a given RF intensity can also enable additional species separation according to mobility, weight, mass or structure. For example, in high frequency conditions the ion filter can pass a range of species, with good separation between heavier and lighter ions. In low frequency conditions only heavy ions will pass (lighter ions having enough time to neutralize on the electrodes will not pass). At low frequency, these heavier ions will be better resolved in comparison with high frequency conditions. For heavier ions, we use a high RF voltage and low frequency, in one practice of the invention, for improved species discrimination.

We can choose to vary frequency or other field parameters in generating species data. In the simplest case, we can adjust the field strength since this may affect ion species behavior. However, this change alone is not always adequate as a process control. Furthermore, a better measure of species dependence is the ratio of Vmax to Vmin for the particular RF field correlated with a given species behavior. This measure brings in attributes of the waveform asymmetry and its impact on ion species behavior in the filter.

In practice of the invention, the effect of RF field on the ion trajectory may be compensated with a variety of techniques. This may includes DC compensation or it may be provided by varying other aspects of the filter operating conditions, the effect of which is to perform a compensation function. An example of this includes adjustment of a parameter of the waveform, such as duty cycle.

Figure 13A:
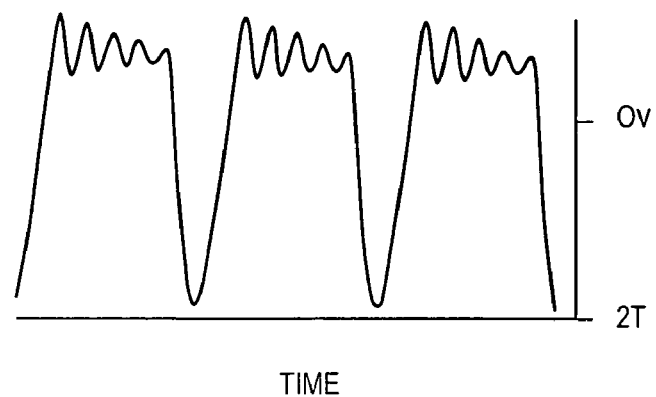
FIG. 13A–B show flyback and squarewave waveforms, in practice of the invention.
Figure 13B:
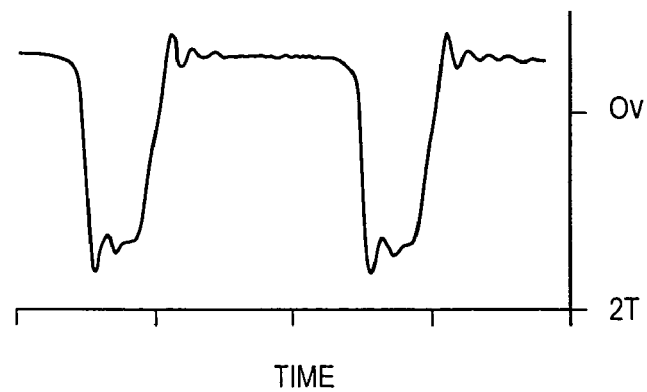
Figure 14A:
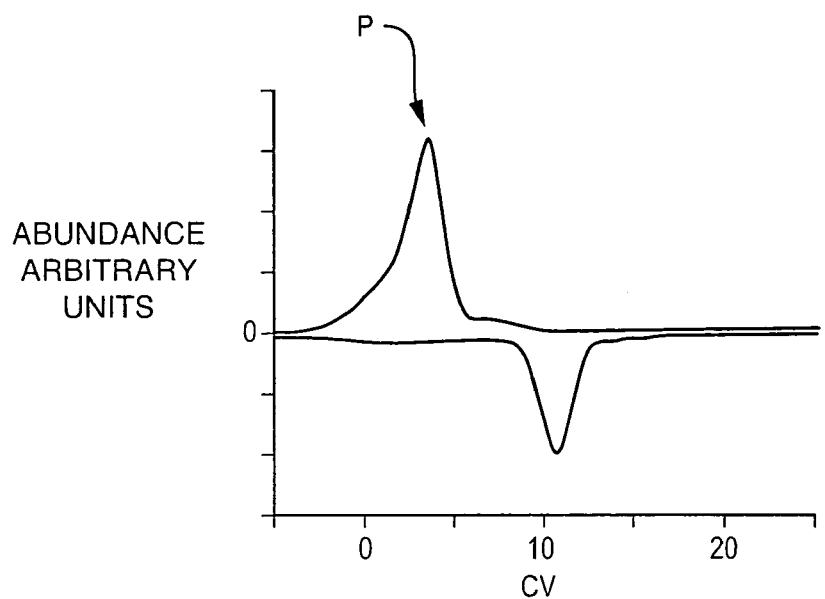
FIG. 14A–B show detection spectra corresponding to the waveforms of FIG. 13A–B, in practice of the invention.
Figure 14B:
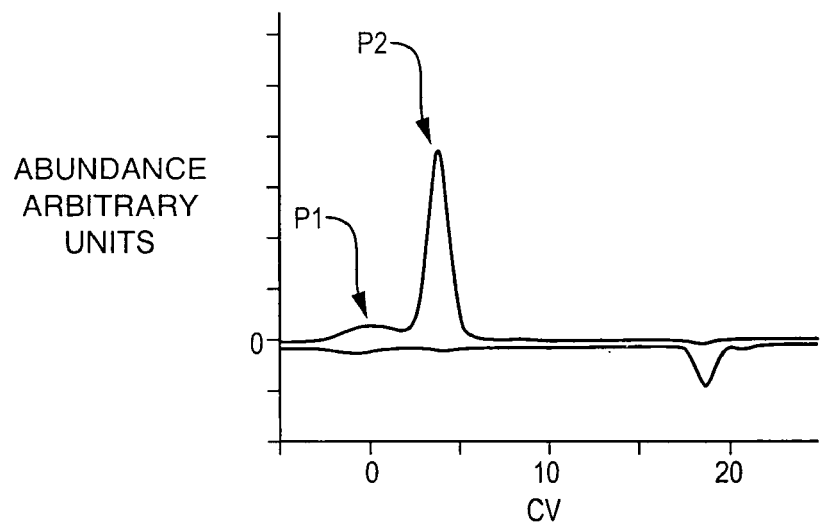

Different waveform shapes, such as different square waves will have an impact on species detection. A different waveform will elicit different mobility behavior for some species, as evaluated by the level of and changes in compensation. These are signature events that are noted and utilized in practice of the invention. An illustration is shown in FIG. 13 and FIG. 14, regarding use of two different wave shapes (i.e., flyback and square). In FIG. 13A a first waveform is shown, generated with a flyback generator, and is correlated with the spectra shown in FIG. 14A. The positive peak is fairly broad and represents background and analyte. In FIG. 13B, a square wave is shown which correlates with FIG. 14B, showing resolution of peak P into peaks P1, the unresolved analyte of FIG. 14A, and the background spectra peak P2. This discrimination is achieved even where other field conditions remain the same, showing that changes in waveform correlate with differential changes in compensation for different analytes in a sample. This differential behavior can be favorably used in practice of the invention to improve species discrimination and identification.

Figure 15A:
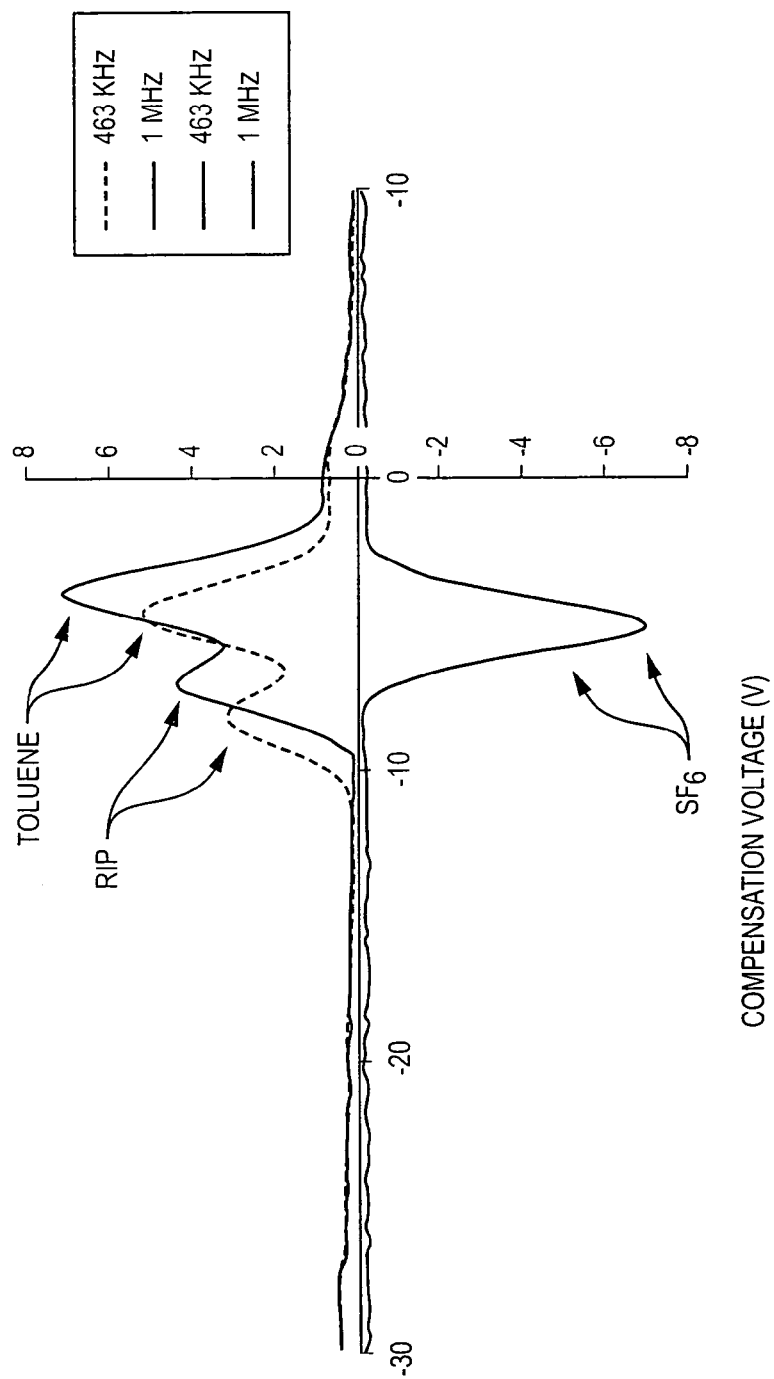
FIG. 15A, shows the effect of frequency of the RF voltage upon RIP, toluene and SF6 ion peaks, in practice of the invention.

While wave shape changes can be implemented as the above example teaches, other field changes can be imposed to increase species peak separation. In FIG. 15A we show a combination of positive and negative mode detections of a sample containing toluene dopant and SF6, and the affect upon the RIP, for detections at a fixed duty cycle of 0.2. Two detections are made, one at 463 Khz and the other at 1 Mhz. In the positive mode, the toluene and RIP are clearly discerned at both frequencies. SF6 follows the same pattern but in the negative mode. It is noted that in the positive mode, at the lower frequency, there is better separation between toluene and RIP peaks even though at lower intensity. It will thus be appreciated that this separation would be the type of ion species behavior response sought to be achieved in the second step of the presently disclosed process of the invention.

Figure 15B:
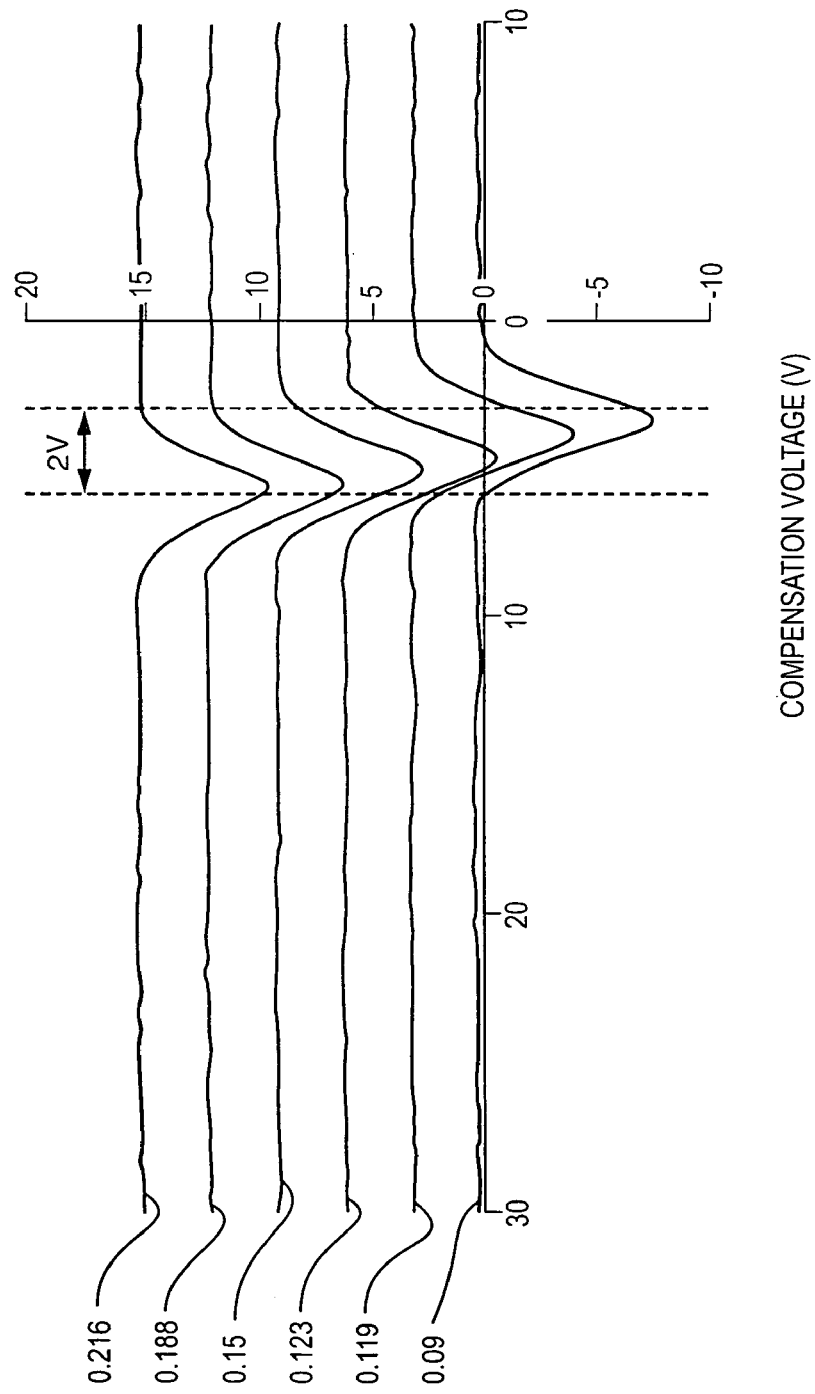
FIG. 15B shows the effect of duty cycle of the RF voltage upon SF6 ion peaks, in practice of the invention.
Figure 15C:
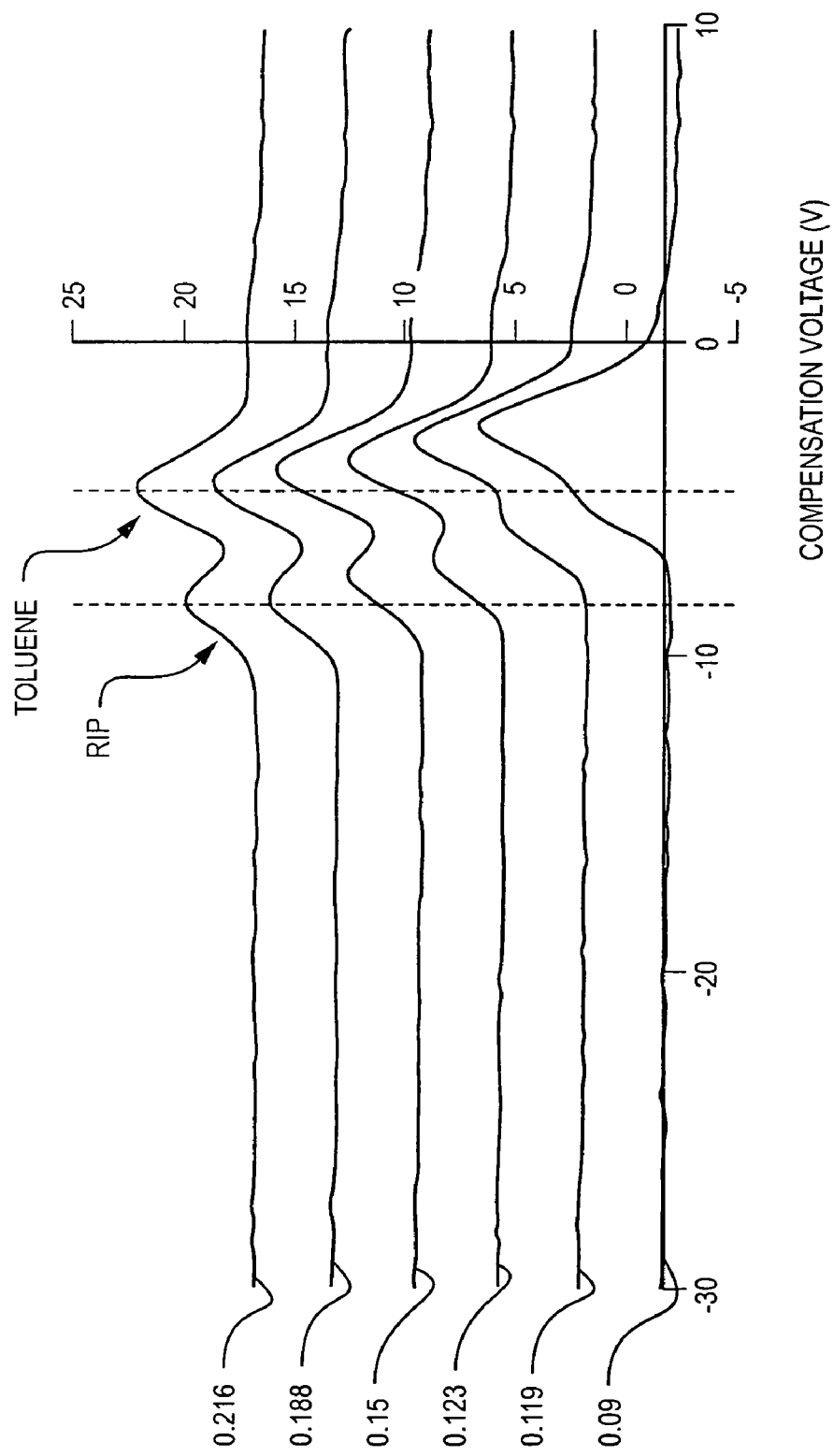
FIG. 15C shows the effect of duty cycle of the RF voltage upon RIP and toluene ion peaks, in practice of the invention.

Referring to the data of FIG. 15B and FIG. 15C, we demonstrate the useful affect that adjustment to duty cycle has on species analysis in practice of the invention. In FIG. 15B we show the effect of changing duty cycle of an RF Vmax at 692 at 463 Khz, for the negative spectra of SF6. Detections were made at six different duty cycles from low of 0.09 up to 0.216, showing a leftward shift (about 2 v) of the detection peaks. This is represented as stored data which then can be accessed to identify the SF6 spectra in an identification process of the invention.

In FIG. 15C we show effect of changes in duty cycle of an RF having Vmax at 692 at 463 Khz upon RIP and toluene peaks. Detections were made at six different duty cycles from low of 0.09 up to 0.216. The RIP and toluene peaks appeared to strongly overlap at the lower duty cycle but were well resolved at the higher duty cycle, even as the detection intensity decreased. Thus, again, practice of the invention suggests that analytical optimization can be counter-intuitive in that normally efforts are made to maximize detection intensity. Yet we have shown that more useful detection data is obtained even at a loss of signal intensity because it is used in the second step of the disclosed process to confirm the first data, rather than as absolute data on its own where intensity might be more critical.

Use of Dopant

We broadly define doping as the process of adding an analyte for the purpose of affecting ion species behavior. We use doping to assist in identifying analytes of interest. We define several forms of doping.

Doping may include the step of addition of an analyte in the ionization process whose ionization releases free electrons which enables ionization of negative species. Doping may include the step of use of an additive to improve ionization efficiency. Doping may include the step of addition of an analyte that affects species behavior and causes peak shift. We use these functions in practice of embodiments of the invention.

Ionization may be implemented through a variety of techniques, e.g., use of a radioactive source like $^{63}$Ni, an ultraviolet lamp, a plasma or corona discharge device, etc. Generally speaking, for successful ionization, the applied ionization energy must be at least as much as the energy of ionization for the molecule of interest. For example, a high source of energy is required (such as $^{63}$Ni) for direct ionization of molecules having high energy of ionization (such as SF6). However, in many circumstances it may not be possible to use a radioactive source to effect such high energy direct ionization.

In practice of one embodiment of the invention, we use a non-radioactive ionization source 16 (e.g., UV lamp) where the energy of ionization is less than the energy needed for direct ionization of compounds such as SF6. We introduce a dopant into the ionization path (e.g., into the influence of photo-ionization from a UV lamp) in the ionization region 14. In this arrangement, adequate energy is supplied to ionize a low-energy-of-ionization dopant (e.g., acetone, toluene or any substance with energy of ionization less than energy of photons from the photon source), which generates positive dopant ions and free electrons.

The dopant ions and free electrons are mixed with sample molecules. Molecules having a high electron affinity will be ionized by these free electrons. Thus molecules which normally cannot be ionized in UV can be ionized in practice of the invention. The resulting ions are then carried into filter 24 and detector 32 for detection and identification.

In a preferred practice of the invention, we introduce an adequate flow of dopant into the ionization region, at least enough that results in a large volume of doping ions filling the volume. This increases likelihood of ionization of the analyte molecules by charge transfer. Therefore this use of dopant enables ionization and detection of trace amounts of analyte in situations where otherwise they are likely to be missed, which results in increased detection sensitivity. In practice of the invention, the analyte ion peaks are detected and distinguished from dopant peaks.

Figure 16A:
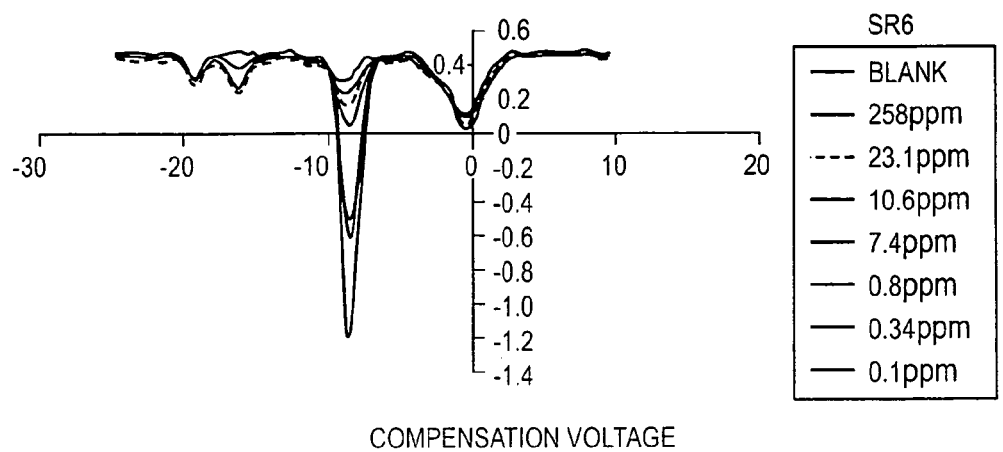
FIG. 16A–B show negative (A) and positive (B) spectra for different concentrations of SF6, in practice of the invention.
Figure 16B:
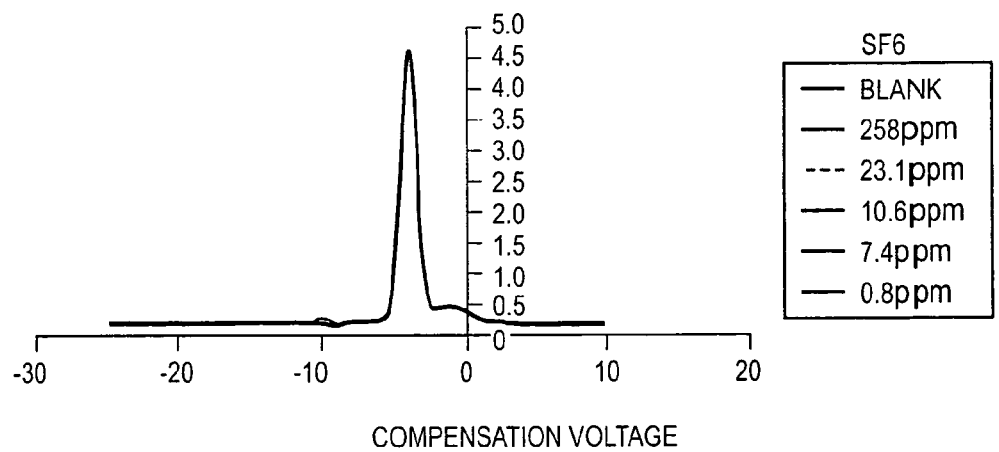

In one illustration, we use a dopant to improve ionization of SF6. Samples of SF6 were introduced along with a constant level of dopant (acetone) for UV ionization. The system was operated with RF voltage at 1130 v, with dry air (humidity at 10 ppm), at atmospheric pressure. FIG. 16A shows the negative mode response for different levels of SF6 concentration. It is clear that this detection mode is consistent (without peak shift) for varying levels of negative SF6 ions. FIG. 16B shows the positive mode response for the dopant used in this experiment, where, even with different levels of SF6, the positive spectra does not change. This is a direct reflection of detection of positive ions of the dopant and negative ions of the analyte (SF6).

This experiment demonstrates the power of using a low energy of ionization dopant (e.g., acetone) to ionize a high energy of ionization molecule (e.g., SF6) without requiring use of a high energy ionization source. Therefore we can use a non-radioactive ionization source (e.g., UV). We also benefit from the ability of using a detector (electrodes 28, 30 of FIG. 2A) having modes which may simultaneously distinguish between and detect both the analyte and dopant ions.

Single mode detection can be adequate for identification of ion species, such as SF6. Meanwhile, in the positive ion mode, there is no easily discernible SF6 peak as against the background spectra. But the absence of discernable detection in one mode has significance for SF6 identification. In other words, no other species has been detected. Thus positive and negative mode data may be collected in a scan, simultaneously, and the combination of presence and/or absence of various datum may be combined for a dual-mode analysis of the sample and identification of a detected chemical species, such as SF6, based on lookup functions (guided by control unit 40), according to an embodiment of the invention.

Figures 17, 18:
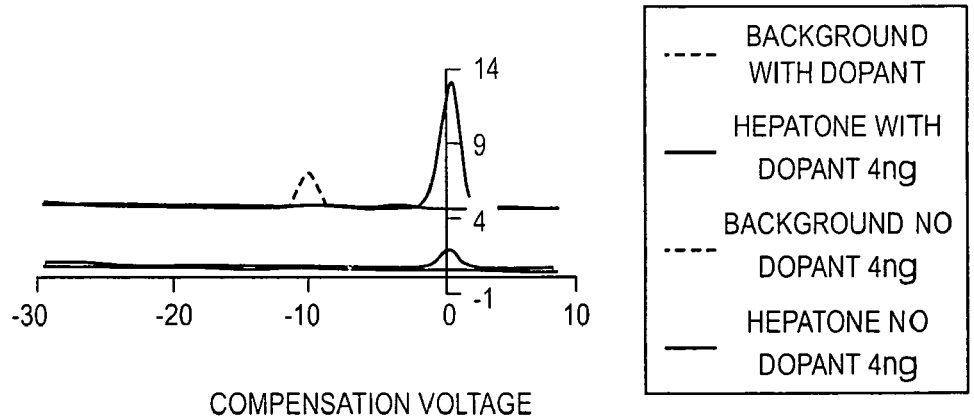
FIG. 17 omit.
FIG. 18 shows the effect of doping on heptanone ions, in practice of the invention.

We also use dopant to increase efficiency of ionization. In the example if FIG. 18, benzene dopant at 2 ppm was employed for UV ionization of heptanone. Spectra are shown for four scans, showing: background alone and with dopant and heptanone without and with dopant. Differences in peak detection and intensity are clear. The benefit of detecting heptanone with doping relative to detection of heptanone alone is demonstrated as increased detection signal. This results in increased sensitivity and selectivity in practice of the invention.

Figure 19:
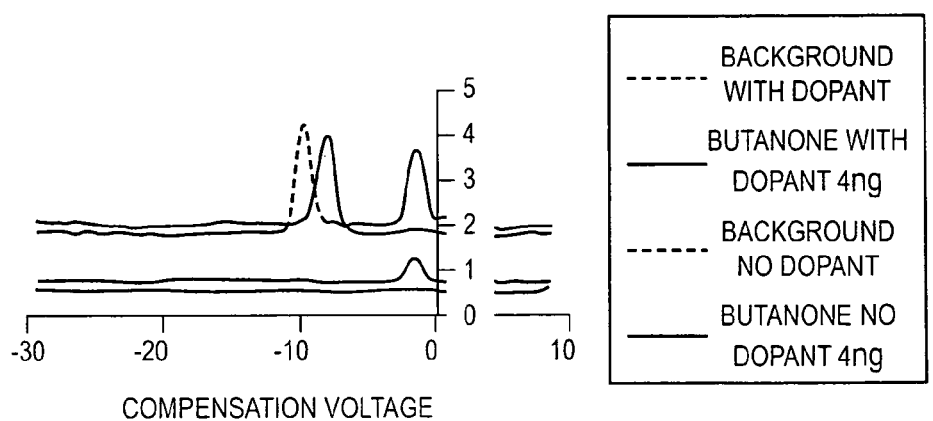
FIG. 19 shows the effect of doping on butanone ions, in practice of the invention.

FIG. 19 illustrates use of benzene dopant at 2 ppm for UV ionization of butanone. As seen in FIG. 19, spectra are compared for background alone and with dopant, and for undoped butanone and with dopant. Differences in peak detection and intensity are clear. The benefit of detecting butanone with doping relative to detection of butanone alone is demonstrated as increased detection signal. This results in increased sensitivity and selectivity in practice of the invention.

Figure 20:
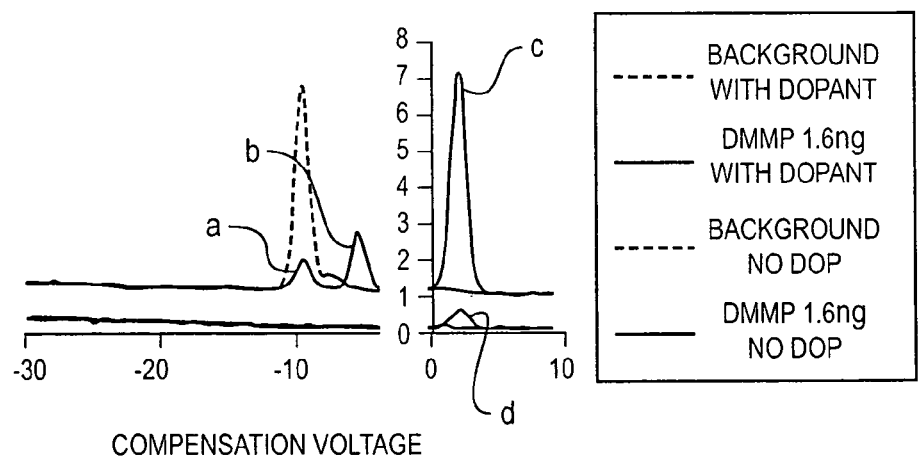
FIG. 20 shows the effect of doping on DMMP ions, in practice of the invention.

FIG. 20 illustrates use of benzene dopant at 2 ppm for UV ionization of DMMP. As seen in FIG. 20, spectra are compared for background alone and with dopant, and for undoped DMMP and with dopant. Differences in peak detection and intensity are clear. In this case, the benefit of using doping relative to detection of DMMP alone is demonstrated. In FIG. 20, the scan of DMMP sample with benzene dopant produces three peaks "a", "b", "c". Peak a relates to detection of background spectra, while peaks b and c relate directly to detection of DMMP. Peak "d" is a minor peak for DMMP detected without doping.

The three peaks a, b, c for doped DMMP is a signature constellation related to DMMP. If detected under these conditions it can be compare against stored data for positive DMMP identification. Note that this constellation of peaks and their locations, is different for the signature for doped heptanone and butanone in FIGS. 18, 19. Such stored data can be accessed accordingly for species identification.

But the DMMP can be identified against its own data, regardless of comparison to spectra for other analytes. For example, the small peak d for DMMP without dopant might be confused with detection of several similar analytes (e.g., butanone and heptanone). However, once that peak is detected, a dopant can be supplied (e.g., benzene at 2 ppm) and resulting spectra can be obtained (e.g., spectra a, b, c FIG. 20) enabling accurate identification of DMMP with a high degree of confidence.

Thus in a multi step process of the invention, results of a detection without doping suggest system changes for a second detection. For example, detecting peak d suggests a group or class of analytes (in this example butanone, heptanone and DMMP). Yet if followed by the doping shown above, analyte peaks are definitively separated enabling specific identification of analytes in the sample.

It will be appreciated that we broadly define doping as the process of adding an analyte for the purpose of affecting ion species behavior. The foregoing demonstrates use of doping to generate negative species, such as SF6, and use of doping to improve ionization efficiency and detection sensitivity.

We also use the term doping to include the step of addition of doping that affects species behavior in such a manner as to change the compensation required to pass the species through the filter. This results in a shift of detection peak(s), usually measured in a changes in DC compensation voltage. This is similar to use of electric field changes to shift peaks, described above. Here, again, creation of a lookup table of data reflecting the affect of a given dopant on peak shift for a given set of filter conditions for a given analyte enables improved separation, detection and identification of analyte.

Figure 21:
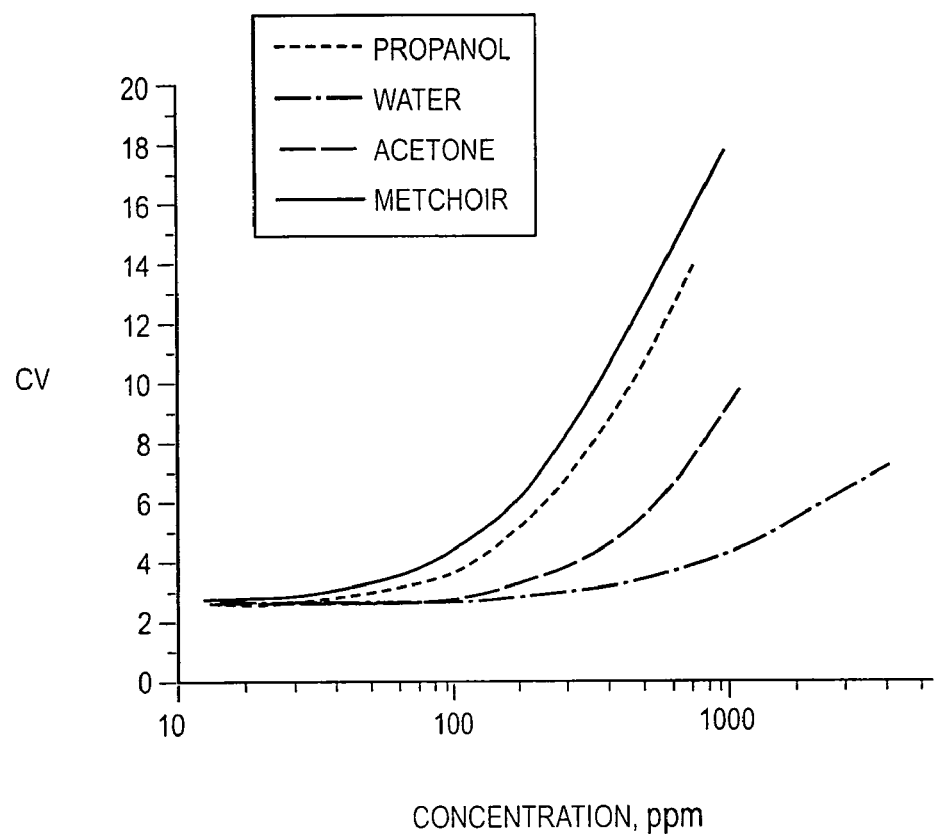
FIG. 21 shows dopant effect upon explosives detection (DNT), in practice of the invention.
Figure 22A:
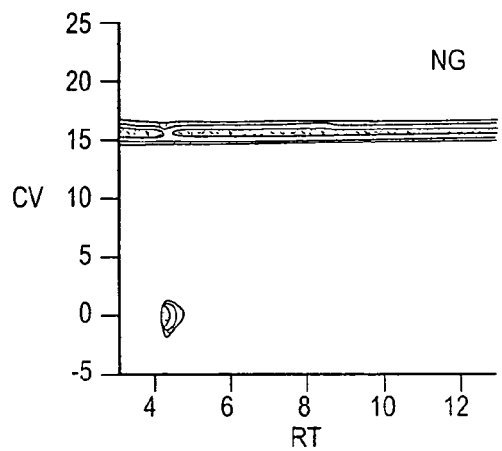
FIG. 22A–E shows undoped detection of explosive compounds.
Figure 22B:
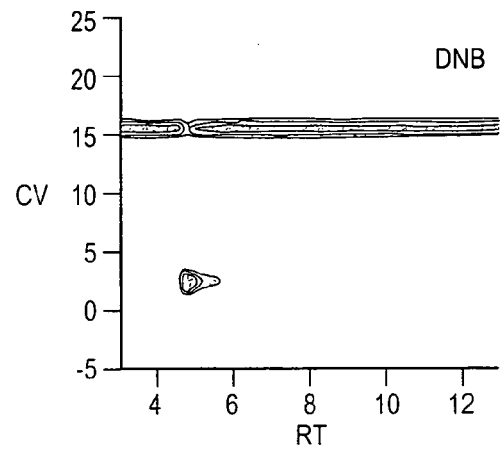
Figure 22C:
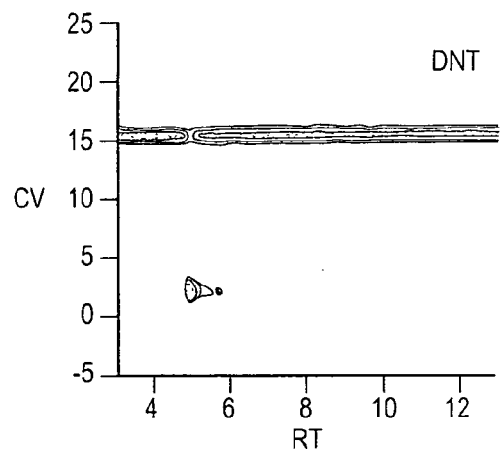
Figure 22D:
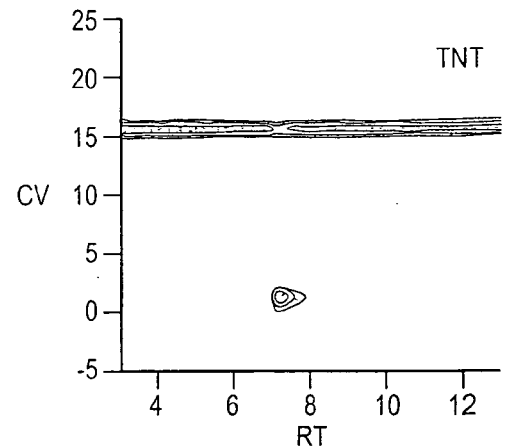
Figure 22E:
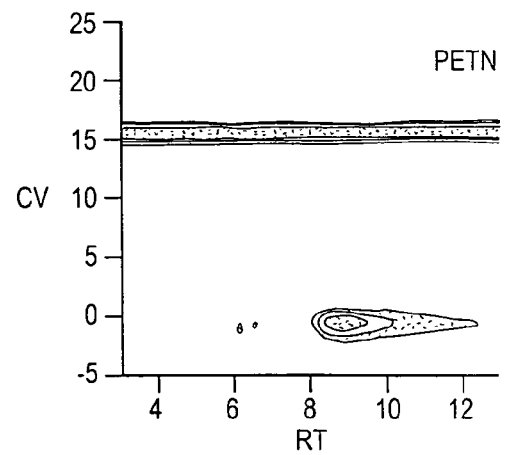
Figure 23A:
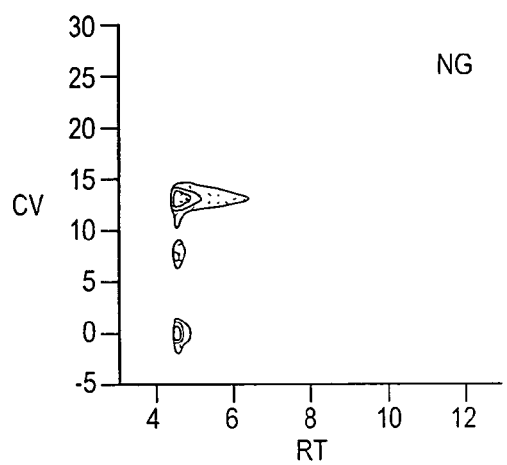
FIG. 23A–E shows doped detection of explosive compounds, using MC dopant in practice of the invention.
Figure 23B:
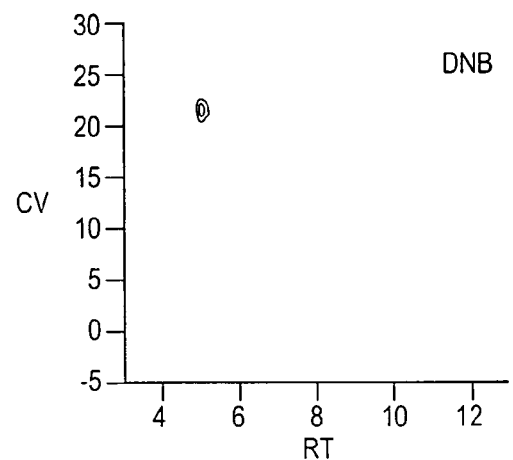
Figure 23C:
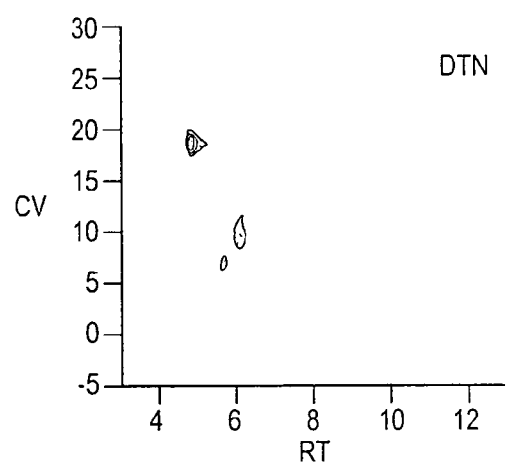
Figure 23D:
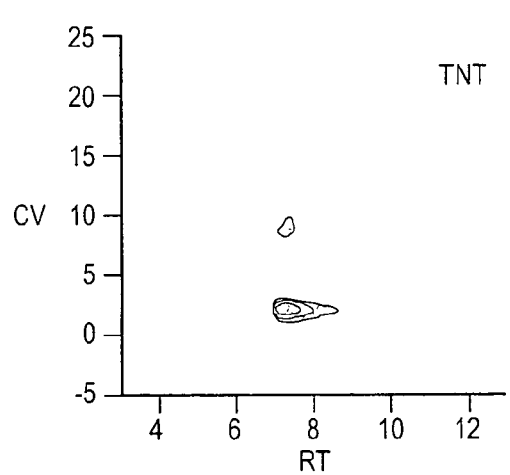
Figure 23E:
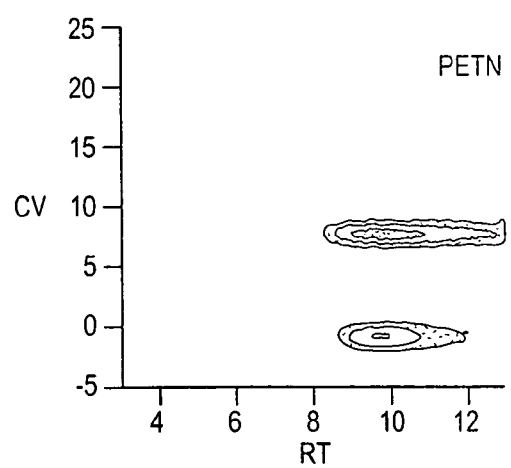

We can use various polar molecules as dopants in practice of the invention. FIG. 21 shows relative performance of four chemicals (MC, propanol, acetone and water) as dopants for use in detection of the explosive DNT, measuring concentration versus amount of compensation in practice of the invention. The best performance for detection of DNT was obtained from MC (methylenechloride or dichloromethane), which provided a greater shift in compensation per unit measure. This experience extrapolates to detection of other explosives, including NG, NS, NC, DNB, PETN, TNT, among others. Several peak shifting doping examples follow, however the invention is not limited to use of MC or to any one example.

Figure 24C:
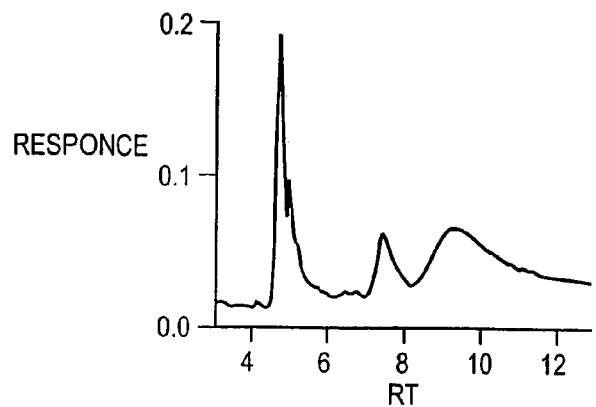
FIG. 24C shows a plot of Response versus Retention Time (RT) corresponding to FIG. 24A.
Figure 24D:
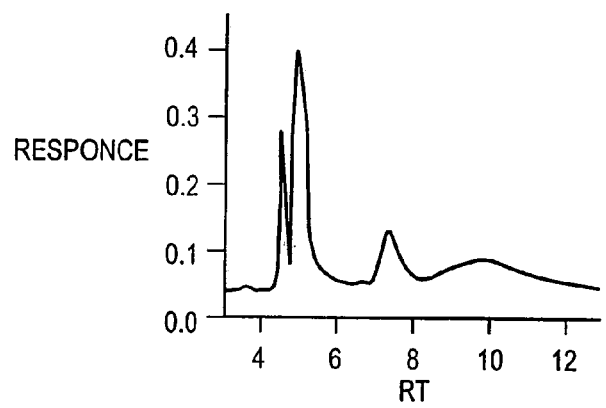
FIG. 24D shows a plot of Response versus Retention Time (RT) corresponding to FIG. 24B.
Figure 24A:
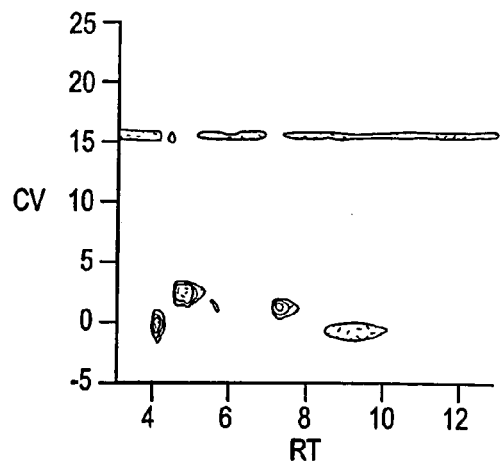
FIG. 24A shows a composite of the detections of FIG. 22.
Figure 24B:
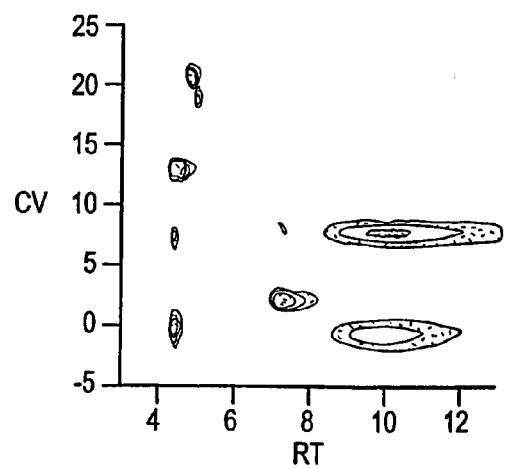
FIG. 24B shows a composite of the detections of FIG. 23, in practice of the invention.

In FIG. 22A–E we show detection spectra a-e for explosive agents NG, DNB, DNT, TNT, and PETN, as elutes from a GC, comparing retention time to compensation voltage, without dopant. In FIG. 23A–E we show better defined and separated detection spectra a-e for the same agents using MC dopant. This benefit is most clearly seen in FIG. 24A–B. FIG. 24A is a composite view of spectra without doping and FIG. 24B is a composite view of spectra with MC doping. FIG. 24C shows a plot of Response versus Retention Time (RT) corresponding to FIG. 24A. FIG. 24D shows a plot of Response versus Retention Time (RT) corresponding to FIG. 24B. In practice of an embodiment of the invention, we calculate the amount of peak shift for each analyte caused by this doping and store this information as identification data for later use in a lookup table for explosives identification.

While use of MC as a dopant for explosive detection and peak shifting is new, we have also found that use of MC simultaneously suppresses background spectra. The result is improved detection sensitivity, capability and efficiency. Still additionally, we are able to use this same MC dopant gas for purging of the DMS system in a possible additional step of the invention. Use of MC, as one of several favored dopants, is therefore advantageous in practice of the invention.

In practice of a multi-step embodiment of the invention, we make a first detection without dopant and a second detection with dopant. We improve identification of species by use of doping-induced peak shifts as generating characteristic identifying data. FIG. 25A–E shows DMS spectra for each of the same explosives: alone, MC alone, and as doped with MC. FIG. 25A shows NG having an undoped peak a1 at ~0 v and a significant shift in compensation for the doped peak a2 at ~13 v.

Figure 25B:
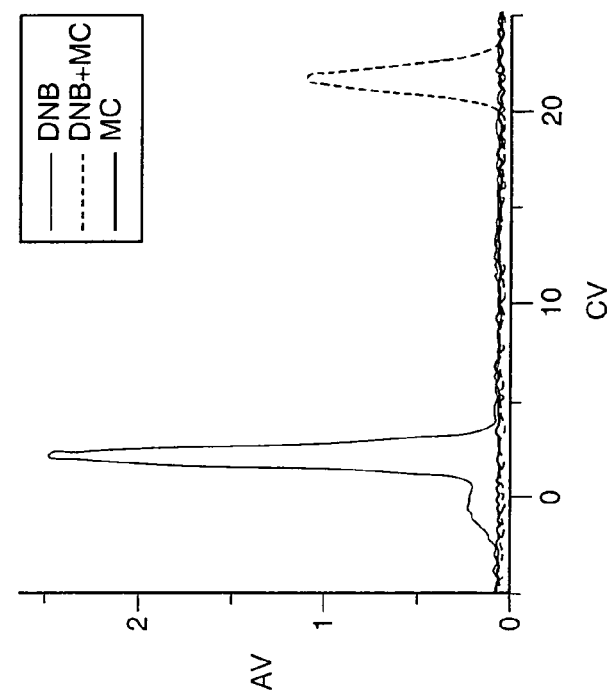
Figure 25A:
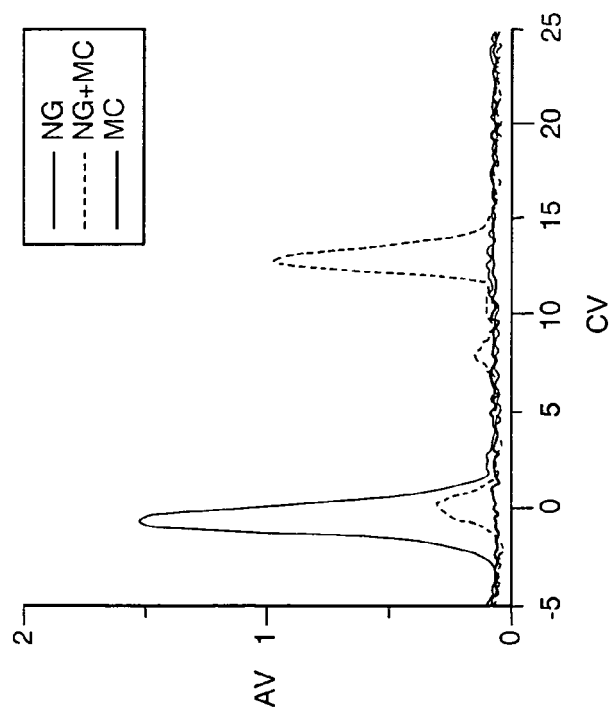
Figure 25D:
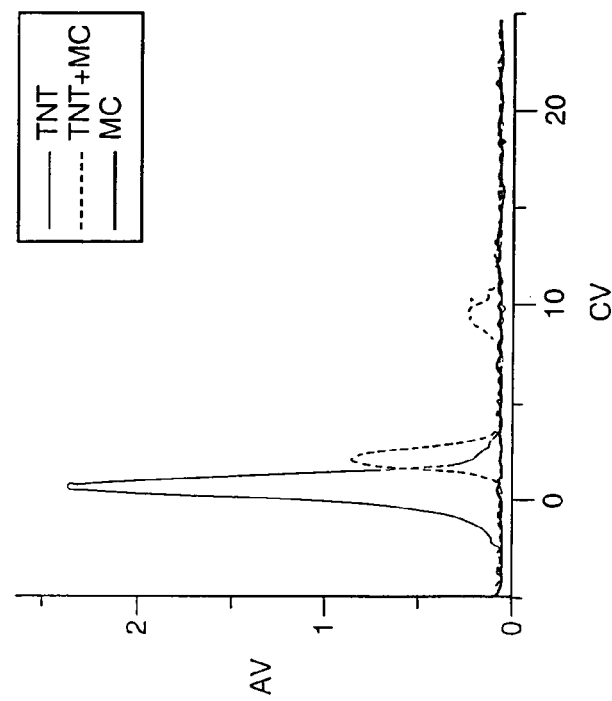
Figure 25C:
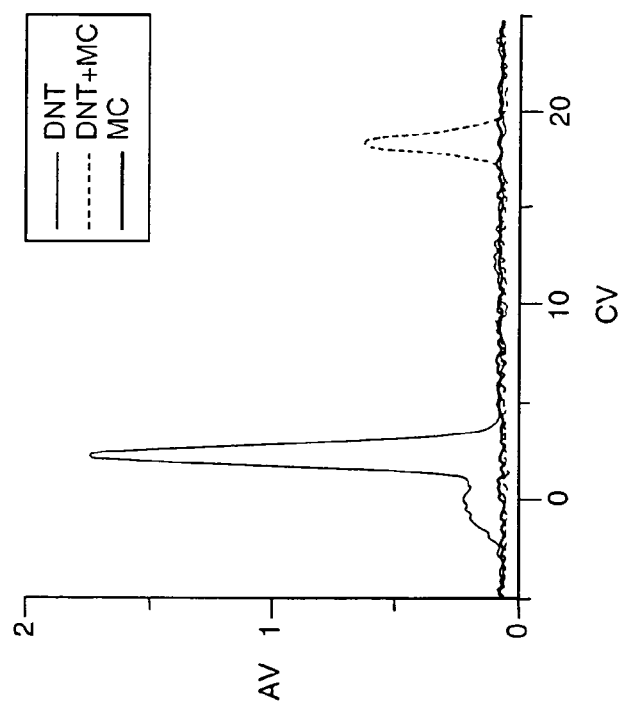

FIG. 25B shows DNB having an undoped peak b1 at ~2 v and a significant shift in compensation for the characteristic DNB doped peak b2 at ~21 v. FIG. 25C shows DNT having an undoped peak c1 at ~2 v and a significant shift in compensation for the characteristic DNT doped peak c2 at ~19 v. FIG. 25D shows TNT having an undoped peak d1 at ~0 v and a significant shift in compensation for the characteristic TNT doped peak d2 at ~10 v. FIG. 25E shows PETN having an undoped peak e1 at ~0 v and a significant shift in compensation for the characteristic PETN doped peak e2 at ~8 v.

These analyte-related peak shifts are signatures which can be used to identify detected species. It will be further appreciated that additional information may be obtained and used in this process. For example, shift of the MC-related peak adds additional characteristic information. In FIG. 25A the MC-related peak a3 is at ~0 v and is part of the signature of the NG+MC cluster peak a2, while the combination of both makes for an accurate signature of NG in this example. This is true for the other analytes, however in FIG. 25B-C the MC peak is not shown because it is off-scale.

These figures demonstrate that use of dopant and amount of dopant are controls that can be used to obtain peak shifts according to the invention. Changes in peak position (which may be measured in terms of compensation voltage) can be used as part of the identification practice of the invention. In one embodiment, we provisionally identify an analyte, add dopant to change the filter conditions to adjust or manipulate the peak position, predict the analyte peak shift, confirm predicted behavior, and therefore make a confirmed analyte identification. This enables a highly reliable analyte identification process with a high degree of confidence in practice of the invention.

As shown in FIG. 21, we can use various polar molecules as dopants in practice of the invention. In one practice of the invention, we control of humidity in the filter environment to provide species separation. It is noted that atmospheric pressure chemical ionization processes are known to be affected by moisture. However, quite unexpectedly, we have found that once the ions are passed into the analytical region of the DMS systems of the invention, unlike conventional ion-based systems, higher levels of moisture actually increase resolution rather than degrade it.

In general there is minimal effect of moisture below 100 ppm on the DMS spectra. This is consistent with IMS where only above 100 ppm does one start seeing shifting of peaks and loss of resolution. There are several possible approaches to controlling the effect of moisture in the DMS. One is by physical means, through controlled addition or removal of moisture (membranes, permeation tubes, temperature). Another means is through the use of algorithms. As an illustration it is possible to track the RIP peak position as a humidity indicator.

Figure 26A:
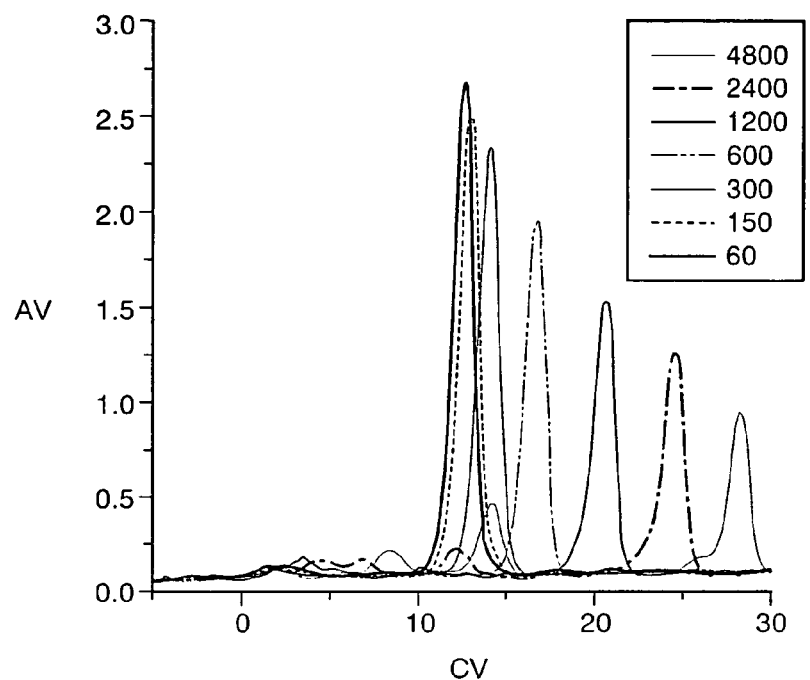
FIG. 26A–C show peak positions for different concentrations of water (A) and DNT/water (B) and a plot of DNT/water peak versus water concentration (C).
Figure 26B:
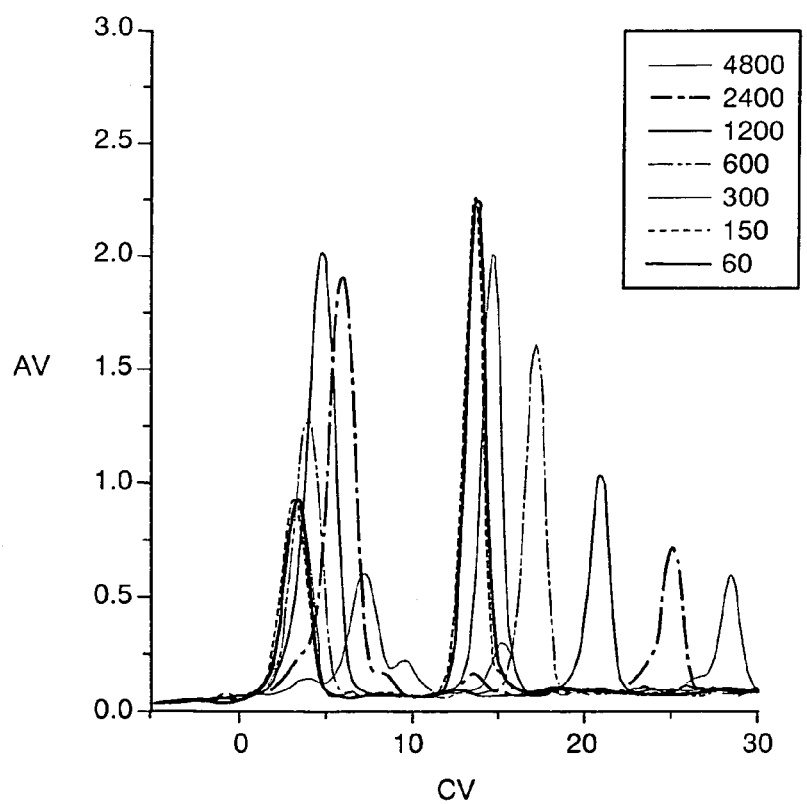
Figure 26C:
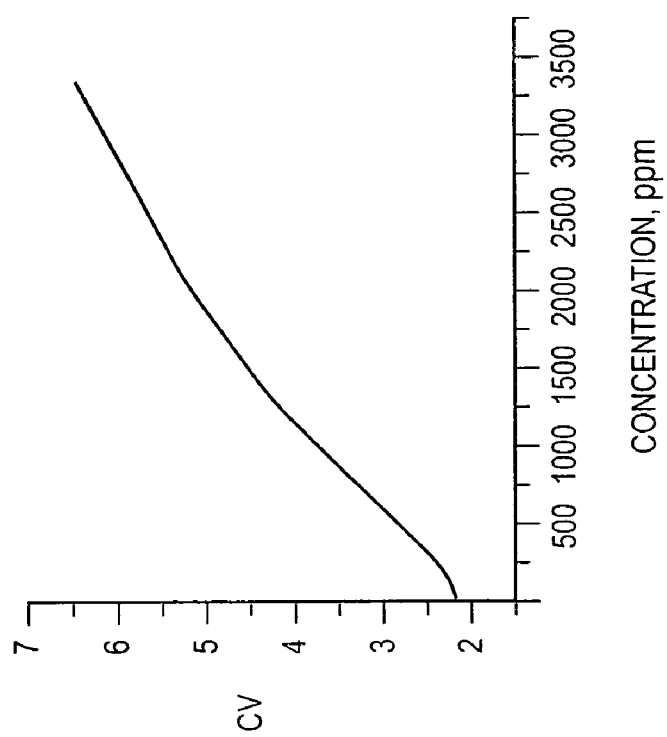

We can apply the control process of the invention to various polar molecules, such as water, in detection of analytes, including explosives, chemical warfare agents, and the like. FIG. 26A–C shows spectra for different concentrations of water in air, for DNT peaks shifted in different concentrations of water, and we plot the relation of DNT peak position to water concentration. FIG. 26A shows how the reactant ion peak position moves away from zero to higher compensation voltages with increasing moisture levels. FIGS. 26B and 26C show the chemical peak shifting in response to increased moisture levels. Generally the DMS spectra with moisture levels from 50–10 ppm are very similar. Notice, in FIG. 26A there is only a slight shift in the RIP peak position from 60–150 ppm.

In FIG. 26A the peaks are distributed from about 11 v to 30 v compensation. In FIG. 26B we add DNT to the sample and analyze the same several concentrations of water. The same distribution of water peaks is again shown, but now we also see DNT/water peaks at various compensation voltages. It will therefore be understood that depending upon the level of water dopant, we can cause a definable or predictable shift in the DNT peak. For example, we can use water at 150 ppm and detect the DNT peak at around 5 v and then we can switch to water at 600 ppm and detect the DNT-water cluster peak with a shift of around 3 v. This shift is characteristic to DNT/water and thus we use detection of an expected shift to confirm presence of DNT using water as a dopant control knob in one practice of the invention.

Figure 27A:
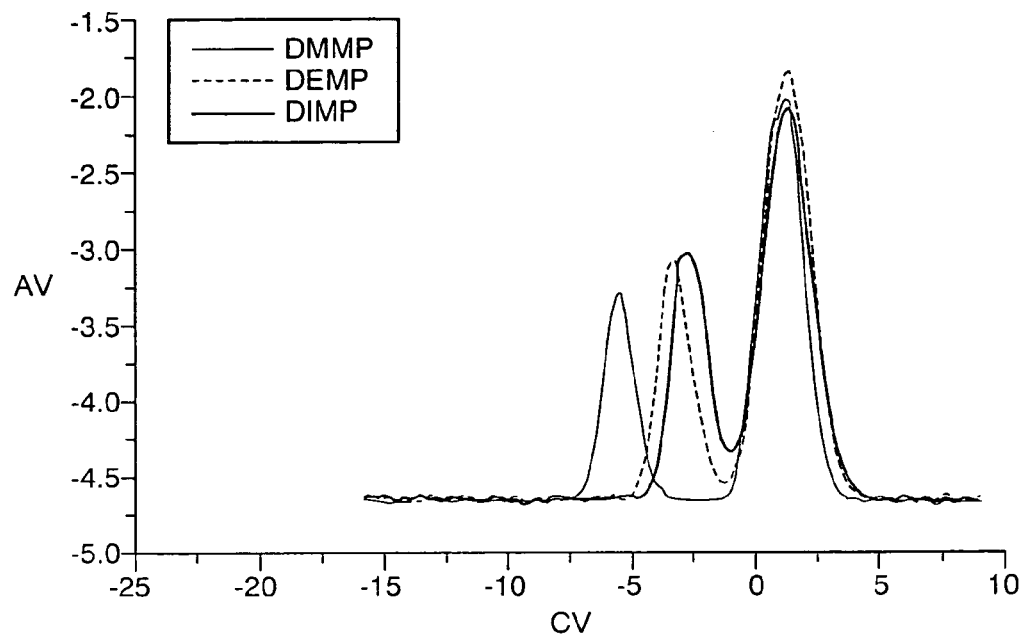
FIG. 27A–C show detection peaks for DMMP, DEMP and DEIP at moisture level of 6 ppm (A) and 95000 ppm (B) and a plot of peak position versus moisture (C), in practice of the invention.
Figure 27B:
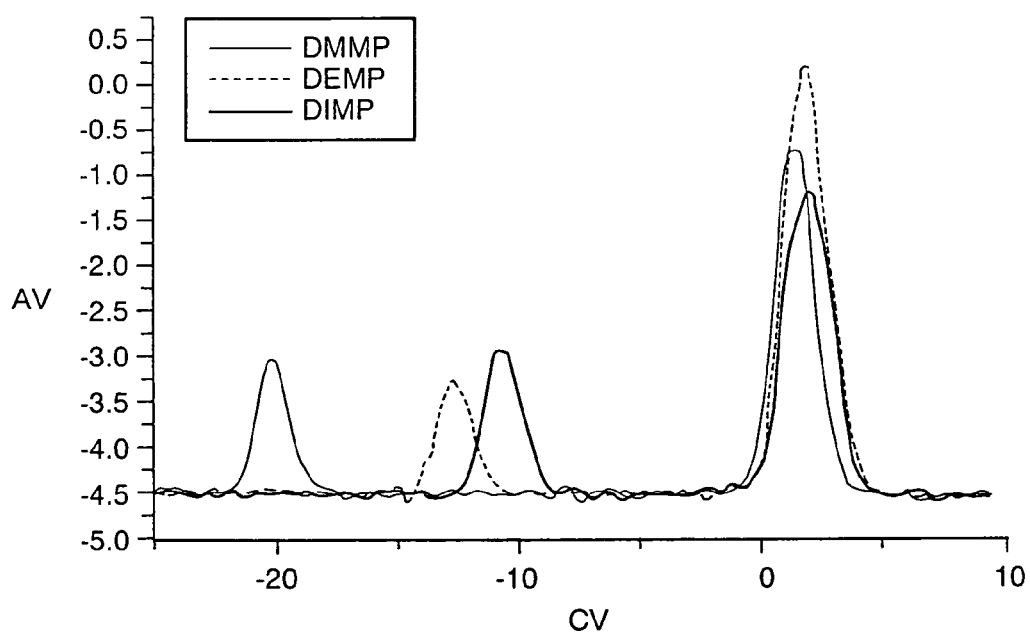
Figure 27C:
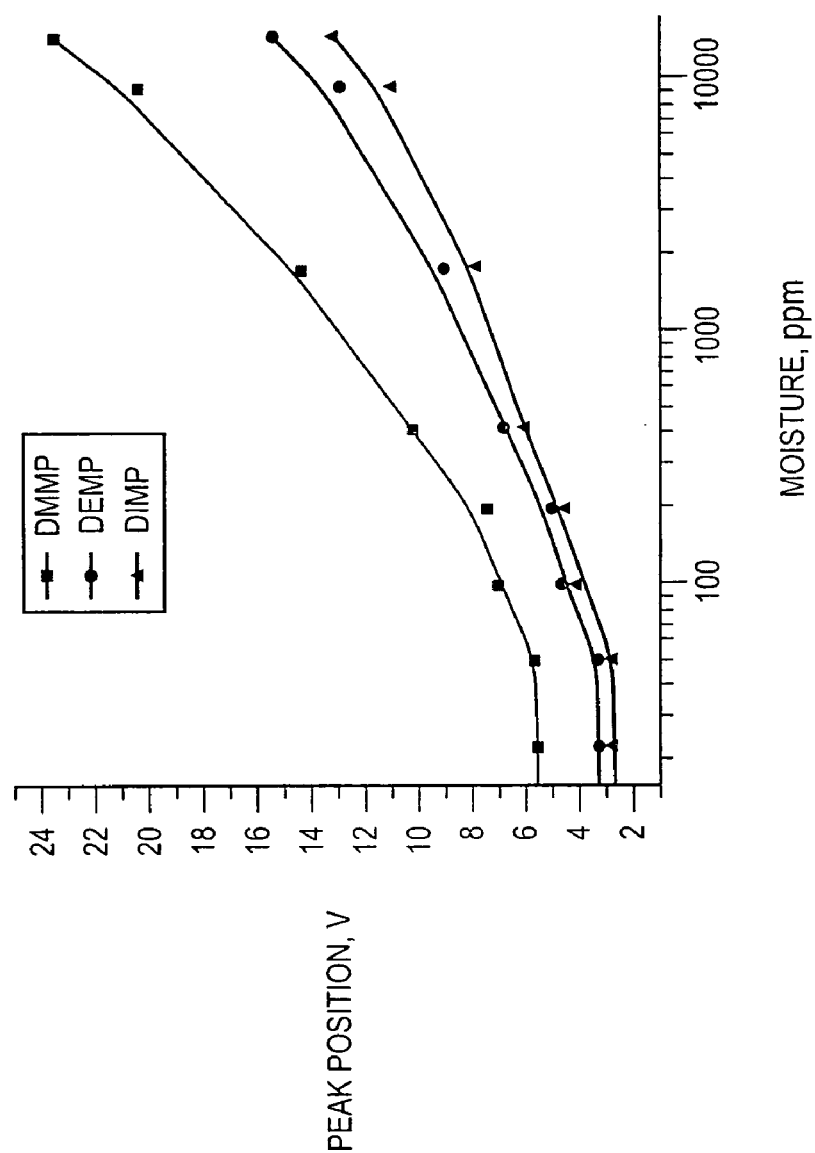

The present invention is not limited to detection of any particular class of analyte. The following examples demonstrate improved detection and identification of organophosphorous compounds using water concentration to shift peaks. FIG. 27A–C shows one example of the effects of moisture for the DMS separation of gas phase ions. A time-varying filed between 0 and 25 kV/cm was applied at ambient pressure for protonated monomers [(MH+(H2O)n] and proton bound dimers [M2H+(H2O)n] of organophosphorous compounds. As shown in Turning to FIG. 27A we show detection of DMMP, DEMP and DIMP. These analytes have similar properties and overlapping spectra, especially the DIMP and DEMP, at very low moisture, however they shift substantially at high humidity. Thus the cluster of chemicals can be provisionally identified at low humidity. Then a second detection is performed at high humidity and the shift of peaks is observed. FIG. 27B shows characteristic response for DMMP, DEMP and DIMP at 95000 ppm. Comparing the shift data between FIG. 27A and B, it will be noted that DIMP shifts from about −2.5 to about −10.5, DEMP shifts from about −3 v to about −13 v, and DMMP shifts from about −6 v to about −30 v. This shift provides improved peak separation between the analytes. FIG. 27C shows peak position versus moisture for the three analytes.

Thus it will now be understood that in a salient aspect of the invention we can provisionally identify an analyte, change the filter conditions based on predicted behavior of that analyte so as to adjust or manipulate its peak position, we confirm the predicted behavior, and therefore we verify analyte identification. This enables a highly reliable analyte identification process with a high degree of reliability and reduced false positives.

Returning again to the embodiment of FIG. 2C, a multi-channel system 11 is shown including dual flow paths 13a, 13b. Having a plurality of channels enables running identical processes in the channels or different processes in each channel. In the latter case variations in electrical (waveform, etc.) or environmental (pressure, humidity, etc.) conditions in the flow path can be used to improve species detection and identification. This plurality of flow paths enables collection of multiple detection data for a sample or samples, which enables improved detection analysis and more reliable species identification. Thus it will be appreciated that the detection results of both flow paths 13a, 13b can be used additively, subtractive, comparatively or otherwise to differentiate, isolate and/or identify detected chemical species, raising confidence in species identification.

In one practice of system 11, an ionization dopant (A-dopant) and chemical sample are introduced at inlet 12a and pass through ionization part 14a into flow path 13a. The ionized A-dopant enhances sensitivity of the system by increasing efficiency of compound ionization, as earlier discussed. (An alternative location of input port 12 is shown at 12a'.)

The ionized sample flows in the carrier gas/dopant toward and is filtered at filter 24a in one embodiment, for downstream detection, including simultaneous detection of positive and negative ions at electrodes 28a, 30a of detector 32a.

In a further practice of system 11, either positive or negative ions from the ionized sample flow are directed into flow path 13b via orifice 25 and by action of properly biased steering electrodes 25a, 25b. Now the ions in flow path 13b are carried by a transport gas from inlet 12b into ion filter 24b, and are filtered and detected downstream in detector 32b, accordingly. This plurality of detection data from detectors 32a, 32b, provides for improved species identification.

In a further embodiment of the invention, the ions entering into flow path 13b are subjected to a resolution dopant (B dopant) that is included as or in the transport gas introduced at inlet 12b. The B-dopant improves peak resolution by differentially impacting spectral peak position (i.e., characteristically effecting the amount of compensation voltage), which will depend upon ion-mobility characteristics of the detected analyte(s).

As will now be appreciated, these and other embodiments of the multi-channel system 11 enable control or manipulation of the analytical function within one or several flow path(s) for obtaining improved species separation and identification.

Regulation of Pressure

In conventional DMS spectrometers, the ions from the sample are carried by a carrier gas through the system. In conventional IMS systems a counter-flowing gas stream is used essentially for cleaning the drift region. In any event, to the extent that the gas is intermingled with the sample ions, the presence of the gas in the ion separation region can complicate ion detection due to gas phase interactions or reactions, significant diffusion processes, and formation of dimer bond complexes, and so forth. This reduces the sensitivity and resolution of the system.

In these prior art practices, the presence of a high density gas mixed in the ion population requires the use of a large electric field to effect ion discrimination. As a result, the power consumption is increased. Power consumption is a very critical parameter for portable devices.

Figure 28:
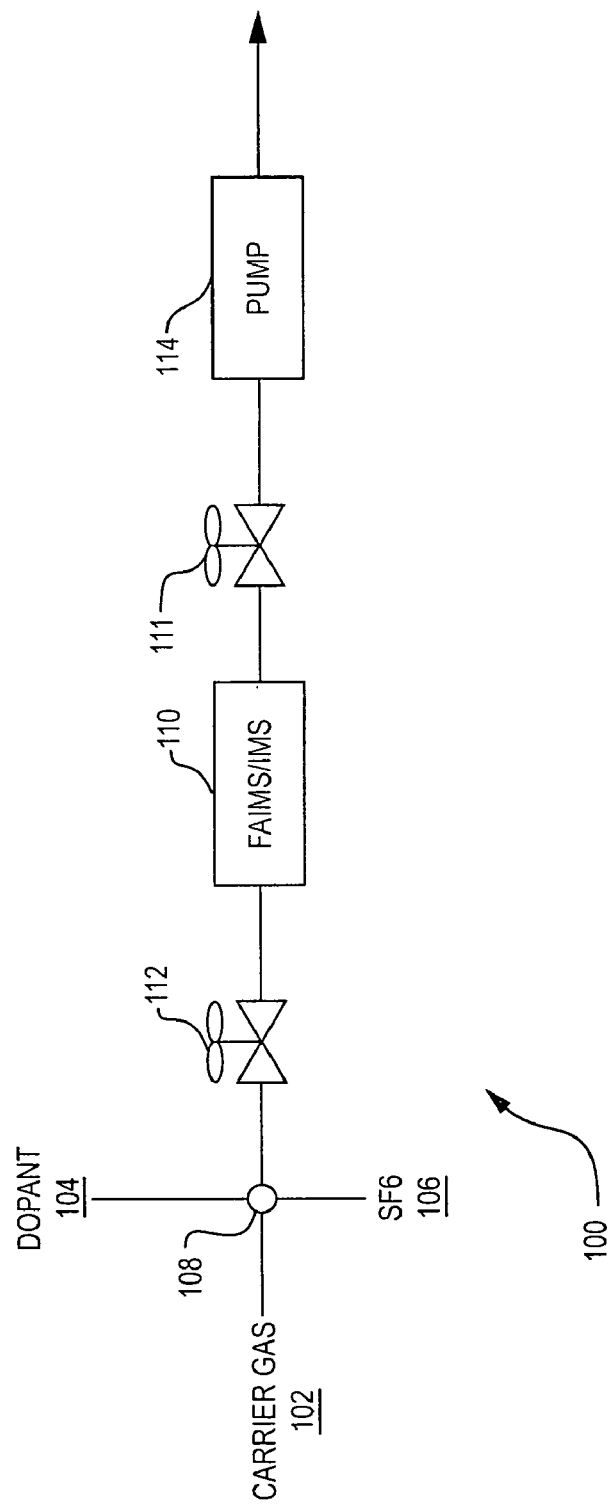
FIG. 28 shows a dopant control apparatus, in practice of the invention.

Looking now at FIG. 28, there is shown a novel ion mobility-based spectrometer 100 where a carrier gas 102 and sample 106 (such as SF6) and, optionally dopant 104, are mixed in a chamber 108, and are introduced into a filter system 110. Ion filter system 110 may include a field asymmetric ion mobility spectrometer, such as spectrometer 10 described above, in which case the ion mobility spectrometer will include filter 24 and detector 32 discussed above; or system 110 may include another type of ion mobility-based spectrometer, such as a time-of-flight ion mobility spectrometer. Flow rate is regulated by a valve 112. System pressure is controlled via pump 114 and valve 116.

In practice of the invention we have found that by regulating (and preferably reducing) the pressure of the system, system sensitivity can be improved. When we reduce the pressure, less carrier gas is present amongst the target ions so that there is, among other things, less ion destruction (e.g., through quenching) and less masking of the mobility characteristics of the ions (e.g., due to random collisions occurring within the filtering electronic field). In addition, as the gas conditions (density N or pressure P) are reduced, the electric field can also be reduced (maintaining the E/N or E/P ratio), so that power consumption can be reduced. Hence system sensitivity can be improved and power consumption can be reduced. This is particularly advantageous in making a hand-held detector.

Figure 29A:
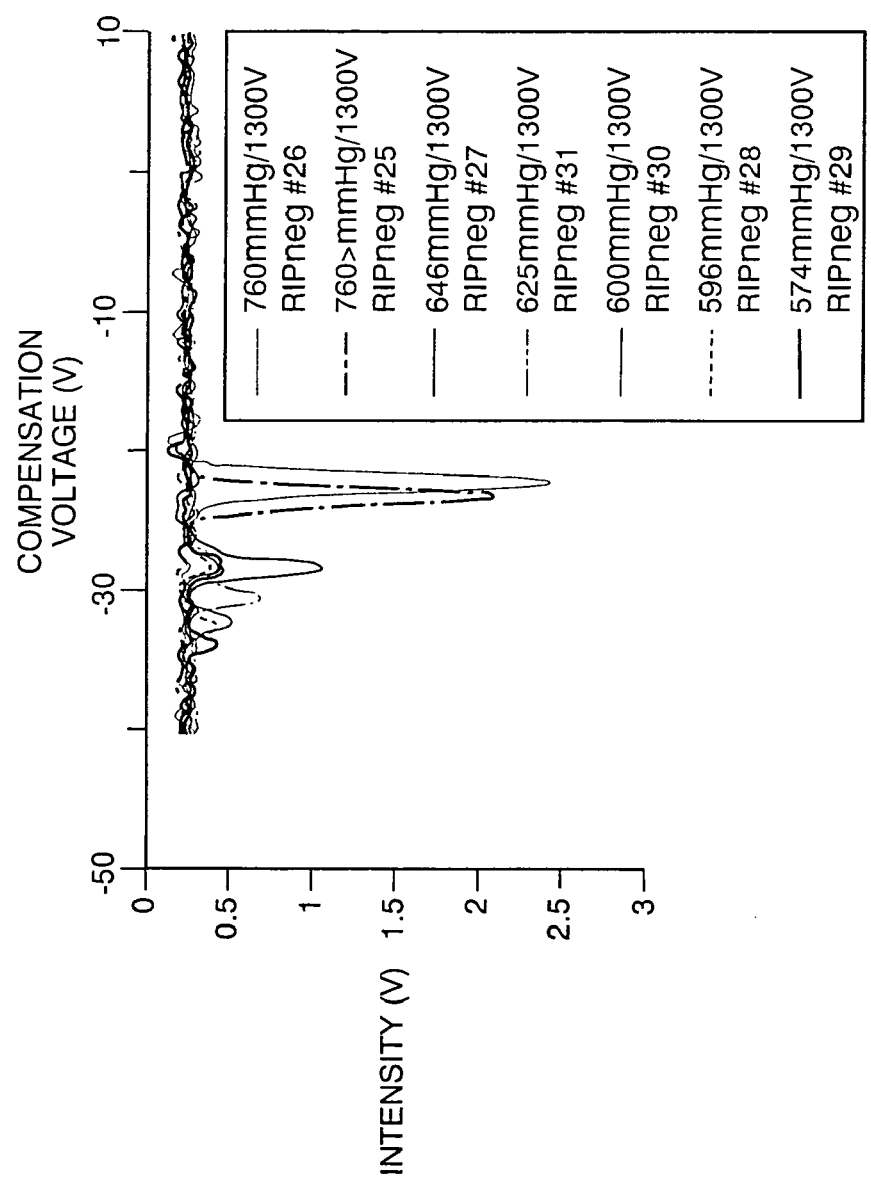
FIG. 29A–B shows effect of pressure on negative (A) and positive (B) mode background spectra, in practice of the invention.
Figure 29B:
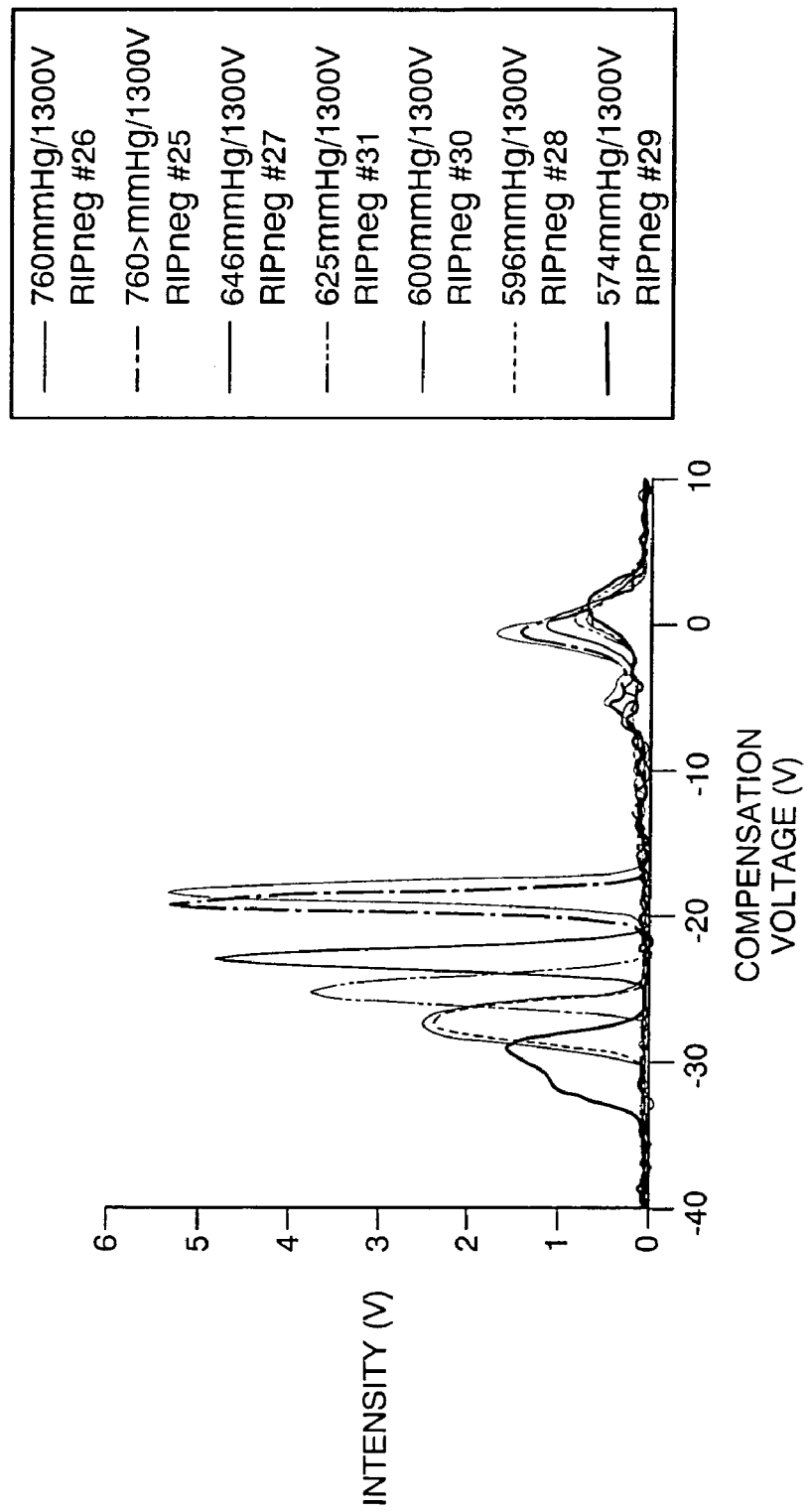

FIG. 29 shows effect of changes in pressure on negative and positive background spectra, when all other parameters, flow rate, RF voltage, temperature, are constant. In this illustrative experiment RF was 1300V. The system was stable and test results were reproducible for same and other RF voltages and pressures.

Analysis of these spectra shows that with decreasing pressure the absolute value of compensation voltage for both (the positive and negative) RIP peaks is increased (peaks are shifted to left), while impurity (or cluster) peaks around zero compensation shift in the opposite direction. Also, peak intensity decreases with reduced pressure. The effect of pressure is stronger for negative peaks versus compared to positive mode peaks, wherein the negative mode peak shift is greater and intensity decreases more rapidly.

For lower pressure conditions, the peaks become broader, probably due to increased separation between different species of ions. For example, it is understood that in the case of positive mode the RIP peak species include combinations of protonated water peaks $(H2O)nH+$, and in negative mode these species include combinations of oxygen-containing ions, such as $(H2O)n\ O2—$. (The level of clustering (n) depends upon the level of moisture.)

Figure 30B:
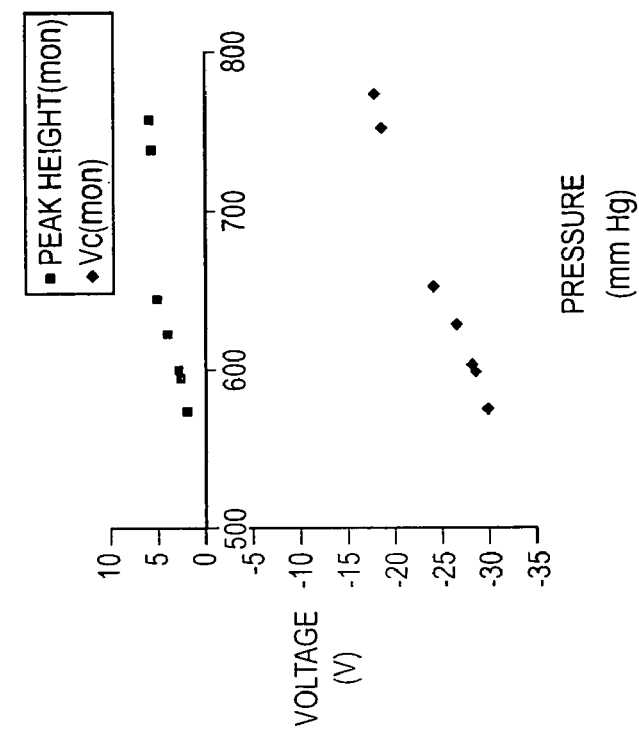
FIG. 30A–B shows effect of pressure on negative (A) and positive (B) background ion peak parameters, in practice of the invention.
Figure 30A:
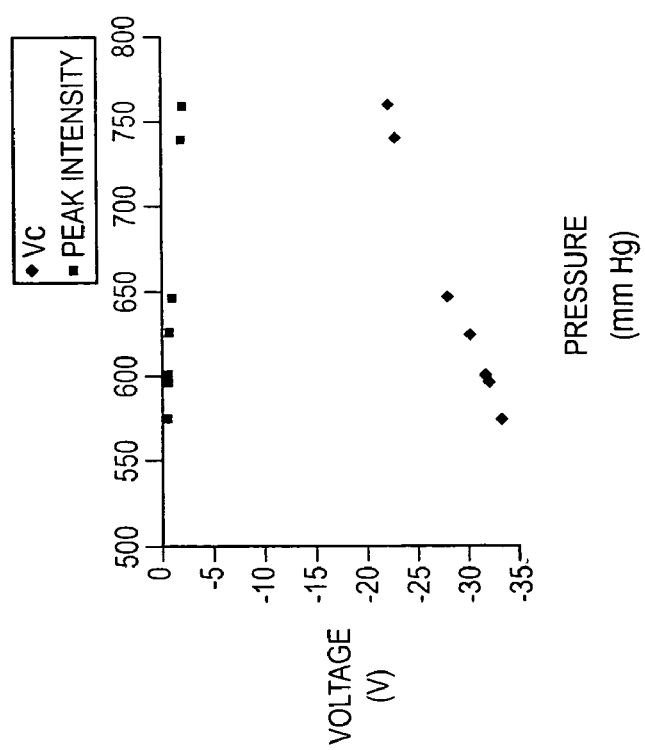

The quantified effect of pressure on peak parameters (shown as peak intensity and compensation voltage in FIG. 29) may be directly observed in FIG. 30. This data shows that the level of effect on peak parameters is more significant at lower pressure conditions.

Figure 31A:
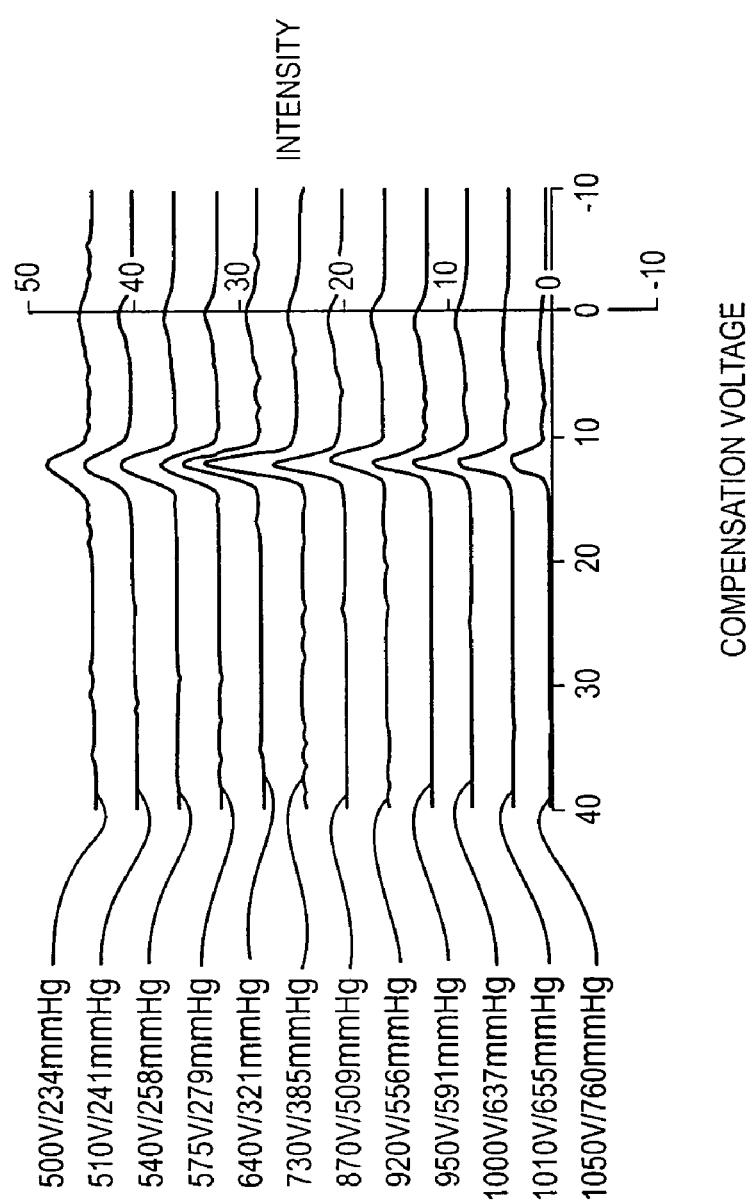
FIG. 31A–B shows adjustment of RF voltage for changes in pressure for positive (A) and negative (B) background spectra, in practice of the invention.
Figure 31B:
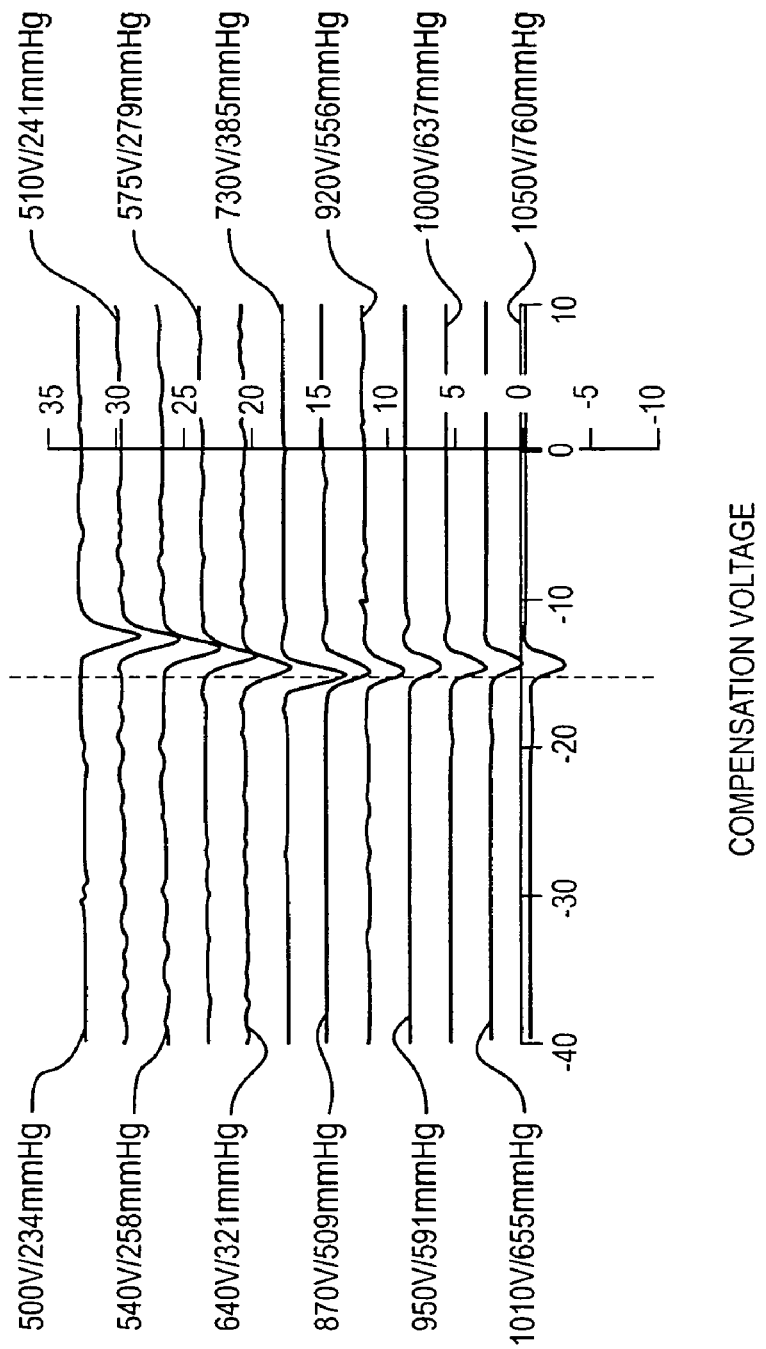

In FIG. 31, we show the level of influence of pressure on peak position in terms of RF voltage. We have observed that the shift of RIP after changing pressure can be compensated by changing RF voltage so as to return the peak to the previous Vc indicating peak position. The change in pressure correlates with the new RF voltage.

We have observed that making a change in pressure has a different impact on positive and negative RIP peaks (compare FIG. 29 and FIG. 30). Therefore, adjusting positive and negative peaks requires different levels of RF voltage correction. FIG. 31 demonstrates adjusting the positive mode peaks back to their initial position and noting the new RF value; the resulting negative peak position is offset from its original position. In general, this offset can provide information as to the difference in the characteristic alpha parameter between the positive and negative modes for this ion species. (See M070 for further alpha discussion.) In general we have found that the level of effect of pressure is increased with decreasing pressure.

FIG. 31 shows background spectra for positive and negative modes at different pressures and RF levels, for a set flow rate. The key shows the combination of RF voltage and pressure required to keep the positive RIP peak at the same position compensation position (measured as Vc). From analysis of this data one can see that for lower pressure conditions a lower RF voltage was required. Again the analysis shows that the level of pressure effect (i.e., the amount of required RF adjusted voltage) increases with decreasing pressure. For example, for changing pressure P~100 mmHg (between 760–655) the required adjustment of RF voltage was V=1050–1010=40V. Meanwhile, for the same pressure change at a lower pressure range (655–556 mmHg), the value of adjusted RF voltage was more than two times V=1100–920=90V.

In this experiment the peak intensity does not change as dramatically as it did when the electric field was not compensated (FIG. 29 and FIG. 30). Explanation: the trajectory of recorded ions movement in the analytical gap is not significantly changed; this follows because increasing velocity of transfer direction movement ($v=K*E$) due to increasing coefficient of mobility at lower pressure conditions is compensated by decreasing RF electric field. Non-monotonic behavior of negative peak position in this experiment can be explained in terms of the differences of a parameter of positive and negative ions species.

The quantified effect of electric field compensation for pressure decreasing may be directly observed in FIG. 32. This data may be useful for practical applications. For example, at reduced pressure, the DMS will have increased resolution compared to atmospheric pressure. As well, operation at lower pressure requires lower RF voltage and therefore decreased power consumption and reduced sensor and drive circuit design requirements. For example, according FIG. 32 one can see that by decreasing pressure to 0.3 atm the RF voltage is decreased about in half.

Figure 33A:
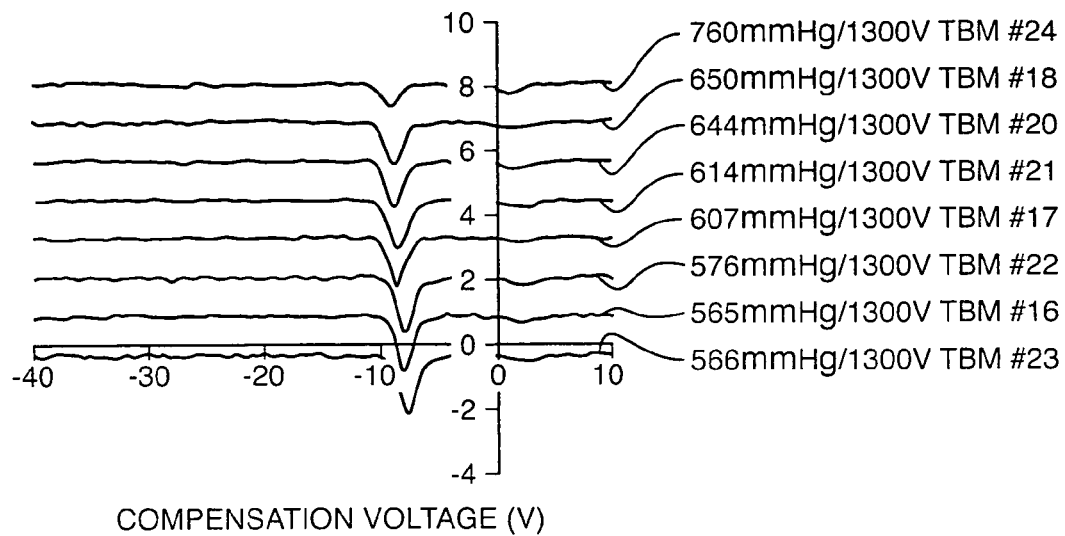
FIG. 33A–B shows the effect of pressure on negative (A) and positive (B) TBM spectra, in practice of the invention.
Figure 33B:
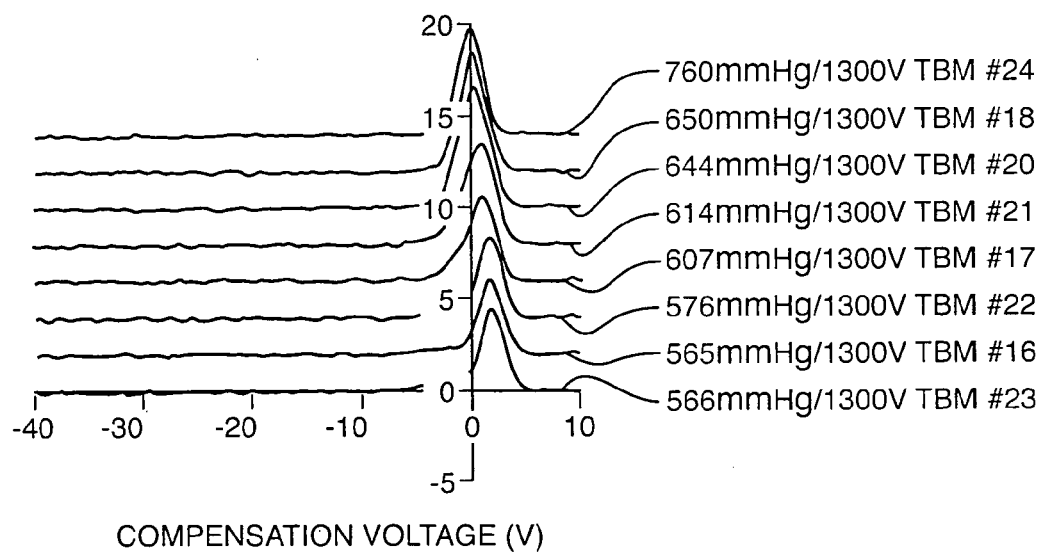

FIG. 33 shows the effect of different pressures on negative (A) and positive (B)spectra of TBM (tert-Butylmercaptan or tert-Butylthiol) [$C_4H_9SH$], with RF voltage held constant.

Figure 34A:
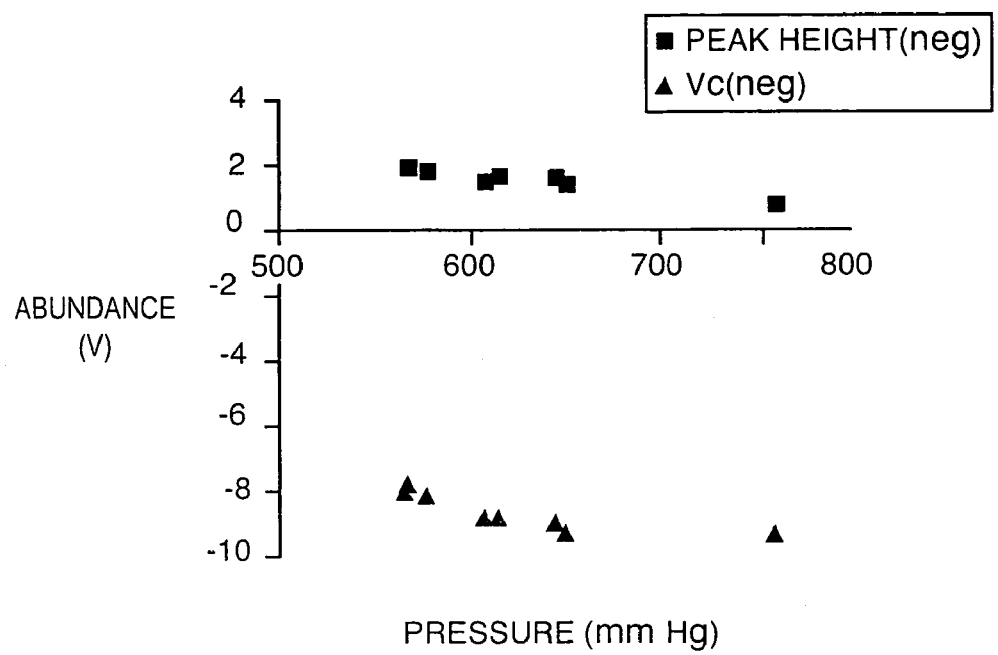
FIG. 34A and B shows the effect of pressure on negative (A) and positive (B) TBM ion peak parameters, in practice of the invention.
Figure 34B:
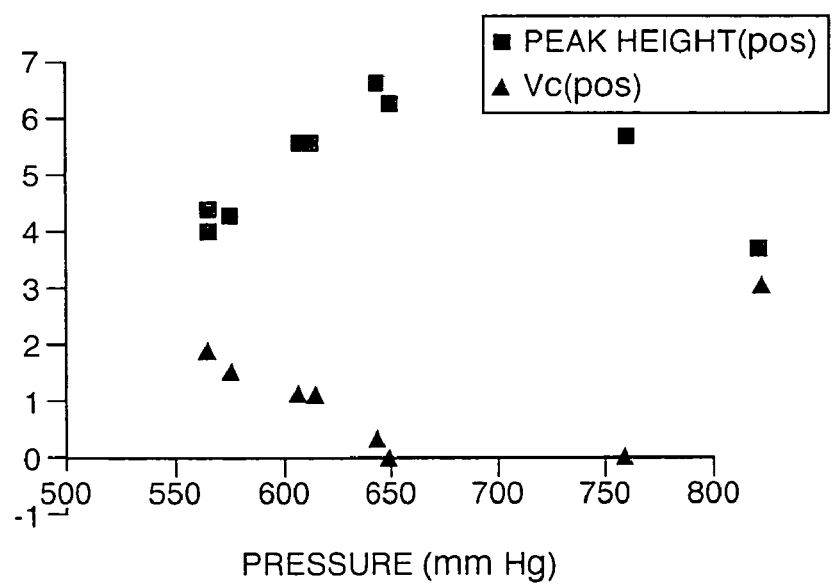

FIG. 33 shows that the TBM spectra also are changed according to change in pressure. Direction for the peak position changing is opposite to shift in RIP peaks. Level of change is less than for RIP (see FIG. 29). For example, the peak position and intensity do not change approaching atmospheric pressure (between 760–650 mmHg). The quantified effect of changing TBM peak parameters is shown in FIG. 34, showing the effect of pressure on negative (a) and positive (b) TBM ions peaks parameters.

In another illustration, it was seen that RIP peaks are more sensitive to changing pressure than TBM peaks. Direction of peak shifting for RIP peaks and TBM was opposite. With decreasing pressure, RIP peaks shifted in the direction of increasing absolute value of compensation voltage, while the TBM peaks moved in opposite direction. Thus it now will be understood that changes in pressure yield predictable changes to species and therefore can be pressure can be used as a "knob" which can be adjusted to separate detection peaks and improve identification of compounds in a sample.

It will therefore be appreciated that changes to pressure impacts background and analyte spectra. The present invention makes use of the quantifiable effect of pressure on peak parameters.

Figure 35A:
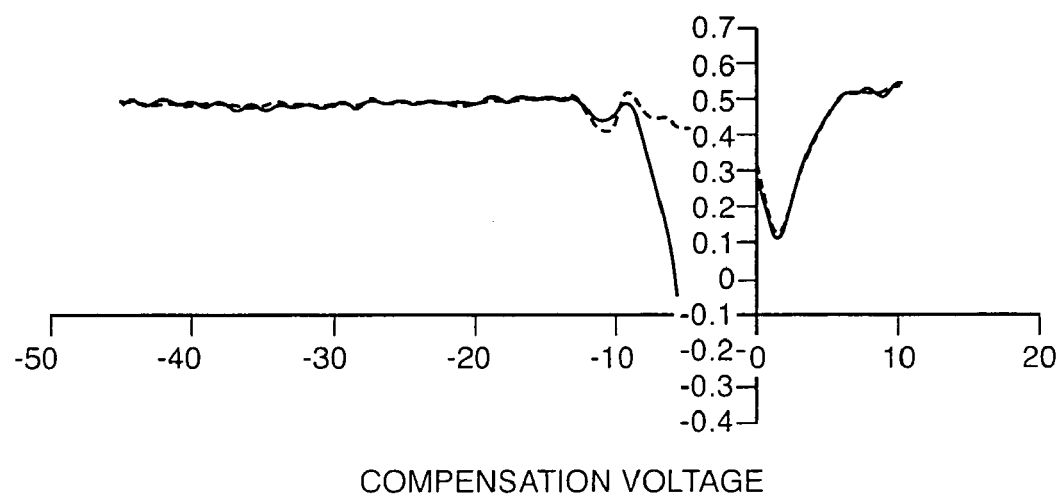
FIG. 35A–B shows effect of reduced pressure on negative (A) and positive (B) SF6 spectra, in practice of the invention.
Figure 35B:
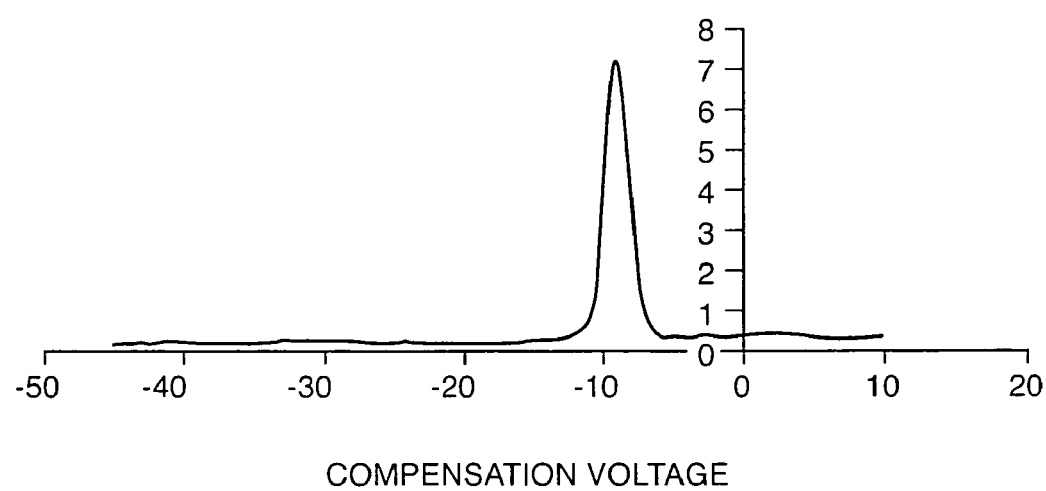

In one experiment, shown in FIG. 35A and FIG. 35B, SF6 at 250 ppm was ionized with acetone dopant in UV ionization, where spectrometer 10 was operated at an RF of 500 v, at 0.3 atmosphere and with laboratory air. In the negative mode (FIG. 35A), the background spectra without SF6 and the detection peak for SF6 are shown. The SF6 detection peak appears at a compensation voltage of about −5.5 volts, while in the positive mode (FIG. 35B) the acetone dopant was detected at a compensation of about −9 volts. Operating at 500 v is significant, since this is sizable reduction in RF voltage, thereby resulting in lower power consumption while still providing excellent SF6 identification capability.

As well, in this example, the lab air was at about ~5000 ppm humidity. Thus it will be appreciated that the present invention allows SF6 to be easily ionized using a non-radioactive source with the assistance of a dopant, and detected in low electric operating conditions (e.g., with an RF voltage of approximately 500 v) at reduced operating pressure (e.g. 0.3 atm), even with elevated humidity (e.g., 5000 ppm).

It will be appreciated further that we have found that ionization of a high energy of ionization chemical, such as SF6, may be quenched in the presence of high humidity and oxygen. Thus, the invention overcomes quenching by lowering the operating pressure of the apparatus; this reduced pressure effectively decreases the effect of humidity and oxygen.

It is further noted that it is preferable that the ratio of electric field to gas conditions, density N or pressure P, expressed as E/N or E/P, should be monitored and adjusted to obtain uniform detection results for a given compound. Practice of embodiments of the present invention enable reducing gas operating pressure which not only results in better ionization, such as for SF6, but it also allows the electric field to be lowered while maintaining the E/P ratio. Thus, a reduction in operating pressure reduces power consumption, thereby permitting a smaller, lighter-weight, lower-cost and lower-power device.

Flow Control Apparatus

It is known that ion mobility is affected by factors such as particle mass, particle charge and particle cross-section. As well, control of polar molecules (such as $H_2O$, $CO_2$, $NO_2$, $NH_4$, etc.) can be used to favorably affect mobility and detection. More specifically, we have found that by adjusting or optimizing the humidity, and/or the concentration of other polar molecules, in the sample, we can improve detection sensitivity in practice of the invention. This is surprisingly true, notwithstanding our example above describing low pressure detection of SF6 which seems insensitive to high moisture level., In practice of the invention, a sample can be adjusted by removing or adding appropriate molecules before or after ionization. In some cases, depending upon the sample, a reduced level (such as reduced humidity) can reduce clustering and can improve system sensitivity. This is true where clustering changes mobility and therefore masks the identify of a compound of interest.

But alternatively, in some circumstances, it may be advantageous to introduce polar molecules into the sample to encourage clustering. For example, where it is difficult to otherwise differentiate between two different ion species, addition of selected polar molecules can enable these ion species to be separated, if they have different clustering characteristics. Thus removal or addition of polar molecules can be used as an additional control in the detection process in practice of the invention.

Figure 36:
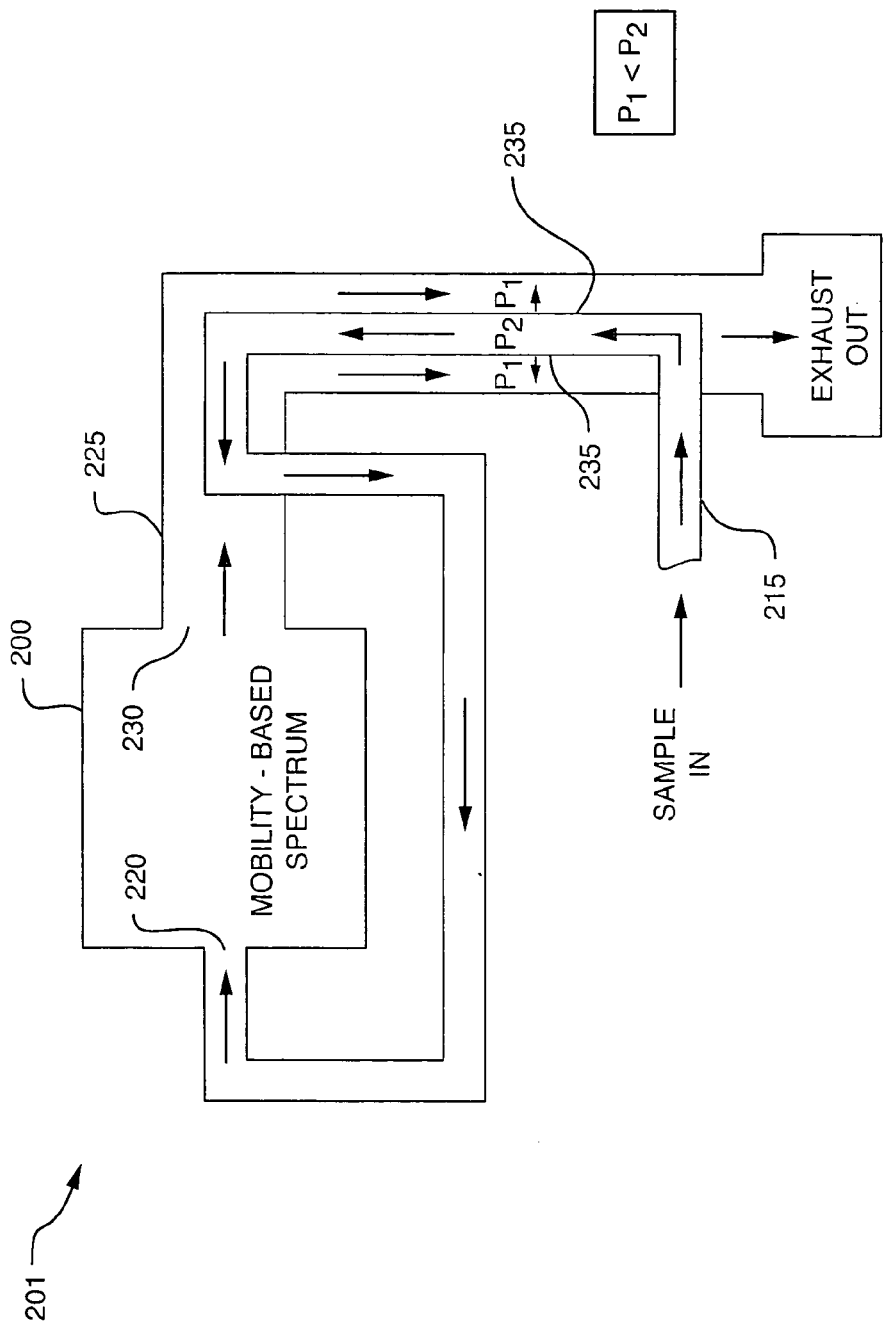
FIGS. 36–37 show improved flow control apparatus of the invention.

In one illustrative embodiment of the invention, shown in FIG. 36, ion-mobility based spectrometer 200 of an ion detection and identification system 201 is provided for analyzing a sample 205. The sample is first passed through a humidity adjustment region 210 prior to being introduced into spectrometer 200. In a broadest aspect of the invention, humidity adjustment region 210 may be any apparatus adapted to adjust the humidity of the sample prior to introduction into spectrometer 200, e.g., by reducing or adding humidity to the sample prior to or after ionization. In practice of an embodiment of the invention, system 201 may includes a DMS spectrometer such as spectrometer 10 described above or may comprise a time-of-flight IMS system, or the like as spectrometer 200.

Figure 37:
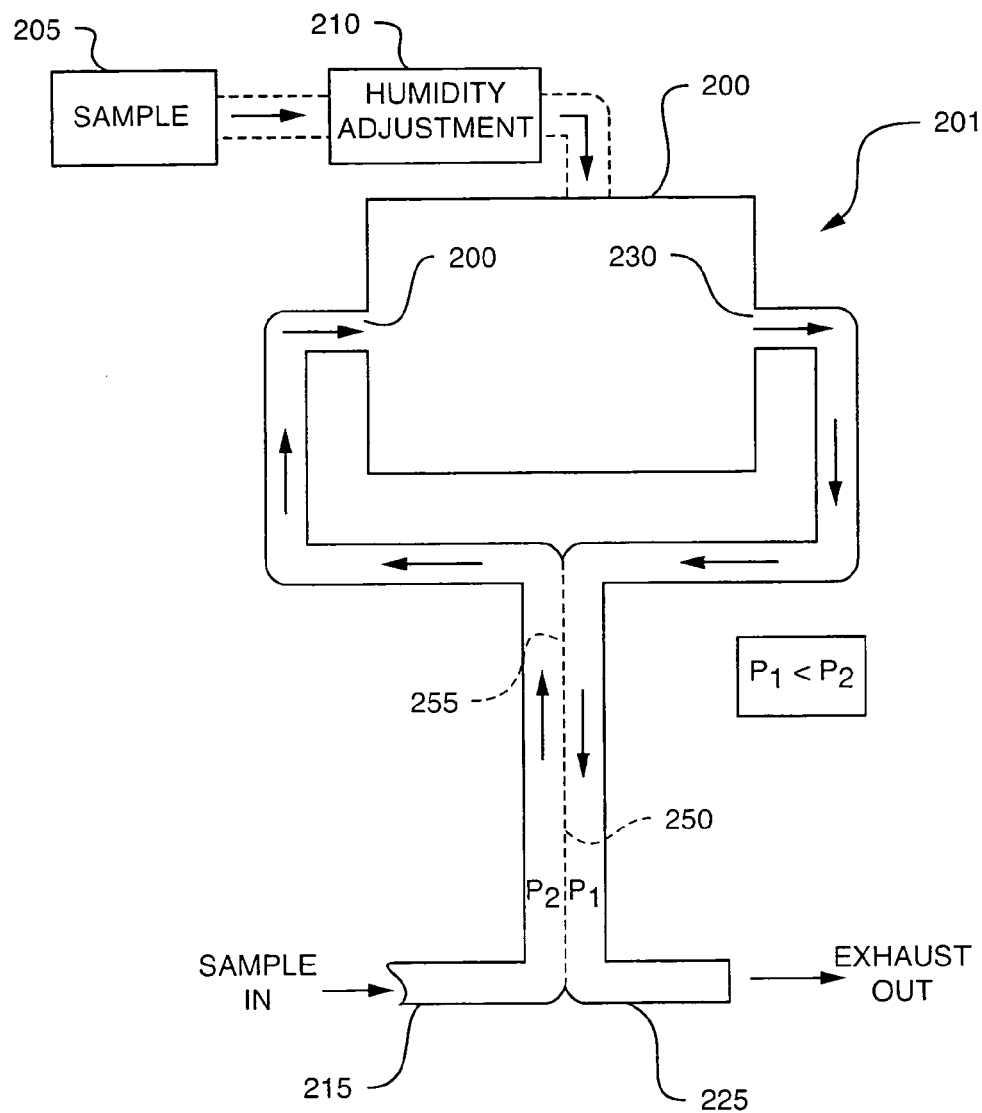

Turning to FIG. 37, there is shown a system 201 of the invention for controlling the humidity of a sample introduced into ion mobility-based spectrometer 200. For example, in the case of reduction of humidity, an input line 215 carries the sample from a source to the input 220 of ion mobility spectrometer 200. An output line 225, connected to the output 230 of spectrometer 200, receives the spectrometer exhaust and carries it off. Input line 215 extends through at least a portion of the interior of the output line 225, and is formed at least partly out of a water-permeable membrane 235, such that water contained in the sample flowing through input line 215 may pass through the wall of input line 215 and be carried away by output line 225. In this respect it will be appreciated that inasmuch as output line 225 is typically connected to a pump which purges the contents of output line 225, output line 225 will tend to have a lower pressure (P1) than input line 215 (P2), such that P1<P2, so as to induce moisture to pass through the water-permeable membrane wall of the input line 215 and into the interior of output line 225 in the exhaust.

FIG. 38 illustrates an alternative approach for reducing the humidity of a sample prior to introduction into ion mobility-based spectrometer 200. Here, system 201 includes input line 215 and output line 235 sharing a common water-permeable wall 250 formed of a water-permeable membrane 255 such that water contained in the sample flowing through input line 215 may pass through wall 250 and into output line 225, where it will be carried away by the spectrometer exhaust. Again, a pump or other arrangement may be employed to assure that the input pressure P2 is greater than the output line pressure P1, so as to assist the moisture transfer through the membrane for exhaust.

In several methods of the invention, we detect known species and correlate with RF field, compensation, pressure, humidity, and/or other parameters. We create a data store describing at least one analyte preferably at various parameter levels. In one embodiment, the data source is accessed as a lookup table.

Now we detect and identify a compound based on comparison to this stored data. A single comparison may be adequate where a system is dedicated to detection of a particular species. An optimized set of RF and compensation values may be selected along with values representing selected pressure and humidity. These optimized parameters are selected to meet the criterion of increased reliability in identification by a single detection set. Presence or absence of a species can be indicated by conventional announcement means.

However, in another practice of the invention, we include the process of differential peak shifting. This peak manipulation is based on our observation that different ion species of chemicals exhibit different mobility behavior as a function of different operating conditions and that as operating conditions are changed peaks will shift characteristically. Thus we can develop a family of measurement data that are characteristic of a given compound, including peak location and/or shift data. We can record such data and use it for comparison with detection data when detections are made of unknown compounds in those selected operating conditions.

We also have found one or several parameters of the filter conditions that can be selected and adjusted to achieve peak shifting after a species is detected and provisionally identified. Different species shift differently and characteristically. Upon detection of a characteristic shift, the provisional species identification is verified and announcement of species identity is made with confidence. Thus, in one method, we can provisionally identify at least one peak even in the presence of overlapping peaks, making a provisional species identification, and based on the effect of known operating conditions. We manipulate these operating conditions and observe the effect of the adjusted operating conditions upon peaks. It is noted that the amount of peak shift is typically species specific and enables species identification by amount of shift as one parameter. We correlate shifts in peak position and intensity with operating conditions and reference our stored data to make a species identification.

It will now be understood that it is possible to control operating conditions and to discriminate between compounds that are ordinarily difficult to separately identify by other means. Selection of operating conditions enables isolation of an ion species of interest. Furthermore, because the system of the invention matches detection data with stored data, we can select operating conditions that will produce detection data that is matchable to stored data, to determine a species is present in the sample.

It should be furthermore understood that the invention is applicable not only to field asymmetric ion mobility systems but may be applied in general to ion mobility spectrometry devices of various types, including various geometries, ionization arrangements, detector arrangements, and the like, and brings new uses and improved results even as to structures which are all well known in the art. Furthermore, in practice of an embodiment of the invention, the output of the DMS filter may be detected off board of the apparatus, such as in a mass spectrometer or other detector, and still remains within the spirit and scope of the present invention.

It will now be appreciated by a person skilled in the art that we optimize ion species analysis in practice of embodiments the invention by adjustment of operating conditions. These knobs are defined to enable adjustment of field, DC compensation, frequency, duty cycle, asymmetry, pressure, flow rate, gas composition, moisture, and/or ionization type/energy, among others.

Practices of the present invention may benefit from or be applied to a system which incorporates the teachings of co-pending U.S. patent application Ser. No. 10/187464, filed Jun. 28, 2002, by Lawrence A. Kaufman et al., for SYSTEM FOR COLLECTION OF DATA AND IDENTIFICATION OF UNKNOWN ION SPECIES IN AN ELECTRIC FIELD, incorporated herein by reference.

The high sensitivity, rugged design and ease of use and setup of the invention are advantageous for many applications that involve chemical detection. A simplified hand-held device of the invention is dedicated to detection at just two "data points", and yet reliably detects and identified the ion species of interest. This practice may be augmented by dual mode detections. The result is added reliability in chemical detection in a simplified device.

It will now be appreciated that in practice of the invention we optimize the filter field, its electrical properties and its environment, in an ion-mobility-based system to amplify differences in ion mobility behavior. Species are then separated, detected and identified based on this optimization. We can further optimize the process by detecting ion polarity, and we can optimize ionization and/or separation by using dopants. Thus in practice of the present invention, we apply various strategies for improved isolation, detection and identification of chemicals in a sample based on aspects of ion mobility behavior.

It should, of course, also be appreciated that numerous changes may be made to the disclosed embodiments without departing from the scope of the present invention. While the foregoing examples refer to specific compounds, this is intended to be by way of example and illustration only, and not by way of limitation. It should be appreciated by a person skilled in the art that other chemical molecules may be similarly ionized and detected, with or without the use of dopants, and/or pressure regulation, and/or humidity adjustment, and/or adjustment of the concentration of other polar molecules.

Therefore, while this invention has been particularly shown and described with references to the above embodiments, it will be understood by those skilled in the art that various changes in form and details may be made therein without departing from the scope of the invention encompassed by the appended claims

What is claimed is:

1. A system for analyzing a sample comprising,
an asymmetric electric field for dispersing ions of the sample,
an ion filter having filter electrodes separated by an analytical gap and defining a flow path, within which the asymmetric field is formed,
a controller for establishing a first set of operating conditions for the ion filter to separate first ones of the dispersed ions from others of the dispersed ions and, based at least in part on the first set of operating conditions, establishing a second set of operating conditions to separate second ones of the dispersed ions from others of the dispersed ions,
a detector along the flow path downstream of the ion filter for detecting the spectra of separated ions wherein the controller is in electrical communication with the detector, and
a data store for enabling the controller to identify an ion species based on a comparison of the detected spectra of the first ones of dispersed ions with a spectra of at least one known ion species in the data store at the first set of operating conditions and a comparison of the detected spectra of the second ones of dispersed ions with a spectra of at least one known ion species in the data store at the second set of operating conditions.

2. The system of claim 1, wherein the controller includes a processor for selectively establishing at least one of the first set of operating conditions and the second set of operating conditions.

3. The system of claim 1, wherein the controller establishes the second set of operating conditions in response to the detected spectra of the first ones of dispersed ions.

4. The system of claim 1, wherein the data store is configured as a data lookup table.

5. The system claim 1, wherein operating conditions include parameters, the parameters including at least one of an asymmetric field strength, a compensation field level, waveform characteristics, RF frequency, duty cycle, gas composition, pressure, temperature, amount of $H_2O$, amount of polar molecules, flow path flow rate, and an amount of a dopant.

6. The system of claim 5, wherein said compensation field is derived from a DC voltage applied to at least one of the filter electrodes.

7. The system of claim 5, wherein the set of operating conditions includes a scan of at least one parameter of the operating conditions.

8. The system of claim 5, wherein the set of operating conditions includes a scan of a plurality of parameters of the operating conditions.

9. The system of claim 1, wherein the controller establishes a third set of operating conditions in the ion filter to separate third ones of the dispersed ions from other ions.

10. The system of claim 5, wherein the dopant includes one of methylenechioride, dichloromethane, water, an analyte, toluene, acetone, and benzene.

11. A system for analyzing a sample comprising,
an asymmetric electric field for dispersing ions of the sample,
an ion filter having filter electrodes separated by an analytical gap and defining a flow path, within which the asymmetric field is formed, and
a controller for establishing a first set of operating conditions for the ion filter to separate first ones of the dispersed ions from others of the dispersed ions and, based at least in part on the first set of operating conditions, establishing a second set of operating conditions to separate second ones of the dispersed ions from others of the dispersed ions,
wherein operating conditions include parameters, the parameters including at least one of an asymmetric field strength, a compensation field level, waveform characteristics, RF frequency, duty cycle, gas composition, pressure, temperature, amount of $H_2O$, amount of polar molecules, flow path flow rate, and an amount of a dopant, the dopant including one of methylenechioride, dichloromethane, water, an analyte, toluene, acetone, and benzene, and
wherein the dopant concentration is at least one of about 5000 PPM, greater than or equal to about 600 PPM, greater than or equal to about 150 PPM, greater than or equal to about 100 PPM, greater than or equal to about 60 PPM, and greater than or equal to about 2 PPM.

12. The system of claim 5, wherein the controller is configured to predict the effect of adjusting the operating condition from the first set of operating conditions to the second set of operating conditions, the controller being capable of identifying at least one ion species measured in terms of a change in at least one characteristic of the detected spectra between the first set of operating conditions and the second set of operating conditions.

13. The system of claim 5 comprising an ionization source along the flow path upstream of the ion filter for generating ions.

14. A system for analyzing a sample comprising,
an asymmetric electric field for dispersing ions of the sample,
an ion filter having filter electrodes separated by an analytical gap and defining a flow path, within which the asymmetric field is formed,
a controller for establishing a first set of operating conditions for the ion filter to separate first ones of the dispersed ions from others of the dispersed ions and, based at least in part on the first set of operating conditions, establishing a second set of operating conditions to separate second ones of the dispersed ions from others of the dispersed ions, and
an ionization source along the flow path upstream of the ion filter for generating ions,
wherein operating conditions include parameters, the parameters including at least one of an asymmetric field strength, a compensation field level, waveform characteristics, RF frequency, duty cycle, gas composition, pressure, temperature, amount of $H_2O$, amount of polar molecules, flow path flow rate, and an amount of a dopant, the dopant including one of methylenechioride, dichloromethane, water, an analyte, toluene, acetone, and benzene, and
wherein the dopant includes at least one of an ionization dopant and a resolution dopant, the ionization dopant being introduced into the flow path in proximity with the ionization source to adjust sample ionization, the resolution dopant being introduced into the flow path in proximity with the ion filter to adjust spectral peak resolution.

15. The system of claim 1, wherein at least one ion filter electrode is formed on a substrate.

16. A system for analyzing a sample comprising,
an asymmetric electric field for dispersing ions of the sample,
an ion filter having filter electrodes separated by an analytical gap and defining a flow path, within which the asymmetric field is formed, and
a controller for establishing a first set of operating conditions for the ion filter to separate first ones of the dispersed ions from others of the dispersed ions and, based at least in part on the first set of operating conditions, establishing a second set of operating conditions to separate second ones of the dispersed ions from others of the dispersed ions,
wherein at least one ion filter electrode is formed on a substrate and at least a portion of the substrate includes silicon.

17. A system for analyzing a sample comprising,
an asymmetric electric field for dispersing ions of the sample,
an ion filter having filter electrodes separated by an analytical gap and defining a flow path, within which the asymmetric field is formed, and
a controller for establishing a first set of operating conditions for the ion filter to separate first ones of the dispersed ions from others of the dispersed ions and, based at least in part on the first set of operating conditions, establishing a second set of operating conditions to separate second ones of the dispersed ions from others of the dispersed ions,
wherein at least a portion of the flow path is formed by a process selected from at least one of micromachining, etching, and dicing.

18. A system for analyzing a sample comprising,
an asymmetric electric field for dispersing ions of the sample,
an ion filter having filter electrodes separated by an analytical gap and defining a flow path, within which the asymmetric field is formed, and
a controller for establishing a first set of operating conditions for the ion filter to separate first ones of the dispersed ions from others of the dispersed ions and, based at least in part on the first set of operating conditions, establishing a second set of operating conditions to separate second ones of the dispersed ions from others of the dispersed ions,
wherein at least the ion filter and controller are included on a single chip.

* * * * *